US008450302B2

(12) United States Patent
Ciufolini et al.

(10) Patent No.: US 8,450,302 B2
(45) Date of Patent: May 28, 2013

(54) 2-(3-AMINOARYL) AMINO-4-ARYL-THIAZOLES AND THEIR USE AS C-KIT INHIBITORS

(75) Inventors: Marco Ciufolini, Lyons (FR); Camille Wermuth, Strasbourg (FR); Bruno Giethlen, Illkirch (FR); Alain Moussy, Paris (FR); Jean-Pierre Kinet, Lexington, MA (US)

(73) Assignee: AB Science, Paris (FR)

( * ) Notice: Subject to any disclaimer, the term of this patent is extended or adjusted under 35 U.S.C. 154(b) by 0 days.

(21) Appl. No.: 13/016,100

(22) Filed: Jan. 28, 2011

(65) Prior Publication Data

US 2011/0201620 A1 Aug. 18, 2011

Related U.S. Application Data

(63) Continuation of application No. 10/632,101, filed on Aug. 1, 2003, now Pat. No. 7,423,055, and a continuation-in-part of application No. 11/779,633, filed on Jul. 18, 2007, now abandoned, which is a continuation of application No. 10/523,018, filed as application No. PCT/IB03/03685 on Jul. 31, 2003, now abandoned.

(60) Provisional application No. 61/298,953, filed on Jan. 28, 2010, provisional application No. 60/400,064, filed on Aug. 2, 2002.

(51) Int. Cl.
*A01N 43/00* (2006.01)
*A61K 31/33* (2006.01)

(52) U.S. Cl.
USPC ........................................................ 514/183

(58) Field of Classification Search
None
See application file for complete search history.

(56) References Cited

U.S. PATENT DOCUMENTS

| | | | |
|---|---|---|---|
| 3,192,225 A | 6/1965 | Spivak et al. | |
| 3,201,409 A | 8/1965 | Dexter et al. | |
| 3,467,666 A | 9/1969 | Dexter et al. | |
| 3,740,420 A | 6/1973 | Herschler et al. | |
| 3,743,727 A | 7/1973 | Herschler | |
| 3,772,295 A | 11/1973 | Robba et al. | |
| 3,989,816 A | 11/1976 | Rajadhyaksha | |
| 4,322,433 A | 3/1982 | Leslie et al. | |
| 4,343,940 A | 8/1982 | Kreighbaum et al. | |
| 4,379,454 A | 4/1983 | Campbell et al. | |
| 4,405,616 A | 9/1983 | Rajadhyaksha | |
| 4,411,893 A | 10/1983 | Johnson | |
| 4,460,372 A | 7/1984 | Campbell et al. | |
| 4,540,269 A | 9/1985 | Nishiyama | |
| 4,575,515 A | 3/1986 | Sandborn | |
| 4,615,699 A | 10/1986 | Gale et al. | |
| 5,217,999 A | 6/1993 | Levitzki et al. | |
| 5,302,606 A | 4/1994 | Spada et al. | |
| 5,330,992 A | 7/1994 | Eissenstat et al. | |
| 5,521,184 A | 5/1996 | Zimmerman | |
| 5,556,611 A | 9/1996 | Biesalski | |
| 5,656,643 A | 8/1997 | Spada et al. | |
| 5,682,252 A | 10/1997 | Ando | |
| 5,710,158 A | 1/1998 | Myers et al. | |
| 5,714,493 A | 2/1998 | Myers et al. | |
| 5,721,237 A | 2/1998 | Myers et al. | |
| 5,776,020 A | 7/1998 | Barone | |
| 5,792,783 A | 8/1998 | Tang et al. | |
| 5,834,504 A | 11/1998 | Tang et al. | |
| 5,883,113 A | 3/1999 | Tang et al. | |
| 5,883,116 A | 3/1999 | Tang et al. | |
| 5,886,020 A | 3/1999 | Tang et al. | |
| 5,906,202 A | 5/1999 | Schuster et al. | |
| 6,291,514 B1 | 9/2001 | Illig et al. | |
| 6,697,600 B2 | 2/2004 | Nishikino et al. | |
| 6,892,945 B2 | 5/2005 | Shishido | |
| 7,423,055 B2 * | 9/2008 | Ciufolini et al. | ............... 514/342 |
| 2001/0044545 A1 | 11/2001 | Dhanoa et al. | |
| 2003/0158199 A1 | 8/2003 | Stieber et al. | |
| 2003/0199002 A1 * | 10/2003 | Hekimi et al. | .................. 435/7.2 |
| 2004/0110801 A1 | 6/2004 | Makovec et al. | |
| 2004/0110810 A1 | 6/2004 | Ciufolini | |
| 2007/0231378 A1 * | 10/2007 | Chang et al. | .................. 424/450 |

FOREIGN PATENT DOCUMENTS

| | | |
|---|---|---|
| EP | 0 602 851 | 10/1996 |
| EP | 0 520 722 | 12/1996 |
| EP | 0 584 222 | 10/1997 |
| EP | 0 934 931 | 8/1999 |
| JP | 63-136462 | 9/1988 |
| JP | 63-028447 | 12/1996 |
| JP | 2002-185796 | 6/2002 |
| JP | 2003-134307 | 5/2003 |
| JP | 4333676 | 11/2004 |

(Continued)

OTHER PUBLICATIONS

Erp et al., "Clinical Pharmacokinetics of Tyrosine Kinase Inhibitors," Cancer Treatment Reviews, 2009.*
Manley et al., "Imatinib: A Selective Tyrosine Kinase Inhibitor," European Journal of Cancer, vol. 38, Suppl. 5 (2002) S19-S27.*
Weisberg et al., "Beneficial Effects of Combining Nilotinib and Imatinib in Preclinical Models of BCR-ABL Leukemias," Blood 2007, 109:2112-2120.*
Capdeville et al., "Imatinib: the First 3 Years," European Journal of Cancer, vol. 38 Suppl. 5 (2002) S77-S82.*

(Continued)

*Primary Examiner* — Craig Ricci
*Assistant Examiner* — Jared D Barsky
(74) *Attorney, Agent, or Firm* — Clark & Brody

(57) ABSTRACT

The present invention relates to the use of masitinib or a pharmaceutically acceptable salt thereof, and in particular of masitinib mesylate, for the preparation of a medicament for the treatment of GIST, to the use of this therapy for the treatment of GIST, and a method of treating mammals, including humans, suffering from GIST by administering to said mammal in need of such treatment an effective dose of masitinib, and in particular masitinib mesylate.

7 Claims, 4 Drawing Sheets

FOREIGN PATENT DOCUMENTS

Figure 1:
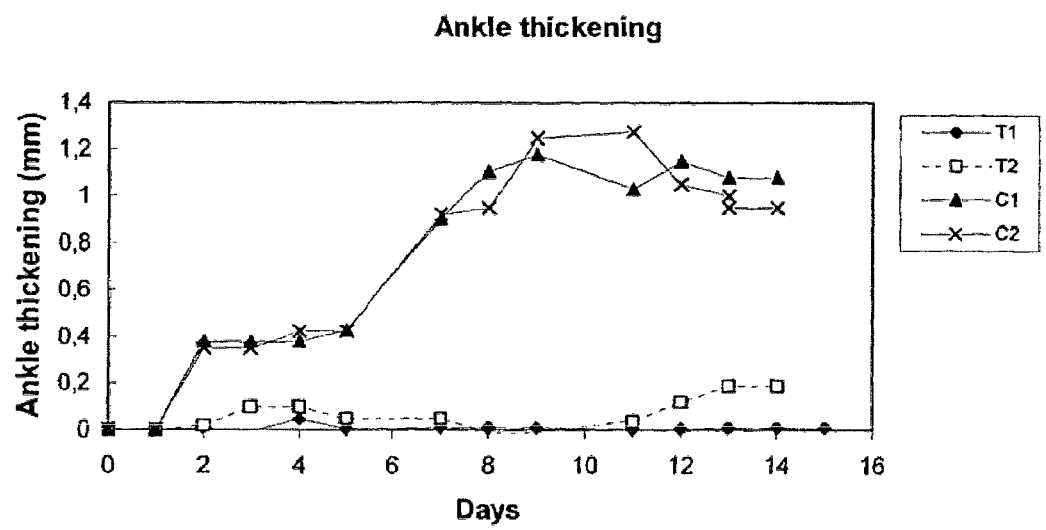

| WO | 91/15495 | 10/1991 |
|---|---|---|
| WO | 92/20642 | 11/1992 |
| WO | 92/21660 | 12/1992 |
| WO | 94/03427 | 2/1994 |
| WO | 94/14808 | 7/1994 |
| WO | 95/15758 | 6/1995 |
| WO | 96/01825 | 9/1996 |
| WO | 96/40116 | 12/1996 |
| WO | 99/03854 | 1/1999 |
| WO | 00/33842 | 5/2000 |
| WO | 00/38519 | 7/2000 |
| WO | 00/75120 | 12/2000 |
| WO | 01/64200 | 9/2001 |
| WO | 01/64674 | 9/2001 |
| WO | 02/080925 | 10/2002 |
| WO | 03/002105 | 1/2003 |
| WO | 03/002106 | 1/2003 |
| WO | 03/002107 | 1/2003 |
| WO | 03/002108 | 1/2003 |
| WO | 03/002109 | 1/2003 |
| WO | 03/002114 | 1/2003 |
| WO | 03/003004 | 1/2003 |
| WO | 03/003006 | 1/2003 |
| WO | 03/004006 | 1/2003 |
| WO | 03/004007 | 1/2003 |
| WO | 03/035049 | 5/2003 |
| WO | 03/035050 | 5/2003 |
| WO | 03/039550 | 5/2003 |
| WO | 03/062215 | 7/2003 |
| WO | 2008/098949 | 8/2008 |

OTHER PUBLICATIONS

Soria et al., "Phase 1 Dose-Escalation Study of Oral Tyrosine Kinase Inhibitor Masitinib in Advanced and/or Metastatic Solid Cancer," European Journal of Cancer, vol. 45 (2009) 2333-2341.*

U.S. Appl. No. 60/359,652, filed Feb. 27, 2002, Moussy et al.

U.S. Appl. No. 60/359,651, filed Feb. 27, 2002, Moussy et al.

Golub et al., Science, vol. 286, Oct. 15, 1999, pp. 531-537.

Schantl et al., Synthetic Communications, 1998, 29(8): 1451-1462.

Kim et al., "Inhibition of vascular endothelial growth factor-induced angiogenesis suppresses tumour grown in vivo", Nature, vol. 362, pp. 841-844, Apr. 29, 1993.

Nairn et al, "Solutions, Emulsions, Suspensions and Extractives", Remington's Pharmaceutical Sciences, 16th edition, pp. 1438-1462, 1980.

Dugard et al., "Effects of Ionic Surfactants on Permeability of Human Epidermis: An Electrometric Study", The Journal of Investigative Dermatology, vol. 60, No. 5, pp. 263-269, 1973.

Sekura et al., "The Percutaneous Absorption of Alkyl Methyl Sulfoxides", Pharmacology of the Skin, Advances in Biology of Skin, vol. 60, pp. 257-269, 1972.

Cooper et al., "Interaction of Surfactants with Epidermal Tissues: Physicochemical Aspects", Surfactant Science Series, vol. 16, pp. 195-210, 1987.

Beslu et al., "Phosphatidylinositol-3$^1$ Kinase is Not Required for Mitogenesis or Internalization of the Flt3/Flk2 Receptor Tyrosine Kinase", The Journal of Biological Chemistry, vol. 271, No. 33, pp. 20075-20081, Aug. 16, 1996.

Rottapel et al., "The Steel/W Transduction Pathway: Kit Autophosphorylation and Its Association with a Unique Subset of Cytoplasmic Signaling Proteins is induced by the Steel Factor", Molecular and Cellular Biology, vol. 11, No. 6, pp. 3043-3051, Jun. 1991.

Choi et al., "Correlation of Computed Tomography and Positron Emission Tomography in Patients With Metastatic Gastrointestinal Stromal Tumor Treated at a Single Institution With Imatinib Meylate: Proposal of New Computer Tomography Response Criteria", Journal of Clinical Oncology, vol. 25, No. 13, May 1, 2007, pp. 1753-1759.

Darzynkiewicz et al., "Features of Apoptotic Cells Measured by Flow Cytometry", Cyometry, 13:795-808 (1992).

Therasse et al., "New Guidelines to Evaluate the Response to Treatment in Solid Tumors", Journal of the National Cancer Institute, vol. 92, No. 3, Feb. 2, 2000, pp. 205-216.

Jager et al., "Imatinib mesylate for the treatment of gastrointestinal stromal tumours: best monitored with FDG PET", Nuclear Medicine Communications, 2004, vol. 25, No. 5, pp. 433-438.

Demetri et al., "Efficacy and Safety of Imatinib Mesylate in Advanced Gastrointestinal Stromal Tumors", N Engl J Med, vol. 347, No. 7, Aug. 15, 2002, pp. 472-480.

Verweij et al., "Progression-free survival in gastrointestinal stromal tumours with high-dose imatinib: randomized trial", The Lancet, vol. 364, Sep. 25, 2004, pp. 1127-1134.

Blanke et al., Phase III Randomized, Intergroup Trial Assessing Imatinib Mesylate at Two Dose Levels in Patients With Unresectable or Metastatic Gastrointestinal Stromal Tumors Expressing the Kit Receptor Tyrosine Kinase: S0033, Journal of Clinical Oncology, vol. 26, No. 4, Feb. 1, 2008, pp. 626-632.

Blay et al., "Prospective Multicentric Randomized Phase III Study of Imatinib in Patients With Advanced Gastrointestinal Stromal Tumors Comparing Interruption Versus Continuation of Treatment Beyond 1 Year: The French Sarcoma Group", Journal of Clinical Oncology, vol. 25, No. 9, Mar. 20, 2007, pp. 1107-1113.

Heinrich et al., "Molecular Correlates of Imatinib Resistance in Gastrointestinal Stromal Tumors", Journal of Clinical Oncology, vol. 24, No. 29, Oct. 10, 2006, pp. 4764-4774.

Van Glabbeke et al., "Initial and Late Resistance to Imatinib in Advanced Gastrointestinal Stromal Tumors Are Predicted by Different Prognostic Factors: A European Organisation for Research and Treatment of Cancer—Italian Sarcoma Group—Australasian Gastrointestinal Trials Group Study", Journal of Clinical Oncology, vol. 23, No. 24, Aug. 20, 2005, pp. 5795-5803.

Blay et al., "Consensus meeting for the management of gastrointestinal stromal tumors, Report of the GIST Consensus Conference of Mar. 20-21, 2004, under the auspices of ESMO", Annals of Oncology 16: 566-578, 2005.

Debeic-Rychter et al., "KIT mutations and dose selection for imatinib in patients with advanced gastrointestinal stromal tumors", European Journal of Cancer 42 (2006) 1093-1103.

Van Glabbeke et al., "Comparison of two doses of imatinib for the treatment of unresectable or metastatic gastrointestinal stromal tumors (GIST): A meta-analysis based on 1,640 patents (pts).", American Society of Clinical Oncology, 2007 ASCO Annual Meeting Proceedings Part 1. vol. 25, No. 18S (Jun. 20 Supplement), 2007: 10004.

Zalcberg et al., "Outcome of patients with advanced gastro-intestinal stromal tumours crossing over to a daily imatinib dose of 800 mg after progression on 400 mg", European Journal of Cancer 41 (2005) 1751-1757.

Soria et al., "Phase 1 dose-escalation study of oral tyrosine kinase inhibitor masitinib in advanced and/or metastatic solid cancers", European Journal of Cancer 45 (2009) 2333-2341.

Tebib et al., "Masitinib in the treatment of active rheumatoid arthritis: results of a multicentre, open-label, dose-ranging, phase 2a study", Arthritis Research & Therapy, 2009, vol. 11, No. 3, pp. 1-12.

Van Glabbeke et al., "Predicting toxicities for patients with advanced gastrointestinal stromal tumours treated with imatinib: A study of the European Organisation for Research and Treatment of Cancer, the Italian Sarcoma Group, and the Australasian Gastro-Intestinal Trials Group", European Journal of Cancer 42 (9006) 2277-2285.

Lassau et al., "Gastrointestinal Stromal Tumors Treated with Imatinib: Monitoring Response with Contrast-Enhanced Sonography", Gastrointestinal Imaging, Nov. 2006, pp. 1267-1273.

Prior et al., "Early Prediction of Response to Sunitinib After Imatinib Failure by $^{18}$F-Flourodeoxyglucose Positron Emission Tomography in Patients With Gastrointestinal Stromal Tumor", Journal of Clinical Oncology, vol. 27, No. 3, Jan. 20, 2009 pp. 439-445.

Van Den Abbeele et al., "Use of positron emission tomography in oncology and its potential role to assess response to imatinib mesylate therapy in gastrointestinal stromal tumors (GISTs)", European Journal of Cancer, vol. 38 Suppl. 5 (2002) S60-S65.

Chami et al., "Quantitative functional imaging by dynamic contrast enhanced ultrsonography (DCE-US) in patients with GIST treated by thyrosine kinase inhibitor (TKI)", J Clin Oncol 26: 2008 (May 20 suppl; abstr 10552).

Benjamin et al., "We Should Desist Using RECIST, at Least in GIST", Journal of Clinical Oncology, vol. 25, No. 13, May 1, 2007, pp. 1760-1764.

Le Cesne et al., "Absence of Progression as Assessed by Response Evaluation Criteria in Solid Tumors Predicts Survival in Advanced GI Stromal Tumors Treated With Imatinib Mesylate: The Intergroup EORTC-ISG-AGITG Phase III Trial", Journal of Clinical Oncology, vol. 27, No. 24, Aug. 20, 2009 pp. 3969-3974.

Demetri et al., "Efficacy and safety of sunitinib in patients with advanced gastrointestinal stromal tumour after failure of imatinib: a radomised controlled trial", The Lancet, vol. 368, Oct. 14, 2006, pp. 1329-1337.

Siesser et al., "The Signaling and Biological Implications of FAK Overexpression in Cancer", Clinical Cancer Research, Jun. 1, 2006, pp. 3233-3237.

Kindblom et al., "Gastrointestinal Pacemaker Cell Tumor (GIPACT), Gastrointestinal Stromal Tumors Show Phenotypic Characteristics of the Interstitial Cells of Cajal", American Journal of Pathology, vol. 152, No. 5, May 1998, pp. 1259-1269.

Hirota et al. "Gain-of-Function Mutations of c-kit in Human Gastrointestinal Stromal Tumors" Science, vol. 279, Jan. 23, 1998, pp. 577-580.

Heinrich et al., "PDGFRA Activating Mutations in Gastrointestinal Stromal Tumors", Science, Jan. 31, 2003, vol. 299, pp. 708-710.

Sleijfer et al., "Improved Insight into Resistance Mechanisms to Imatinib in Gastrointestinal Stromal Tumors: A Basis for Novel Approaches and Individualization of Treatment", The Oncologist, 2007; 12: 719-726.

Blanke et al., "Long-Term Results From a Randomized Phase II Trial of Standard-Versus Higher-Dose Imatinib Mesylate for Patients With Unresectable or Metastatic Gastrointestinal Stromal Tumors Expressing KIT", Journal of Clinical Oncology, vol. 26, No. 4, Feb. 1, 2008, pp. 620-625.

Demetri et al., "Imatinib Plasma Levels Are Correlated With Clinical Benefit in Patients With Unresectable/Metastatic Gastrointestinal Stromal Tumors", Journal of Clinical Oncology, vol. 27, No. 19, Jul. 1, 2009, pp. 3141-3147.

Dubreuil et al., "Masitinib (AB1010), a Potent and Selective Tyrosine Kinase Inhibitor Targeting KIT", PLoS ONE, Sep. 2009, vol. 4, Issue 9, pp. 1-12.

\* cited by examiner

2-(3-AMINOARYL) AMINO-4-ARYL-THIAZOLES AND THEIR USE AS C-KIT INHIBITORS

CROSS-REFERENCE TO RELATED APPLICATIONS

This application claims the benefit of U.S. Provisional Application No. 61/298,953 filed on Jan. 28, 2010. This application is a continuation-in-part of U.S. patent application Ser. No. 11/779,633 filed on Jul. 18, 2007 which is a continuation of U.S. patent application Ser. No. 10/523,018 filed on Feb. 2, 2005, which is a national stage of PCT/IB03/03685 filed under 35 U.S.C. §371 on Jul. 31, 2003, which claims the benefit of U.S. Provisional Application No. 60/400,064 filed on Aug. 2, 2002, the complete disclosures of which are incorporated into this application by reference. This application also claims the benefit of U.S. patent application Ser. No. 10/632,101 filed Aug. 1, 2003, which claims the benefit of U.S. Provisional Application No. 60/400,064 filed on Aug. 2, 2002.

DESCRIPTION OF THE INVENTION

The present invention relates to novel compounds selected from 2-(3-aminoaryl)amino-4-aryl-thiazoles that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit inhibitors.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Other tyrosine kinases are the well-known VEGF receptors (Kim et al., Nature 362, pp. 841-844, 1993), PDGF receptors, c-kit and the FLK family. These receptors can transmit signals to other tyrosine kinases including Src, Raf, Frk, Btk, Csk, Abl, Fes/Fps, Fak, Jak, Ack. etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, U.S. 60/359,652 and U.S. 60/359,651.

It was found that mast cells present in tissues of patients are implicated in or contribute to the genesis of diseases such as autoimmune diseases (rheumatoid arthritis, inflammatory bowel diseases (IBD)) allergic diseases, tumor angiogenesis, inflammatory diseases, and interstitial cystitis. In these diseases, it has been shown that mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor also can be constitutively activated by mutations leading to abnormal cell proliferation and development of diseases such as mastocytosis and various cancers.

For this reason, it has been proposed to target c-kit to deplete the mast cells responsible for these disorders.

The main objective underlying the present invention is therefore to find potent and selective compounds capable of inhibiting wild type and/or mutated c-kit.

Many different compounds have been described as tyrosine kinase inhibitors, for example, bis monocyclic, bicyclic or heterocyclic aryl compounds (WO 92/20642), vinylene-azaindole derivatives (WO 94/14808) and 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), selenoindoles and selenides (WO 94/03427), tricyclic polyhydroxylic compounds (WO 92/21660) and benzylphosphonic acid compounds (WO 91/15495), pyrimidine derivatives (U.S. Pat. No. 5,521,184 and WO 99/03854), indolinone derivatives and pyrrole-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as his monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940) and aryl and heteroaryl quinazoline (U.S. Pat. No. 5,721,237, U.S. Pat. No. 5,714,493, U.S. Pat. No. 5,710,158 and WO 95/15758).

However, none of these compounds have been described as potent and selective inhibitors of c-kit or of the c-kit pathway.

In connection with the present invention, we have found that compounds corresponding to the 2-(3-aminoaryl)amino-4-aryl-thiazoles are potent and selective inhibitors of c-kit or c-kit pathway. These compounds are good candidates for treating diseases such as autoimmunes diseases, inflammatory diseases, cancer and mastocytosis.

DESCRIPTION

Therefore, the present invention relates to compounds belonging to the 2-(3-amino)arylamino-4-aryl-thiazoles. These compounds are capable of selectively inhibiting signal transduction involving the tyrosine phosphokinase c-kit and mutant forms thereof.

In a first embodiment, the invention is aimed at compounds of formula I, which may represent either free base forms of the substances or pharmaceutically acceptable salts thereof:

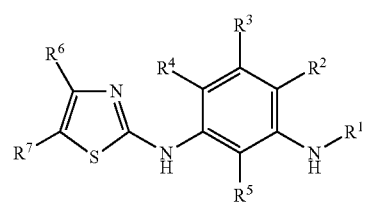

FORMULA I and wherein $R^1$ is:
a) a linear or branched alkyl group containing from 1 to 10 carbon atoms optionally substituted with at least one heteroatom, notably a halogen selected from I, Cl, Br and F, and/or bearing a pendant basic nitrogen functionality;
b) an aryl or heteroaryl group optionally substituted by an alkyl or aryl group optionally substituted with a heteroatom, notably a halogen selected from I, Cl, Br and F or bearing a pendant basic nitrogen functionality;
c) a —CO—NH—R, —CO—R, —CO—OR or a —CO—NRR' group, wherein R and R' are independently chosen from H or an aryl, heteroaryl, alkyl and cycloalkyl group optionally substituted with at least one heteroatom, notably a halogen selected from I, Cl, Br and F, and/or bearing a pendant basic nitrogen functionality;
$R^2$ is hydrogen, halogen or a linear or branched alkyl group containing from 1 to 10 carbon atoms, trifluoromethyl or alkoxy;
$R^3$ is hydrogen, halogen or a linear or branched alkyl group containing from 1 to 10 carbon atoms, trifluoromethyl or alkoxy;
$R^4$ is hydrogen, halogen or a linear or branched alkyl group containing from 1 to 10 carbon atoms, trifluoromethyl or alkoxy;
$R^5$ is hydrogen, halogen or a linear or branched alkyl group containing from 1 to 10 carbon atoms, trifluoromethyl or alkoxy;
$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy,
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality;
and $R^7$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality;

In another preferred embodiment, when $R^1$ has the meaning depicted in c) above, the invention is directed to compounds of the following formula:

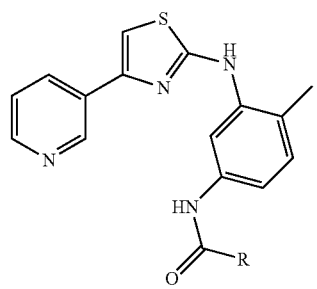

wherein R is H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted by an alkyl, a cycloalkyl, an aryl or heteroaryl group optionally substituted with a heteroatom, notably a halogen selected from I, Cl, Br and F and/or bearing a pendant basic nitrogen functionality.

Among the particular compounds in which R1 has the meaning as depicted in c) above, the invention is directed to amide-aniline compounds of the following formula:

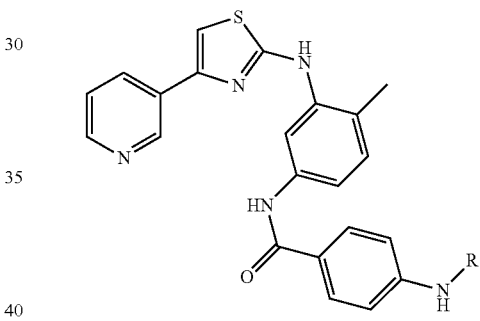

wherein R is H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted with a heteroatom, notably a halogen selected from I, Cl, Br and F and/or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F and/or bearing a pendant basic nitrogen functionality;
a —SO2-R group wherein R is an alkyl, cycloalkyl, aryl or heteroaryl optionally substituted with an heteroatom, notably a halogen selected from I, Cl, Br and F and/or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Among the particular compounds in which R1 has the meaning as depicted in c) above, the invention is directed to amide-benzylamine compounds of the following formula:

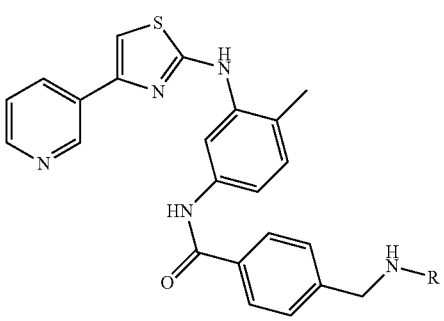

wherein R is H or an organic group that can be selected for example from a linear or branched alkyl group containing from 1 to 10 carbon atoms optionally substituted with at least one heteroatom, notably a halogen selected from I, Cl, Br and F, and/or bearing a pendant basic nitrogen functionality; a cycloalkyl, aryl or heteroaryl group optionally substituted with an heteroatom, notably a halogen selected from I, Cl, Br and F or bearing a pendant basic nitrogen functionality; or an alkyl, cycloalkyl, aryl or heteroaryl group substituted by a alkyl, cycloalkyl, aryl or heteroaryl group optionally substituted with a heteroatom, notably a halogen selected from I, Cl, Br and F or bearing a pendant basic nitrogen functionality; a —SO2-R group wherein R is an alkyl, cycloalkyl, aryl or heteroaryl group optionally substituted with an heteroatom, notably a halogen selected from I, Cl, Br and F or bearing a pendant basic nitrogen functionality; or a —CO—R or a —CO—NRR' group, wherein R and R' are independently chosen from H or an aryl heteroaryl, alkyl and cycloalkyl group optionally substituted with at least one heteroatom and/or bearing a pendant basic nitrogen functionality.

Among the particular compounds in which R1 has the meaning as depicted in c) above, the invention is directed to amide-phenol compounds of the following formula:

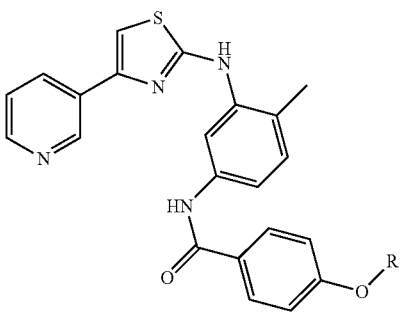

wherein R is H or an organic group that can be selected for example from a linear or branched alkyl group containing from 1 to 10 carbon atoms optionally substituted with at least one heteroatom, notably a halogen selected from I, Cl, Br and F, and/or bearing a pendant basic nitrogen functionality; a cycloalkyl, aryl or heteroaryl group optionally substituted with a heteroatom, notably a halogen selected from I, Cl, Br and F and/or bearing a pendant basic nitrogen functionality; or an alkyl, cycloalkyl, aryl or heteroaryl group substituted by a alkyl, cycloalkyl, aryl or heteroaryl group optionally substituted with a heteroatom, notably a halogen selected from I, Cl, Br and F and/or bearing a pendant basic nitrogen functionality;
a —SO2-R group wherein R is an alkyl, cycloalkyl, aryl or heteroaryl group optionally substituted with an heteroatom, notably a halogen selected from I, Cl, Br and F and/or bearing a pendant basic nitrogen functionality; or a —CO—R or a —CO—NRR' group, wherein R and R' are independently chosen from H or an aryl, heteroaryl, alkyl and cycloalkyl group optionally substituted with at least one heteroatom and/or bearing a pendant basic nitrogen functionality Among the particular compounds in which R1 has the meaning as depicted in c) above, the invention is directed to urea compounds of the following formula:

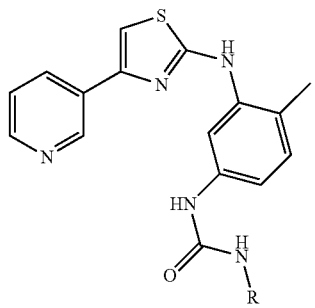

wherein R is H or an organic group that can be selected for example from a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality.

Among the particular compounds in which R1 has the meaning as depicted in a) and b) above, the invention is directed to N-Aminoalkyl-N'-thiazol-2-yl-benzene-1,3-diamine compounds of the following formula:

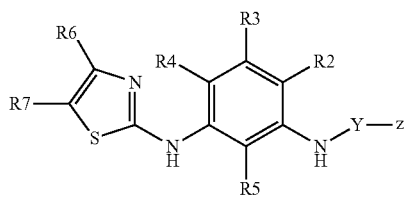

wherein Y is a linear or branched alkyl group containing from 1 to 10 carbon atoms;
wherein Z represents an aryl or heteroaryl group, optionally substituted at one or more ring position with any permutation of the following groups:
  a halogen such as F, Cl, Br, I;
  a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an O—R, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NRaRb, where Ra and Rb represents a hydrogen, or a linear or branched alkyl group containing from 1 to 10 carbon atoms optionally substituted with at least one heteroatom (for example a halogen) and/or bearing a pendant basic nitrogen functionality or a cycle; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a COOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CONRaRb, where Ra and Rb are a hydrogen or a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCONRaRb, where Ra and Rb are a hydrogen or a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $NRaOSO_2Rb$, where Ra and Rb are a linear or branched alkyl group containing from 1 to 10 carbon atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

$R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is hydrogen, halogen or a linear or branched alkyl group containing from 1 to 10 carbon atoms, trifluoromethyl or alkoxy;

R⁵ is hydrogen, halogen or a linear or branched alkyl group containing from 1 to 10 carbon atoms, trifluoromethyl or alkoxy;
R⁶ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality;
and R⁷ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, an halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

An example of preferred compounds of the above formula is depicted below:

001: 4-{[4-Methyl-3-(4-pyridin-3-yl-thiazol-2-ylamino)-phenylamino]-methyl}-benzoic acid methyl ester

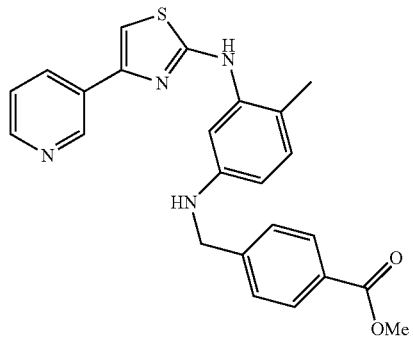 [SMILES: COC(=O)c1ccc(CNc2ccc(C)c(Nc3nc(-c4cccnc4)cs3)c2)cc1]

Among the compounds of formula I, the invention is particularly embodied by the compounds of the following formula II:

FORMULA II

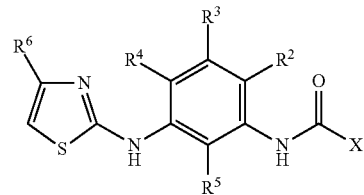

wherein X is R or NRR' and wherein R and R' are independently chosen from H, an aryl, a heteroaryl, an alkyl, or a cycloalkyl group optionally substituted with at least one heteroatom, such as for example a halogen chosen from F, I, Cl and Br and optionally bearing a pendant basic nitrogen functionality; or an aryl, a heteroaryl, an alkyl or a cycloalkyl group substituted with an aryl, a heteroaryl, an alkyl or a cycloalkyl group optionally substituted with at least one heteroatom, such as for example a halogen chosen from F, I, Cl and Br and optionally bearing a pendant basic nitrogen functionality,
R² is hydrogen, halogen or a linear or branched alkyl group containing from 1 to 10 carbon atoms, trifluoromethyl or alkoxy;
R³ is hydrogen, halogen or a linear or branched alkyl group containing from 1 to 10 carbon atoms, trifluoromethyl or alkoxy;
R⁴ is hydrogen, halogen or a linear or branched alkyl group containing from 1 to 10 carbon atoms, trifluoromethyl or alkoxy;
R⁵ is hydrogen, halogen or a linear or branched alkyl group containing from 1 to 10 carbon atoms, trifluoromethyl or alkoxy;
R⁶ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

In another alternative, substituent R6, which in the formula II is connected to position 4 of the thiazole ring, may instead occupy position 5 of the thiazole ring.

Among the preferred compounds corresponding formula II, the invention is directed to compounds in which X is a substituted alkyl, aryl or heteroaryl group bearing a pendant basic nitrogen functionality represented for example by the structures a to f shown below, wherein the wavy line corresponds to the point of attachment to core structure of formula II:

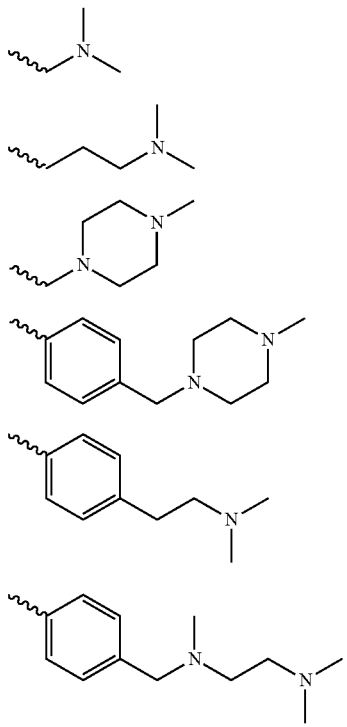

Among group a to f, X (see formula II) is preferentially group d.

Furthermore, among the preferred compounds of formula I or II, the invention concerns the compounds in which $R^2$ and $R^3$ are hydrogen. Preferentially, $R^4$ is a methyl group and $R^5$ is H. In addition, $R^6$ is preferentially a 3-pyridyl group (cf. structure g below), or a 4-pyridyl group (cf. structure h below). The wavy line in structure g and h correspond to the point of attachment to the core structure of formula I or II.

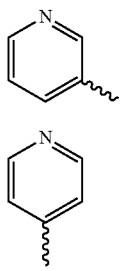

Thus, the invention contemplates:
1—A compound of formula II as depicted above, wherein X is group d and $R^6$ is a 3-pyridyl group.
2—A compound of formula II as depicted above, wherein X is group d and $R^4$ is a methyl group.
3—A compound of formula I or II as depicted above, wherein $R^1$ is group d and $R^2$ is H.
4—A compound of formula I or II as depicted above, wherein $R^1$ is group d and $R^3$ is H.
5—A compound of formula I or II as depicted above, wherein $R^1$ is group d and $R^2$ and/or $R^3$ and/or $R^5$ is H.
6—A compound of formula I or II as depicted above, wherein $R^6$ is a 3-pyridyl group and $R^3$ is a methyl group.
7—A compound of formula I or II as depicted above, wherein $R^6$ is a 3-pyridyl group and $R^2$ is H.
8—A compound of formula I or II as depicted above, wherein $R^2$ and/or $R^3$ and/or $R^5$ is H and $R^4$ is a methyl group.
9—A compound of formula I or II as depicted above wherein $R^2$ and/or $R^3$ and/or $R^5$ is H, $R^4$ is a methyl group and $R^6$ is a 3-pyridyl group.

Among the compounds of formula II, the invention is particularly embodied by the compounds wherein $R^2$, $R^3$, $R^5$ are hydrogen, corresponding to the following formula II-1:

FORMULA II-1

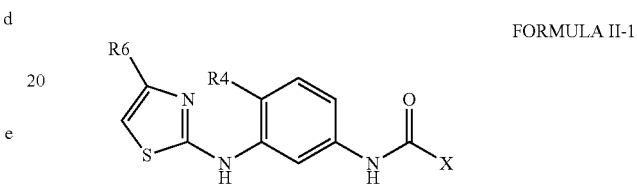

wherein X is R or NRR' and wherein R and R' are independently chosen from H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted with an heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a —SO2-R group wherein R is an alkyl, cycloalkyl, aryl or heteroaryl optionally substituted with a heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

$R^4$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;
(iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

In another alternative, substituent R6, which in the formula II is connected to position 4 of the thiazole ring, may instead occupy position 5 of the thiazole ring.

Examples

002: 2-(2-methyl-5-amino)phenyl-4-(3-pyridyl)-thiazole

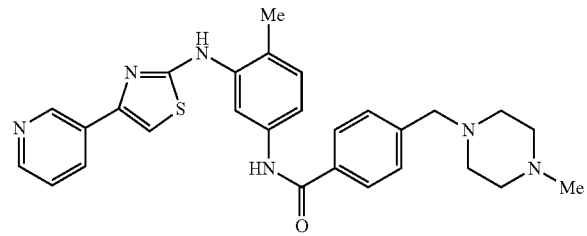 [SMILES: Cc1ccc(NC(=O)c2ccc(CN3CCN(C)CC3)cc2)cc1Nc1nc(-c2cccnc2)cs1]

003: 4-(4-Methyl-piperazin-1-ylmethyl)-N-[3-(4-pyridin-3-yl-thiazol-2-ylamino)-phenyl]-benzamide

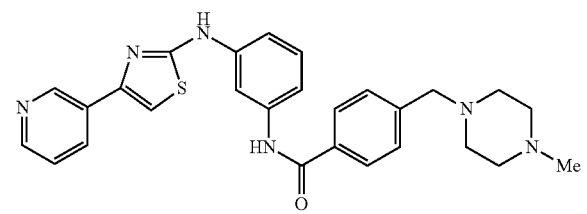 [SMILES: CN1CCN(Cc2ccc(C(=O)Nc3cccc(Nc4nc(-c5cccnc5)cs4)c3)cc2)CC1]

004: N-[4-Methyl-3-(4-phenyl-thiazol-2-ylamino)-phenyl]-4-(4-methyl-piperazin-1-ylmethyl)-benzamide

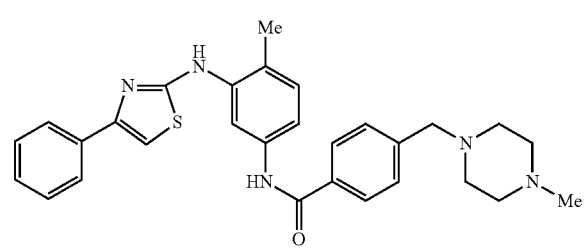 [SMILES: Cc1ccc(NC(=O)c2ccc(CN3CCN(C)CC3)cc2)cc1Nc1nc(-c2ccccc2)cs1]

005: N-[3-([2,4']Bithiazolyl-2'-ylamino)-4-methyl-phenyl]-4-(4-methyl-piperazin-1-ylmethyl)-benzamide

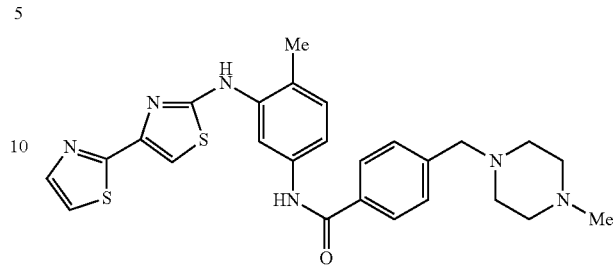

006: 4-(4-Methyl-piperazin-1-ylmethyl)-N-[4-methyl-3-(4-pyrazin-2-yl-thiazol-2-ylamino)-phenyl]-benzamide

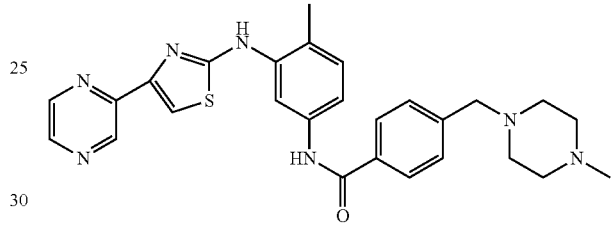

007: 2-[5-(3-Iodo-benzoylamino)-2-methyl-phenylamino]-thiazole-4-carboxylic acid ethyl ester

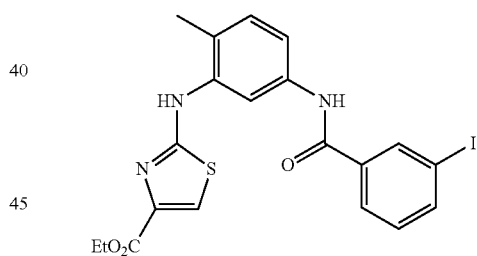

008: 2-{2-Methyl-5-[4-(4-methyl-piperazin-1-ylmethyl)-benzoylamino]-phenylamino}-thiazole-4-carboxylic acid ethyl ester

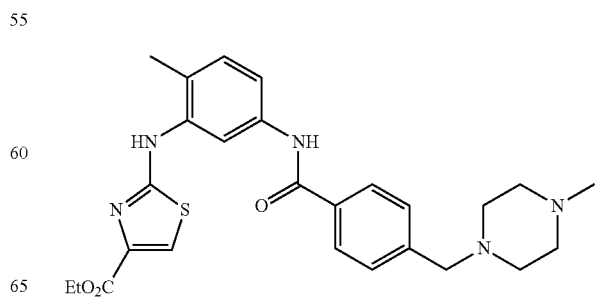

027: 2-(2-chloro-5-amino)phenyl-4-(3-pyridyl)-thiazole

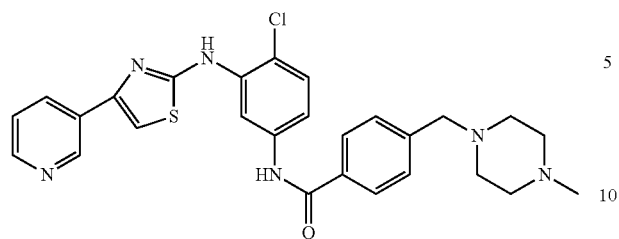

128: 3-Bromo-N-{3-[4-(4-chloro-phenyl)-5-methyl-thiazol-2-ylamino]-4-methyl-phenyl}-benzamide

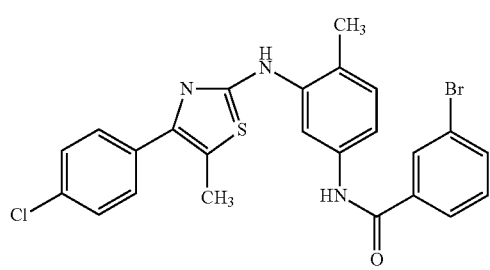

129: {3-[4-(4-Chloro-phenyl)-5-methyl-thiazol-2-ylamino]-4-methyl-phenyl}-carbamic acid isobutyl ester

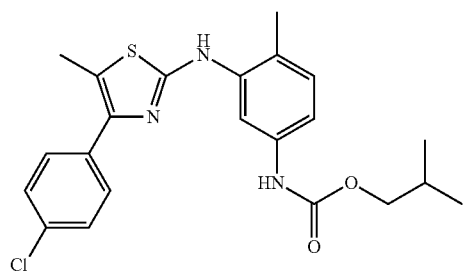 [SMILES: Cc1ccc(NC(=O)OCC(C)C)cc1Nc1nc(-c2ccc(Cl)cc2)c(C)s1]

130: 2-[5-(3-Bromo-benzoylamino)-2-methyl-phenylamino]-5-(4-chloro-phenyl)-thiazole-4-carboxylic acid ethyl ester

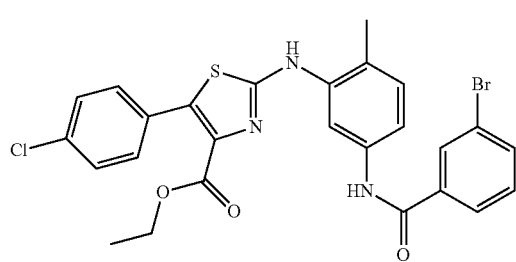 [SMILES: CCOC(=O)c1nc(Nc2cc(NC(=O)c3cccc(Br)c3)ccc2C)sc1-c1ccc(Cl)cc1]

131: 2-[5-(3-Bromo-benzoylamino)-2-methyl-phenylamino]-5-(4-chloro-phenyl)-thiazole-4-carboxylic acid (2-dimethylamino-ethyl)-amide

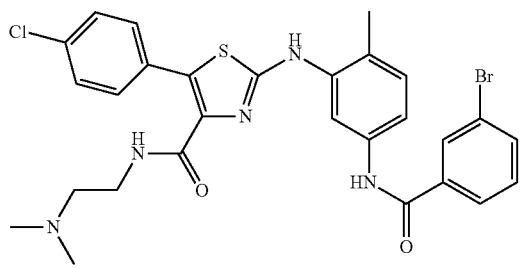 [SMILES: Cc1ccc(NC(=O)c2cccc(Br)c2)cc1Nc1nc(C(=O)NCCN(C)C)c(-c2ccc(Cl)cc2)s1]

110: N-{3-[4-(4-Methoxy-phenyl)-thiazol-2-ylamino]-4-methyl-phenyl}-4-(4-methyl-piperazin-1-ylmethyl)-benzamide

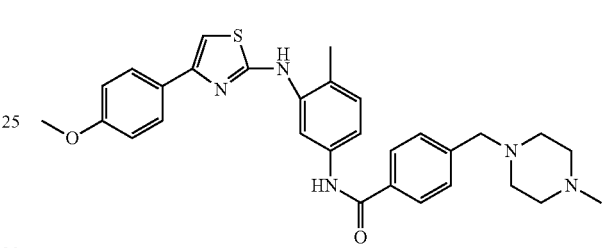

116: 4-(4-Methyl-piperazin-1-ylmethyl)-N-{4-methyl-3-[4-(3-trifluoromethyl-phenyl)-thiazol-2-ylamino]-phenyl}-benzamide 117: N-{4-Methyl-3-[4-(3-nitro-phenyl)-thiazol-2-ylamino]-phenyl}-4-(4-methyl-piperazin-1-ylmethyl)-benzamide

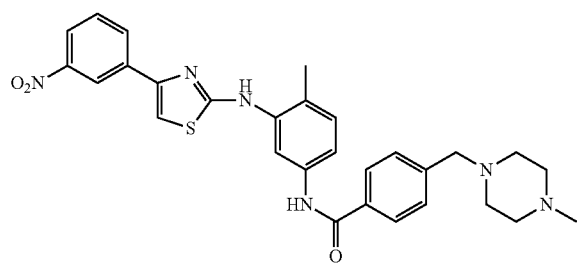 [SMILES: Cc1ccc(NC(=O)c2ccc(CN3CCN(C)CC3)cc2)cc1Nc1nc(-c2cccc([N+](=O)[O-])c2)cs1]

124: N-{3-[4-(2,5-Dimethyl-phenyl)-thiazol-2-ylamino]-4-methyl-phenyl}-4-(4-methyl-piperazin-1-ylmethyl)-benzamide

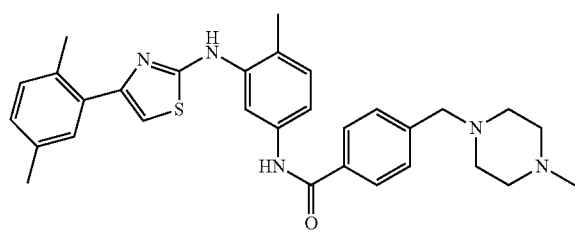 [SMILES: Cc1ccc(C)c(-c2csc(Nc3cc(NC(=O)c4ccc(CN5CCN(C)CC5)cc4)ccc3C)n2)c1]

108: N-{3-[4-(4-Chloro-phenyl)-thiazol-2-ylamino]-4-methyl-phenyl}-4-(4-methyl-piperazin-1-ylmethyl)-benzamide

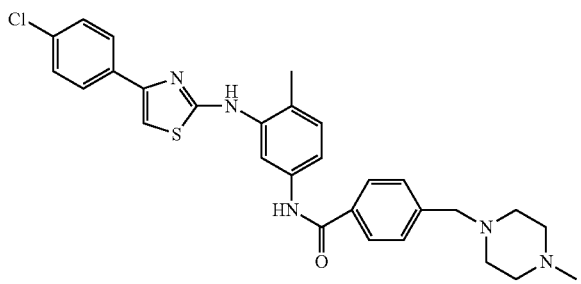 [SMILES: Cc1ccc(NC(=O)c2ccc(CN3CCN(C)CC3)cc2)cc1Nc1nc(-c2ccc(Cl)cc2)cs1]

113: N-{3-[4-(3-Methoxy-phenyl)-thiazol-2-ylamino]-4-methyl-phenyl}-4-(4-methyl-piperazin-1-ylmethyl)-benzamide

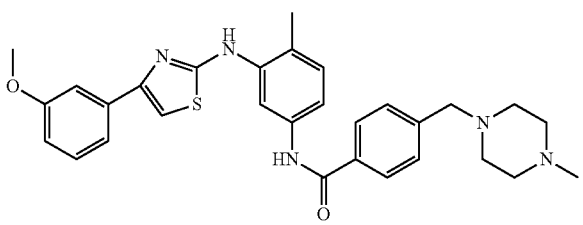 [SMILES: COc1cccc(-c2csc(Nc3cc(NC(=O)c4ccc(CN5CCN(C)CC5)cc4)ccc3C)n2)c1]

063: N-[4-Methyl-3-(4-pyridin-3-yl-thiazol-2-ylamino)-phenyl]-isonicotinamide

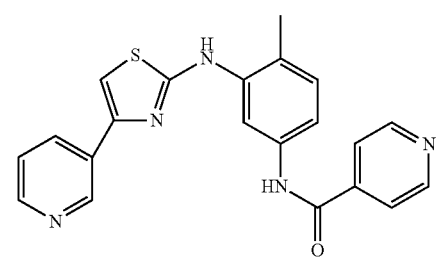 [SMILES: Cc1ccc(NC(=O)c2ccncc2)cc1Nc1nc(-c2cccnc2)cs1]

064: 2,6-Dichloro-N-[4-methyl-3-(4-pyridin-3-yl-thiazol-2-ylamino)-phenyl]-isonicotinamide

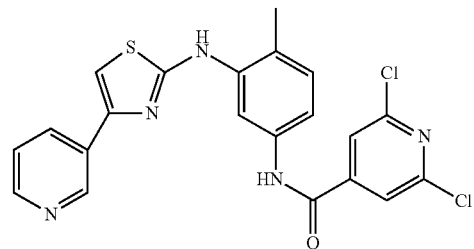 [SMILES: Cc1ccc(NC(=O)c2cc(Cl)nc(Cl)c2)cc1Nc1nc(-c2cccnc2)cs1]

091: 3-Phenyl-propynoic acid [4-methyl-3-(4-pyridin-3-yl-thiazol-2-ylamino)-phenyl]-amide

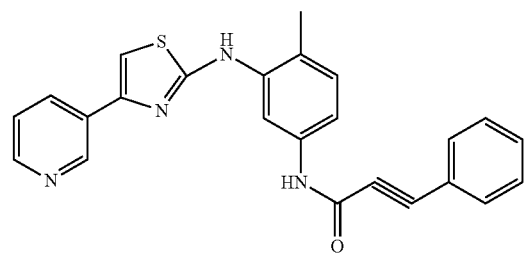 [SMILES: Cc1ccc(NC(=O)C#Cc2ccccc2)cc1Nc1nc(-c2cccnc2)cs1]

092: Cyclohexanecarboxylic acid [4-methyl-3-(4-pyridin-3-yl-thiazol-2-ylmethyl)-phenyl]-amide

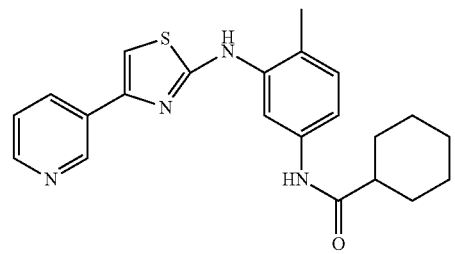 [SMILES: Cc1ccc(NC(=O)C2CCCCC2)cc1Nc1nc(-c2cccnc2)cs1]

093: 5-[4-Methyl-3-(4-pyridin-3-yl-thiazol-2-ylamino)-phenylcarbamoyl]-pentanoic acid ethyl ester

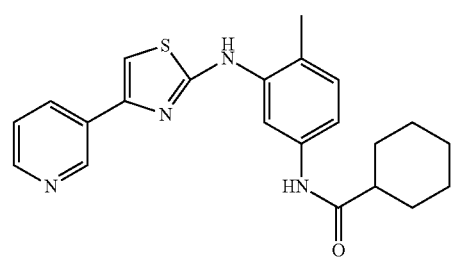 [SMILES: Cc1ccc(NC(=O)C2CCCCC2)cc1Nc1nc(-c2cccnc2)cs1]

094: 1-Methyl-cyclohexanecarboxylic acid [4-methyl-3-(4-pyridin-3-yl-thiazol-2-ylmethyl)-phenyl]-amide

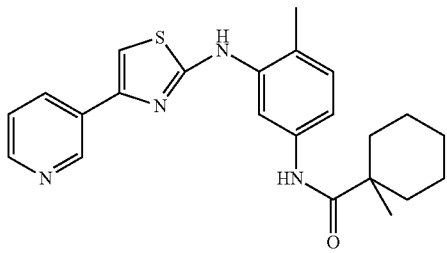 [SMILES: Cc1ccc(NC(=O)C2(C)CCCCC2)cc1Nc1nc(-c2cccnc2)cs1]

095: 4-tert-Butyl-cyclohexanecarboxylic acid [4-methyl-3-(4-pyridin-3-yl-thiazol-2-ylamino)-phenyl]-amide

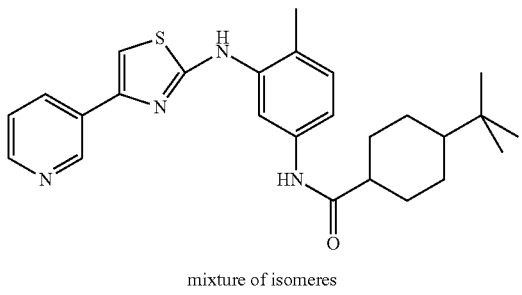

mixture of isomeres
cis/trans

096: N-[4-Methyl-3-(4-pyridin-3-yl-thiazol-2-ylamino)-phenyl]-4-morpholin-4-yl-butyramide

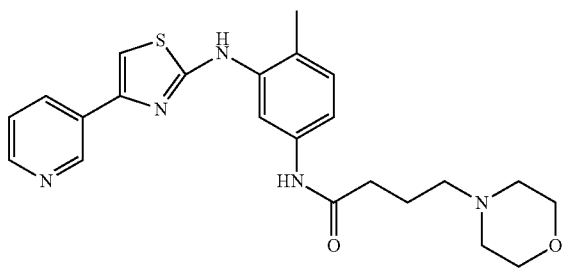 [SMILES: Cc1ccc(NC(=O)CCCN2CCOCC2)cc1Nc1nc(-c2cccnc2)cs1]

beige powder mp: 116-120° C.

$^1$H NMR (DMSO-d$^6$) δ=1.80-2.00 (m, 2H); 2.29 (s, 3H); 2.30-2.45 (m, 6H); 3.55-3.65 (m, 6H); 7.15-7.25 (m, 2H); 7.46-7.50 (m, 2H); 7.52 (s, 1H); 8.35 (d, J=6.2 Hz, 1H); 8.55 (dd, J=1.5 Hz, J=4.7 Hz, 2H); 9.22 (s, 1H); 9.45 (s, 1H); 9.93 (s, 1H)

Among the compounds of formula II, the invention is particularly embodied by the compounds wherein X is a urea group, a —CO—NRR' group, corresponding to the [3-(thiazol-2-ylamino)-phenyl]-urea family and the following formula II-2:

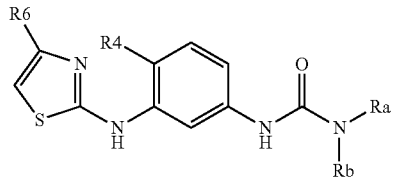

FORMULA II-2 wherein Ra, Rb are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F or bearing a pendant basic nitrogen functionality; a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, or bearing a pendant basic nitrogen functionality.

R$^4$ is hydrogen, halogen or a linear or branched alkyl group containing from 1 to 10 carbon atoms, trifluoromethyl or alkoxy;

R$^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

Examples

009: 1-(4-Methoxy-phenyl)-3-[4-methyl-3-(4-pyridin-3-yl-thiazol-2-ylamino)-phenyl]-urea

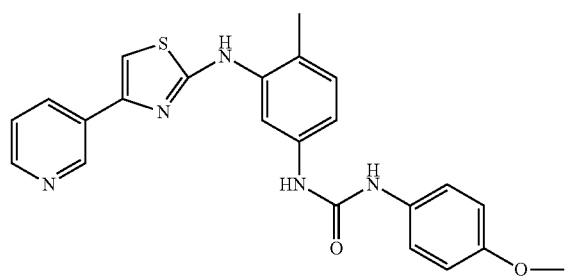 [SMILES: COc1ccc(NC(=O)Nc2ccc(C)c(Nc3nc(-c4cccnc4)cs3)c2)cc1]

010: 1-(4-Bromo-phenyl)-3-[4-methyl-3-(4-pyridin-3-yl-thiazol-2-ylamino)-phenyl]-urea

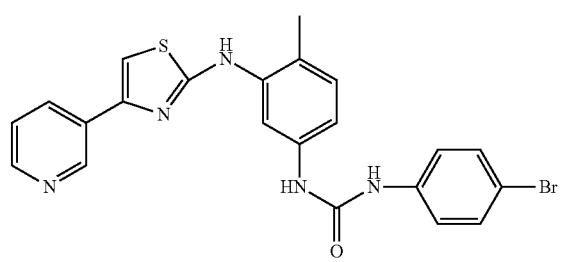 [SMILES: Cc1ccc(NC(=O)Nc2ccc(Br)cc2)cc1Nc1nc(-c2cccnc2)cs1]

011: 1-[4-Methyl-3-(4-pyridin-3-yl-thiazol-2-ylamino)-phenyl]-3-(4-trifluoromethyl-phenyl)-urea

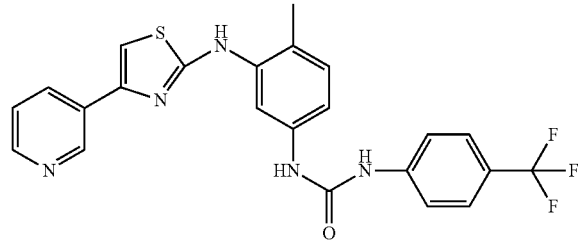 [SMILES: Cc1ccc(NC(=O)Nc2ccc(C(F)(F)F)cc2)cc1Nc1nc(-c2cccnc2)cs1]

012: 1-(4-Fluoro-phenyl)-3-[4-methyl-3-(4-pyridin-3-yl-thiazol-2-ylamino)-phenyl]-urea

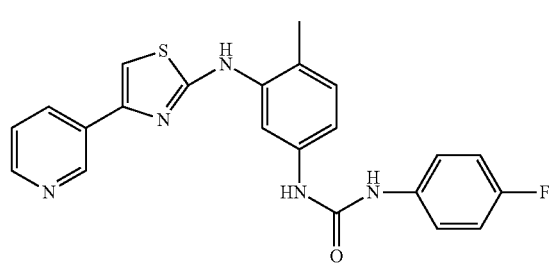 [SMILES: Cc1ccc(NC(=O)Nc2ccc(F)cc2)cc1Nc1nc(-c2cccnc2)cs1]

013: 1-[4-Methyl-3-(4-pyridin-3-yl-thiazol-2-ylamino)-phenyl]-3-(3,4,5-trimethoxy-phenyl)-urea

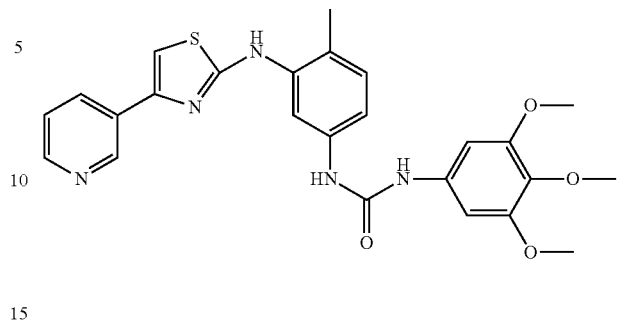

014: 4-{3-[4-Methyl-3-(4-pyridin-3-yl-thiazol-2-ylamino)-phenyl]-ureido}-benzoic acid ethyl ester

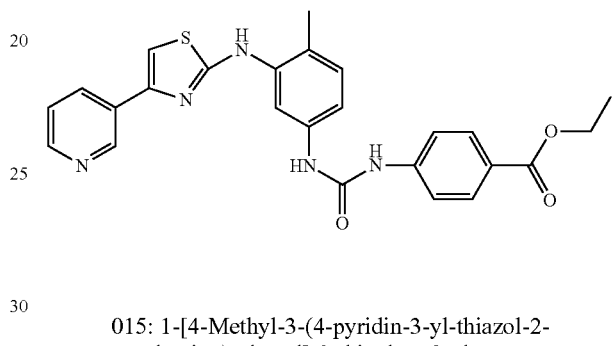

015: 1-[4-Methyl-3-(4-pyridin-3-yl-thiazol-2-ylamino)-phenyl]-3-thiophen-2-yl-urea

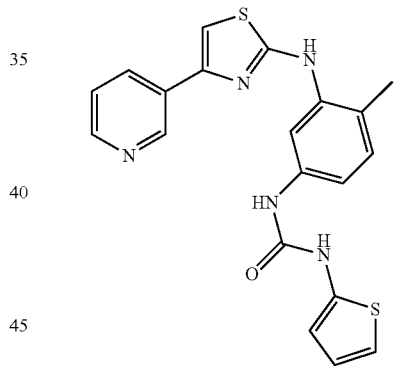

016: 1-Cyclohexyl-1-(N-Cyclohexyl-formamide)-3-[4-methyl-3-(4-pyridin-3-yl-thiazol-2-ylamino)-phenyl]-urea

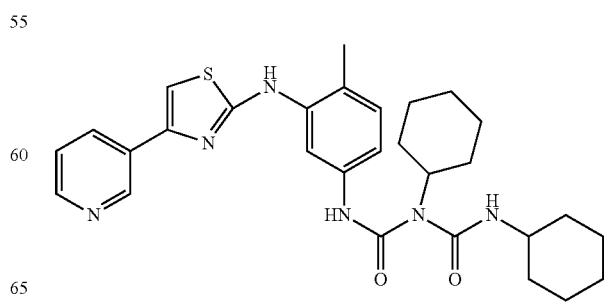

017: 1-(2,4-Dimethoxy-phenyl)-3-[4-methyl-3-(4-pyridin-3-yl-thiazol-2-ylamino)-phenyl]-urea

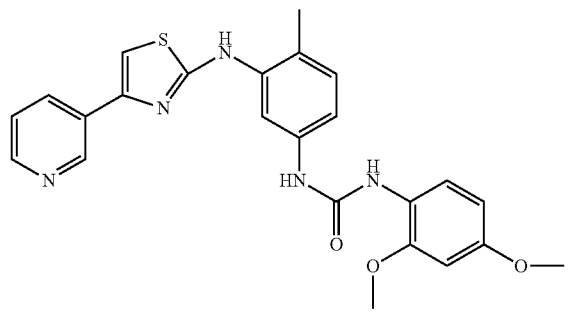 [SMILES: COc1ccc(NC(=O)Nc2ccc(C)c(Nc3nc(-c4cccnc4)cs3)c2)c(OC)c1]

018: 1-(2-Iodo-phenyl)-1-(N-(2-Iodo-phenyl)-formamide)-3-[4-methyl-3-(4-pyridin-3-yl-thiazol-2-ylamino)-phenyl]-urea

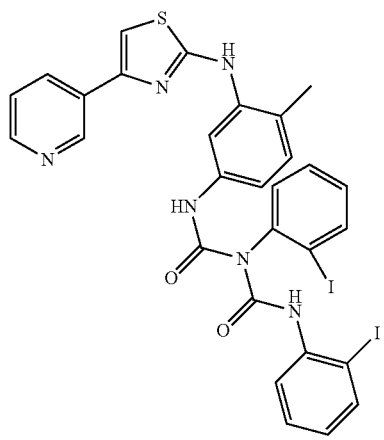 [SMILES: Cc1ccc(NC(=O)N(C(=O)Nc2ccccc2I)c2ccccc2I)cc1Nc1nc(-c2cccnc2)cs1]

019: 1-(3,5-Dimethyl-isoxazol-4-yl)-3-[4-methyl-3-(4-pyridin-3-yl-thiazol-2-ylamino)-phenyl]-urea

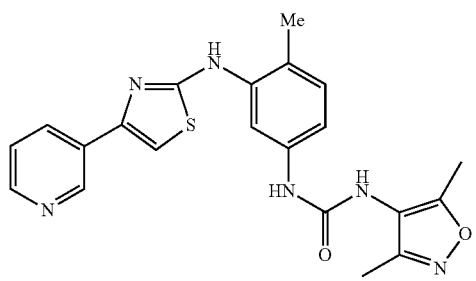 [SMILES: Cc1ccc(NC(=O)Nc2c(C)noc2C)cc1Nc1nc(-c2cccnc2)cs1]

020: 1-(2-Iodo-phenyl)-3-[4-methyl-3-(4-pyridin-3-yl-thiazol-2-ylamino)-phenyl]-urea

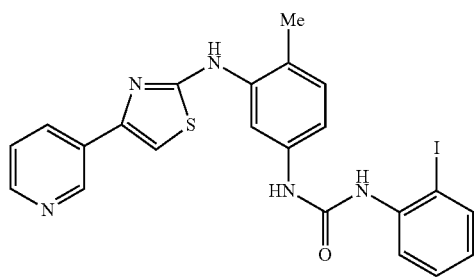 [SMILES: Cc1ccc(NC(=O)Nc2ccccc2I)cc1Nc1nc(-c2cccnc2)cs1]

021: 1-(4-Difluoromethoxy-phenyl)-3-[4-methyl-3-(4-pyridin-3-yl-thiazol-2-ylamino)-phenyl]-urea

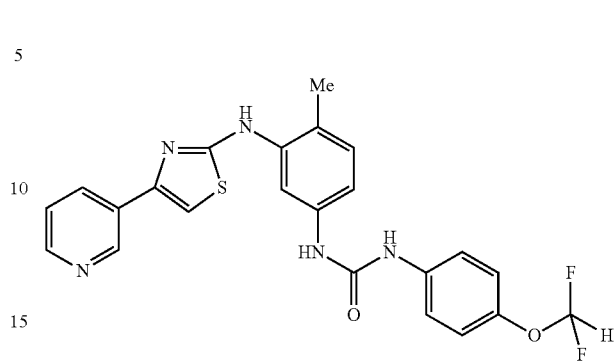

022: 1-(4-Dimethylamino-phenyl)-3-[4-methyl-3-(4-pyridin-3-yl-thiazol-2-ylamino)-phenyl]-urea

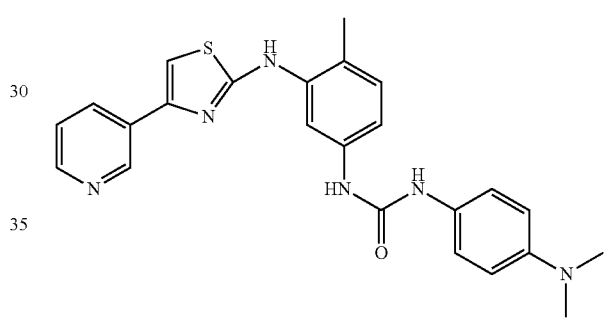

023: 1-(2-Fluoro-phenyl)-3-[4-methyl-3-(4-pyridin-3-yl-thiazol-2-ylamino)-phenyl]-urea

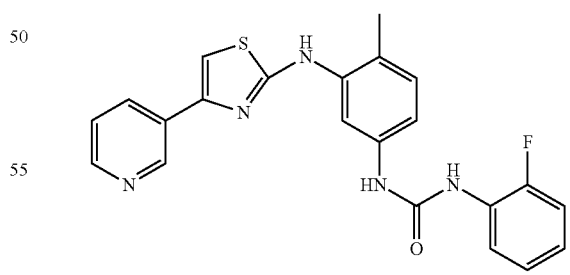

light brown powder mp: 203-206° C.

$^1$H NMR (DMSO-d$^6$): δ=2.24 (s, 3H); 6.98-7.00 (m, 2H); 7.10-7.23 (m, 3H); 7.40 (m, 1H); 7.48 (s, 1H); 8.25 (m, 1H); 8.37 (d, J=7.8 Hz, 1H); 8.51 (m, 3H); 9.03 (s, 1H); 9.19 (s, 1H); 9.39 (s, 1H)

024: 1-(2-Chloro-phenyl)-3-[4-methyl-3-(4-pyridin-3-yl-thiazol-2-ylamino)-phenyl]-urea

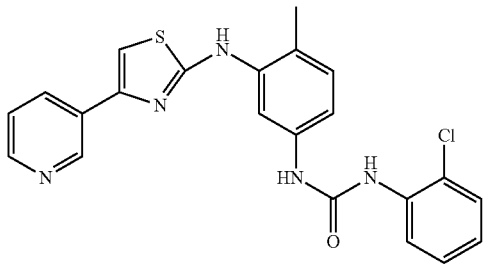 [SMILES: Cc1ccc(NC(=O)Nc2ccccc2Cl)cc1Nc1nc(-c2cccnc2)cs1]

025: 1-(3-Fluoro-phenyl)-3-[4-methyl-3-(4-pyridin-3-yl-thiazol-2-ylamino)-phenyl]-urea

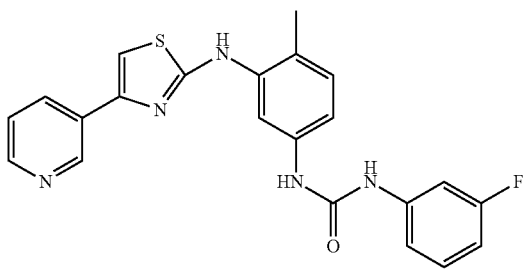 [SMILES: Cc1ccc(NC(=O)Nc2cccc(F)c2)cc1Nc1nc(-c2cccnc2)cs1]

white powder mp: 210-215° C.

$^1$H NMR (DMSO-d$^6$): δ=2.24 (s, 3H); 6.79 (t, J=6.3 Hz, 1H); 6.99 (m, 1H); 7.09-7.14 (m, 2H); 7.30 (m, 1H); 7.41 (t, J=4.7 Hz, 1H); 7.48 (s, 1H); 7.56 (d, J=1.2 Hz, 1H); 8.39 (d, J=8.0 Hz, 1H); 8.49-8.52 (m, 2H); 8.71 (s, 1H); 8.87 (s, 1H); 9.18 (s, 1H); 9.38 (s, 1H)

026: 1-[4-Methyl-3-(4-pyridin-3-yl-thiazol-2-ylamino)-phenyl]-3-p-tolyl-urea

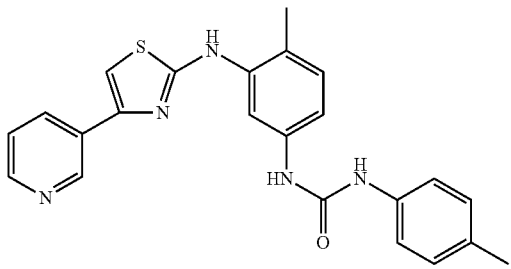 [SMILES: Cc1ccc(NC(=O)Nc2ccc(C)c(Nc3nc(-c4cccnc4)cs3)c2)cc1]

white powder mp: 238-240° C.

$^1$NMR (DMSO-d$^6$) δ=2.29 (s, 3H); 2.31 (s, 3H); 7.05 (d, J=6.2 Hz, 1H); 7.10-1.16 (m, 3H); 7.42-7.49 (m, 3H); 7.53 (s, 1H); 8.35-8.62 (m, 5H); 9.22 (d, J=1.6 Hz, 1H); 9.43 (s, 1H)

Among the compounds of formula II, the invention is particularly embodied by the compounds wherein X is a -substituted Aryl group, corresponding to the N-[3-(Thiazol-2-ylamino)-phenyl]-amide family and the following formula II-3:

FORMULA II-3

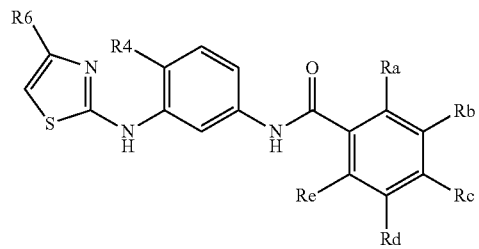

wherein Ra, Rb, Rc, Rd, Re are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a —SO2-R group wherein R is an alkyl, cycloalkyl, aryl or heteroaryl optionally substituted with a heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and or bearing a pendant basic nitrogen functionality;

Ra, Rb, Rc, Rd, Re may also be a halogen such as I, Cl, Br and F a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a COOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CONRaRb, where Ra and Rb are a hydrogen or a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $NRaOSO_2Rb$, where Ra and Rb are a linear or branched alkyl group containing from 1 to 10 carbon atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CN group a trifluoromethyl group $R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

Examples

028: 3-Bromo-N-[4-methyl-3-(4-pyridin-3-yl-thiazol-2-ylamino)-phenyl]-benzamide

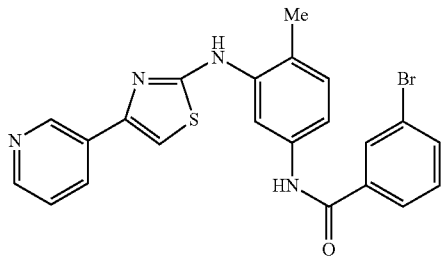 [SMILES: Cc1ccc(NC(=O)c2cccc(Br)c2)cc1Nc1nc(-c2cccnc2)cs1]

029: 3-Iodo-N-[4-methyl-3-(4-pyridin-3-yl-thiazol-2-ylamino)-phenyl]-benzamide

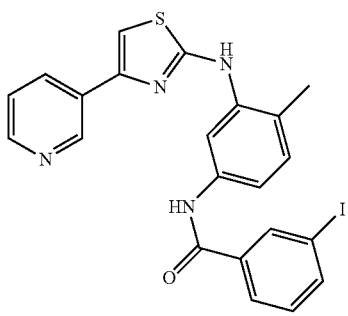 [SMILES: Cc1ccc(NC(=O)c2cccc(I)c2)cc1Nc1nc(-c2cccnc2)cs1]

030: 4-Hydroxymethyl-N-[4-methyl-3-(4-pyridin-3-yl-thiazol-2-ylamino)-phenyl]-benzamide

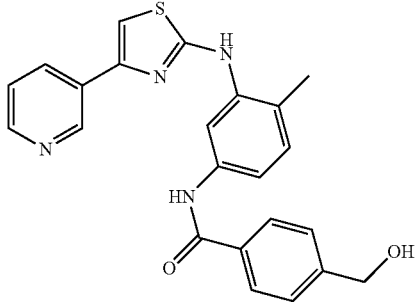 [SMILES: Cc1ccc(NC(=O)c2ccc(CO)cc2)cc1Nc1nc(-c2cccnc2)cs1]

031: 4-Amino-N-[4-methyl-3-(4-pyridin-3-yl-thiazol-2-ylamino)-phenyl]-benzamide

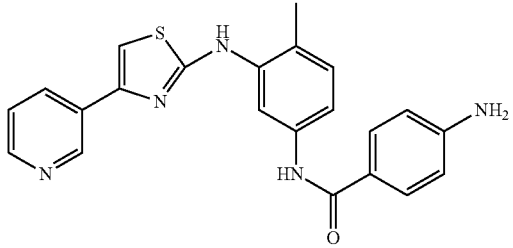 [SMILES: Cc1ccc(NC(=O)c2ccc(N)cc2)cc1Nc1nc(-c2cccnc2)cs1]

032: 2-Iodo-N-[4-methyl-3-(4-pyridin-3-yl-thiazol-2-ylamino)-phenyl]-benzamide

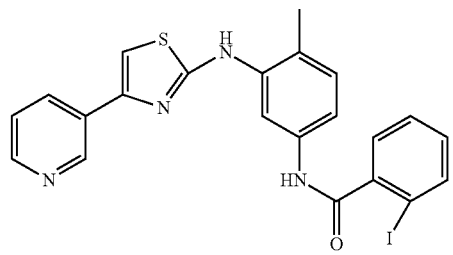 [SMILES: Cc1ccc(NC(=O)c2ccccc2I)cc1Nc1nc(-c2cccnc2)cs1]

033: 4-Iodo-N-[4-methyl-3-(4-pyridin-3-yl-thiazol-2-ylamino)-phenyl]-benzamide

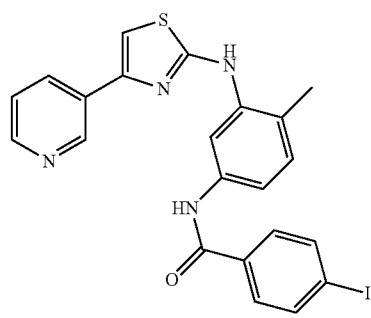 [SMILES: Cc1ccc(NC(=O)c2ccc(I)cc2)cc1Nc1nc(-c2cccnc2)cs1]

034: 4-(3-{4-[4-Methyl-3-(4-pyridin-3-yl-thiazol-2-ylamino)-phenylcarbamoyl]-phenyl}-ureido)-benzoic acid ethyl ester

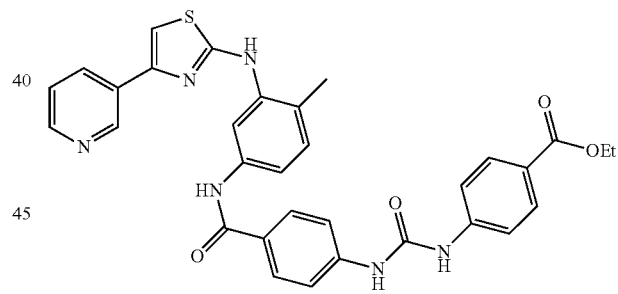

035: N-[4-Methyl-3-(4-pyridin-3-yl-thiazol-2-ylamino)-phenyl]-4-[3-(4-trifluoromethyl-phenyl)-ureido]-benzamide

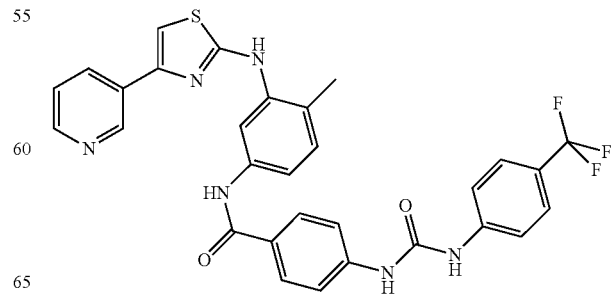

036: 4-[3-(4-Bromo-phenyl)-ureido]-N-[4-methyl-3-(4-pyridin-3-yl-thiazol-2-ylamino)-phenyl]-benzamide

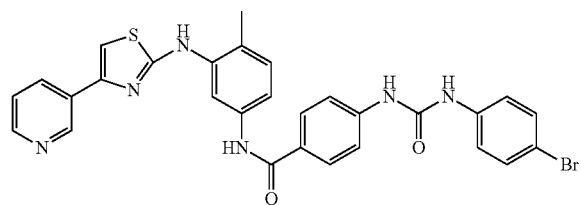 [SMILES: Cc1ccc(NC(=O)c2ccc(NC(=O)Nc3ccc(Br)cc3)cc2)cc1Nc1nc(-c2cccnc2)cs1]

037: 4-Hydroxy-N-[4-methyl-3-(4-pyridin-3-yl-thiazol-2-ylamino)-phenyl]-benzamide

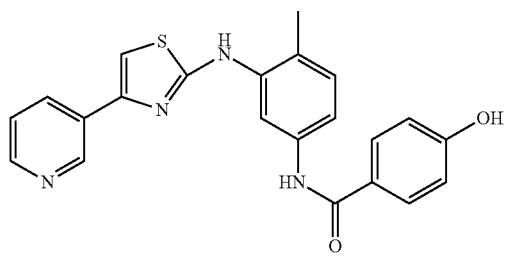 [SMILES: Cc1ccc(NC(=O)c2ccc(O)cc2)cc1Nc1nc(-c2cccnc2)cs1]

038: N-[4-Methyl-3-(4-pyridin-3-yl-thiazol-2-ylamino)-phenyl]-4-(3-thiophen-2-yl-ureido)-benzamide

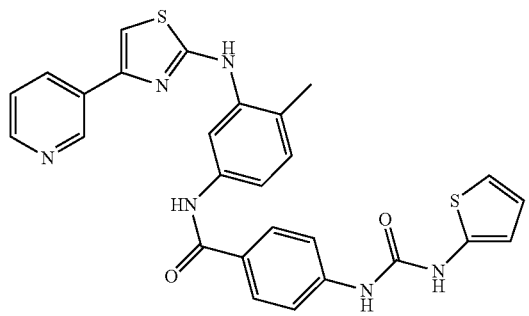 [SMILES: Cc1ccc(NC(=O)c2ccc(NC(=O)Nc3cccs3)cc2)cc1Nc1nc(-c2cccnc2)cs1]

039: 4-[3-(3,5-Dimethyl-isoxazol-4-yl)-ureido]-N-[4-methyl-3-(4-pyridin-3-yl-thiazol-2-ylamino)-phenyl]-benzamide

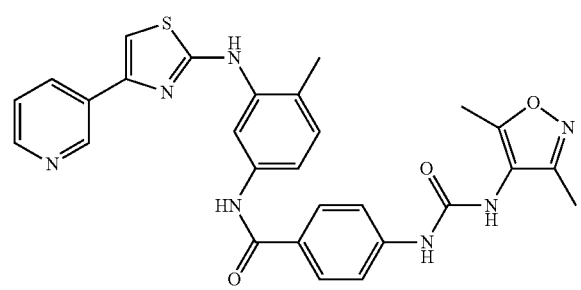 [SMILES: Cc1ccc(NC(=O)c2ccc(NC(=O)Nc3c(C)noc3C)cc2)cc1Nc1nc(-c2cccnc2)cs1]

040: 4-[3-(4-Methoxy-phenyl)-ureido]-N-[4-methyl-3-(4-pyridin-3-yl-thiazol-2-ylamino)-phenyl]-benzamide

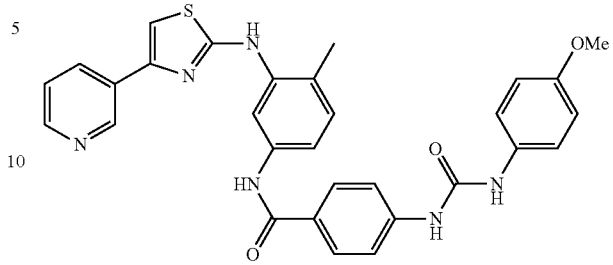

041: 4-[3-(4-Difluoromethoxy-phenyl)-ureido]-N-[4-methyl-3-(4-pyridin-3-yl-thiazol-2-ylamino)-phenyl]-benzamide

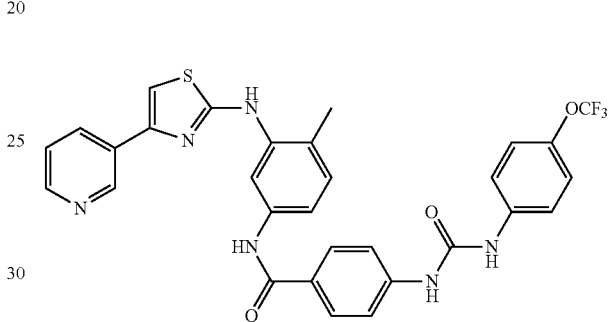

042: Thiophene-2-sulfonic acid 4-[4-methyl-3-(4-pyridin-3-yl-thiazol-2-ylamino)-phenylcarbamoyl]-phenyl ester

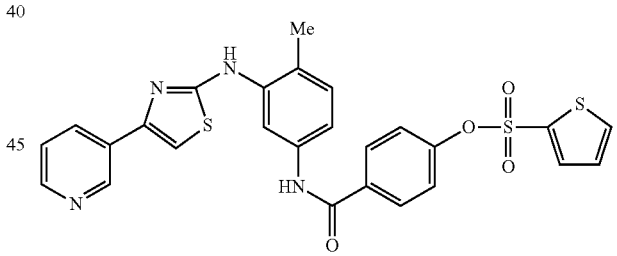

043: 4-Iodo-benzenesulfonic acid 4-[4-methyl-3-(4-pyridin-3-yl-thiazol-2-ylamino)-phenylcarbamoyl]-phenyl ester

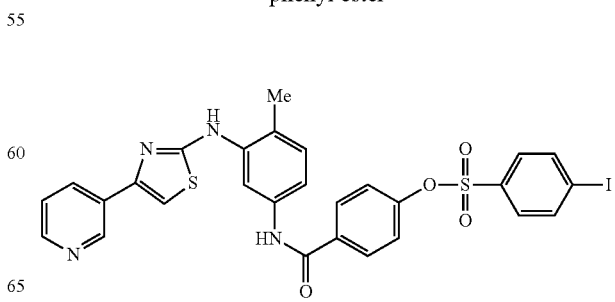

044: N-[4-Methyl-3-(4-pyridin-3-yl-thiazol-2-ylamino)-phenyl]-4-(thiophene-2-sulfonylamino)-benzamide

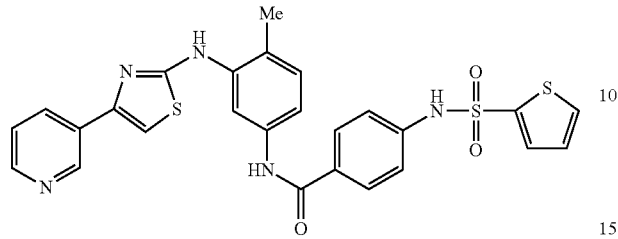

brown powder mp: 230-233° C.
$^{1}$H NMR (DMSO-d$^{6}$) δ=2.29 (s, 3H); 7.15-7.18 (m, 2H); 7.22-7.32 (m, 3H); 7.48 (m, 2H); 7.67 (dd, J=1.3 Hz, J=3.7 Hz, 1H); 7.90-7.96 (m, 3H); 8.38-8.42 (m, 1H); 8.51 (m, 1H); 8.57 (d, J=1.9 Hz, 1H); 9.17 (d, J=1.7 Hz, 1H); 9.44 (s, 1H); 10.12 (s, 1H); 10.82 (s, 1H)

045: 3-Fluoro-N-[4-methyl-3-(4-pyridin-3-yl-thiazol-2-ylamino)-phenyl]-benzamide

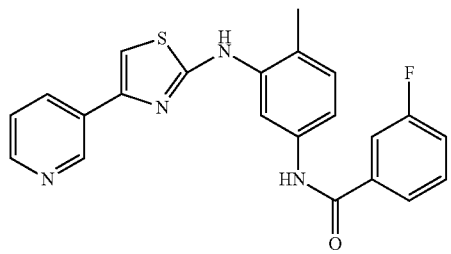 [SMILES: Cc1ccc(NC(=O)c2cccc(F)c2)cc1Nc1nc(-c2cccnc2)cs1]

off-white foam mp: 184-186° C.
$^{1}$H NMR (CD$_{3}$OD-d$^{4}$): δ=2.23 (s, 3H); 7.12-7.14 (m, 2H); 7.20-7.23 (m, 2H); 7.30 (m, 1H); 7.43 (m, 1H); 7.50 (m, 1H); 7.66 (d, J=1.0 Hz, 1H); 8.23 (m, 1H); 8.33 (m, 1H); 8.38 (s, 1H); 8.98 (s, 1H)

046: N-[4-Methyl-3-(4-pyridin-3-yl-thiazol-2-ylamino)-phenyl]-4-pyridin-4-yl-benzamide

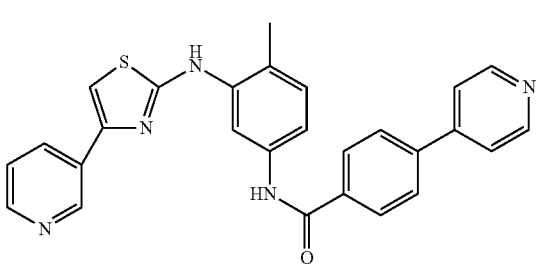 [SMILES: Cc1ccc(NC(=O)c2ccc(-c3ccncc3)cc2)cc1Nc1nc(-c2cccnc2)cs1]

yellow powder mp: 254-256° C.
$^{1}$H NMR (DMSO-d$^{6}$): δ 2.34 (s, 3H); 7.28 (d, J=8.0 Hz, 1H); 7.45-7.49 (m, 2H); 7.54 (s, 1H); 7.78 (t, J=7.6 Hz, 1H); 7.89-7.91 (m, 2H); 8.10 (t, J=7.8 Hz, 2H); 8.37-8.42 (m, 2H); 8.55 (d, J=4.7 Hz, 1H); 8.73-8.77 (m, 3H); 9.24 (s, 1H); 9.52 (s, 1H); 10.43 (s, 1H)

047: 4-Dimethylamino-N-[4-methyl-3-(4-pyridin-3-yl-thiazol-2-ylamino)-phenyl]-benzamide

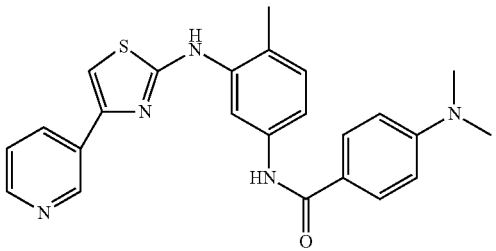 [SMILES: Cc1ccc(NC(=O)c2ccc(N(C)C)cc2)cc1Nc1nc(-c2cccnc2)cs1]

beige powder mp: 147-150° C.
$^{1}$H NMR (DMSO-d$^{6}$): δ 2.25 (s, 3H); 2.99 (s, 6H); 6.76 (d, J=8.9 Hz, 2H); 7.16 (d, J=8.3 Hz, 1H); 7.35 (d, J=2.0 Hz, 1H); 7.44-7.47 (m, 2H); 7.86-7.89 (m, 2H); 8.34-8.36 (m, 1H); 8.48-8.50 (m, 1H); 8.56-8.57 (m, 1H); 9.16 (s, 1H); 9.44 (s, 1H); 9.85 (s, 1H)

048: 2-Fluoro-5-methyl-N-[4-methyl-3-(4-pyridin-3-yl-thiazol-2-ylamino)-phenyl]-benzamide

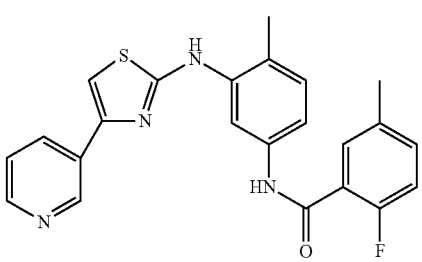 [SMILES: Cc1ccc(F)c(C(=O)Nc2ccc(C)c(Nc3nc(-c4cccnc4)cs3)c2)c1]

brown orange powder mp: 103-106° C.
$^{1}$H NMR (DMSO-d$^{6}$) δ=2.26 (s, 3H); 2.35 (s, 3H); 7.17-7.47 (m, 7H); 8.29 (dd, J=1.6 Hz, J=7.9 Hz, 1H); 8.47 (d, J=3.5 Hz, 1H); 8.57 (s, 1H); 9.15 (d, J=2.0 Hz, 1H); 9.44 (s, 1H); 10.33 (s, 1H)

049: 4-tert-Butyl-N-[4-methyl-3-(4-pyridin-3-yl-thiazol-2-ylamino)-phenyl]-benzamide

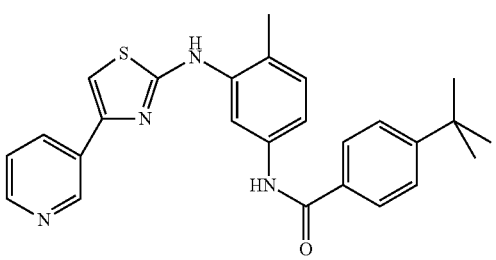 [SMILES: Cc1ccc(NC(=O)c2ccc(C(C)(C)C)cc2)cc1Nc1nc(-c2cccnc2)cs1]

brown powder mp: 145-150° C.
$^{1}$H NMR (DMSO-d$^{6}$) δ=1.32 (s, 9H); 2.04 (s, 3H); 7.18 (d, J=8.4 Hz, 1H); 7.35-7.44 (m, 2H); 7.46 (s, 1H); 7.55 (d, J=8.5 Hz, 1H); 7.90 (d, J=8.5 Hz, 1H); 8.32 (d, J=7.9 Hz, 1H); 8.47

(dd, J=1.5 Hz, J=4.7 Hz, 1H); 8.60 (d, J=2.0 Hz, 1H); 9.15 (d, J=1.7 Hz, 1H); 9.43 (s, 1H); 10.15 (s, 1H)

050: 4-Isopropoxy-N-[4-methyl-3-(4-pyridin-3-yl-thiazol-2-ylmethyl)-phenyl]-benzamide

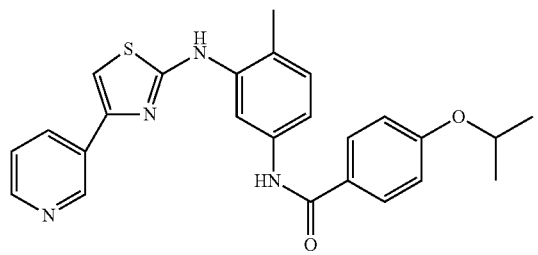 [SMILES: Cc1ccc(NC(=O)c2ccc(OC(C)C)cc2)cc1Nc1nc(-c2cccnc2)cs1]

brown powder mp: 154-155° C.
$^1$H NMR (DMSO-d$^6$) δ=1.34 (d, J=5.9 Hz, 6H); 4.72 (hept, J=5.9 Hz, 1H); 7.01 (d, J=7.0 Hz, 2H); 7.18 (d, J=8.5 Hz, 1H); 7.35-7.44 (m, 2H); 7.46 (s, 1H); 7.94 (dd, J=2.0 Hz, J=6.7 Hz, 2H); 8.32 (d, J=8.3 Hz, 1H); 8.48 (dd, J=3.3 Hz, J=4.8 Hz, 1H); 8.58 (d, J=2.0 Hz, 1H); 9.15 (d, J=1.8 Hz, 1H); 9.43 (s, 1H); 10.4 (s, 1H)

051: Benzo[1,3]dioxole-5-carboxylic acid [4-methyl-3-(4-pyridin-3-yl-thiazol-2-ylmethyl)-phenyl]-amide

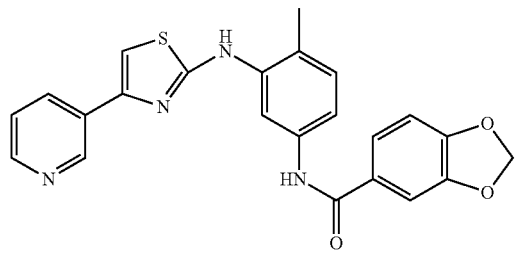 [SMILES: Cc1ccc(NC(=O)c2ccc3c(c2)OCO3)cc1Nc1nc(-c2cccnc2)cs1]

brown orange powder mp: 130-132° C.
$^1$H NMR (DMSO-d$^6$) δ=2.23 (s, 3H); 6.10 (s, 2H); 7.03 (d, J=8.1 Hz, 1H); 7.15 (d, J=8.3 Hz, 1H); 7.25-7.55 (m, 6H); 8.26 (s, 1H); 8.45 (dd, J=1.5 Hz, J=4.7, 1H); 8.55 (d, J=2.0 Hz, 1H); 9.12 (d, J=1.7 Hz, 1H); 9.40 (s, 1H); 10.01 (s, 1H)

052: N-[4-Methyl-3-(4-pyridin-3-yl-thiazol-2-ylamino)-phenyl]-3-(2-morpholin-4-yl-ethoxy)-benzamide

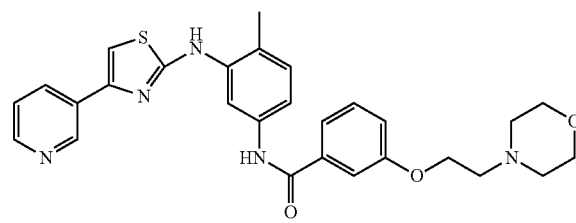 [SMILES: Cc1ccc(NC(=O)c2cccc(OCCN3CCOCC3)c2)cc1Nc1nc(-c2cccnc2)cs1]

beige yellow powder mp: 75-80° C.
$^1$H NMR (DMSO-d$^6$) δ=2.10-2.25 (m, 4H); 2.50-2.60 (m, 2H); 3.19 (s, 3H); 3.41-3.48 (m, 4H); 4.00-4.06 (m, 2H); 7.00-7.11 (m, 2H); 7.22-7.35 (m, 6H), 8.18 (d, J=8.0 Hz, 1H); 8.33 (d, J=0.9 Hz, 1H); 8.49 (d, J=1.7 Hz, 1H); 9.03 (s, 1H); 9.31 (s, 1H); 10.05 (s, 1H)

053: N-[4-Methyl-3-(4-pyridin-3-yl-thiazol-2-ylmethyl)-phenyl]-4-pyridin-4-yl-benzamide

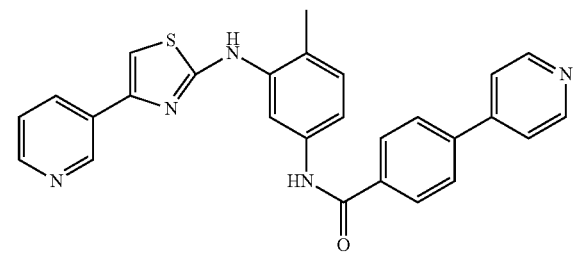 [SMILES: Cc1ccc(NC(=O)c2ccc(-c3ccncc3)cc2)cc1Nc1nc(-c2cccnc2)cs1]

brown powder mp: dec. 250° C.
$^1$H NMR (DMSO-d$^6$) δ=2.28 (s, 3H); 7.21 (d, J=7.9 Hz, 1H); 7.30-7.50 (m, 3H); 7.81 (d, J=4.7 Hz, 1H); 7.98 (d, J=7.5 Hz, 2H); 8.13 (d, J=7.9 Hz, 2H); 8.32 (d, J=7.7 Hz, 1H); 8.48 (d, J=4.9 Hz, 1H); 8.62-8.69 (m, 3H); 9.16 (s, 1H); 9.45 (s, 1H); 10.34 (s, 1H)

054: 3-Cyano-N-[4-methyl-3-(4-pyridin-3-yl-thiazol-2-ylamino)-phenyl]-benzamide

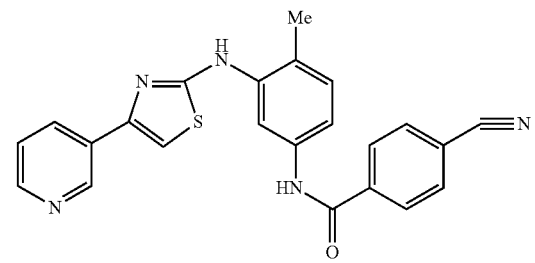 [SMILES: Cc1ccc(NC(=O)c2ccc(C#N)cc2)cc1Nc1nc(-c2cccnc2)cs1]

055: 2-Fluoro-N-[4-methyl-3-(4-pyridin-3-yl-thiazol-2-ylamino)-phenyl]-3-trifluoromethyl-benzamide

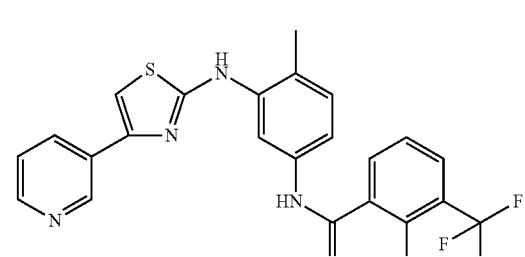

056: 3-Fluoro-benzenesulfonic acid 4-[4-methyl-3-(4-pyridin-3-yl-thiazol-2-ylamino)-phenylcarbamoyl]-phenyl ester

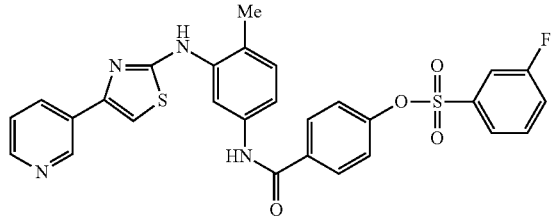 [SMILES: Cc1ccc(NC(=O)c2ccc(OS(=O)(=O)c3cccc(F)c3)cc2)cc1Nc1nc(-c2cccnc2)cs1]

057: 4-Aminomethyl-N-[4-methyl-3-(4-pyridin-3-yl-thiazol-2-ylamino)-phenyl]-benzamide

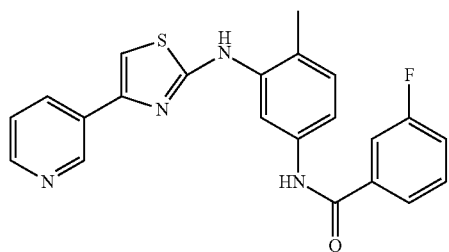 [SMILES: Cc1ccc(NC(=O)c2cccc(F)c2)cc1Nc1nc(-c2cccnc2)cs1]

058: 2-Fluoro-benzenesulfonic acid 4-[4-methyl-3-(4-pyridin-3-yl-thiazol-2-ylamino)-phenylcarbamoyl]-phenyl ester

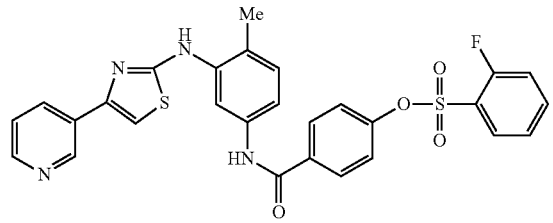 [SMILES: Cc1ccc(NC(=O)c2ccc(OS(=O)(=O)c3ccccc3F)cc2)cc1Nc1nc(-c2cccnc2)cs1]

059: -Methoxy-N-[4-methyl-3-(4-pyridin-3-yl-thiazol-2-ylmethyl)-phenyl]-benzamide

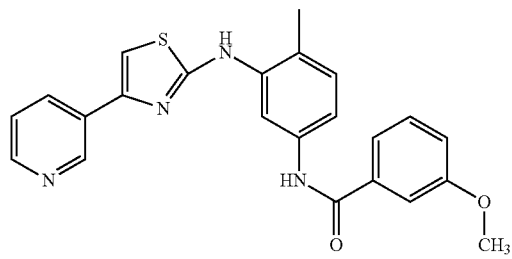 [SMILES: COc1cccc(C(=O)Nc2ccc(C)c(Nc3nc(-c4cccnc4)cs3)c2)c1]

white powder mp: 76-79° C.
$^1$H NMR (DMSO-d$^6$) δ=2.32 (s, 3H); 3.89 (s, 3H); 7.22-7.25 (m, 2H), 7.44-7.58 (m, 4H); 8.28-8.35 (m, 1H); 8.52 (dd, J=1.6 Hz, J=4.7 Hz, 1H); 8.66 (d, J=2.0 Hz, 1H); 9.20 (d, J=1.4 Hz, 1H); 9.50 (s, 1H); 10.25 (s, 1H)

060: 4-(4-Methyl-piperazin-1-yl)-N-[4-methyl-3-(4-pyridin-3-yl-thiazol-2-ylmethyl)-phenyl]-benzamide

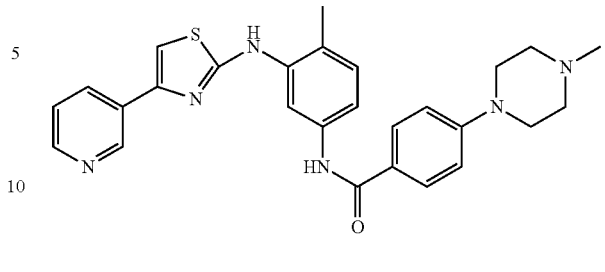

beige brown powder mp: 128-130° C.
$^1$H NMR (DMSO-d$^6$) δ=2.15 (s, 3H); 2.18 (s, 3H); 2.35-2.41 (m, 4H); 3.18-3.3.24 (m, 4H); 6.94 (d, J=8.9 Hz, 2H); 7.09 (d, J=8.4 Hz, 1H); 7.28-7.38 (m, 3H); 7.81 (d, J=8.9 Hz, 2H); 8.20-8.25 (m, 1H); 8.40 (dd, J=1.6 Hz, J=4.7, 1H); 8.48 (d, J=1.9 Hz, 1H); 9.07 (d, J=1.5 Hz, 1H); 9.35 (s, 1H); 9.84 (s, 1H)

061: 3-Methyl-N-[4-methyl-3-(4-pyridin-3-yl-thiazol-2-ylamino)-phenyl]-benzamide

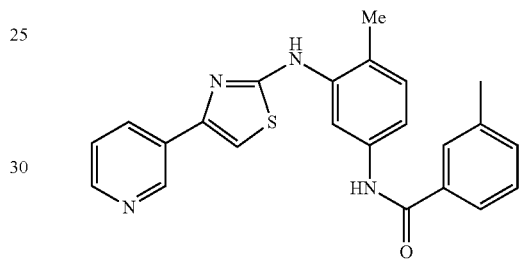

062: Biphenyl-3-carboxylic acid [4-methyl-3-(4-pyridin-3-yl-thiazol-2-ylamino)-phenyl]-amide

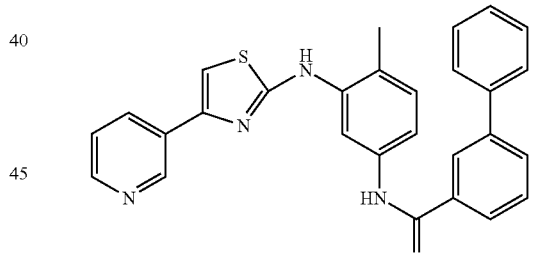

065: N-[4-Methyl-3-(4-pyridin-3-yl-thiazol-2-ylamino)-phenyl]-3-trifluoromethyl-benzamide

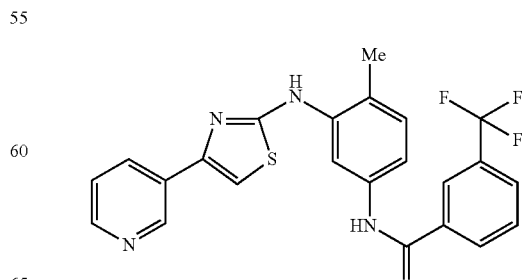

099: N-[4-Methyl-3-(4-pyridin-3-yl-thiazol-2-ylamino)-phenyl]-4-pyrrolidin-1-ylmethyl-benzamide

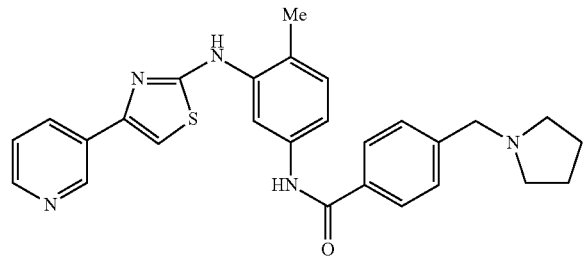 [SMILES: Cc1ccc(NC(=O)c2ccc(CN3CCCC3)cc2)cc1Nc1nc(-c2cccnc2)cs1]

100: 4-[3-(2,4-Dimethoxy-phenyl)-ureido]-N-[4-methyl-3-(4-pyridin-3-yl-thiazol-2-ylamino)-phenyl]-benzamide

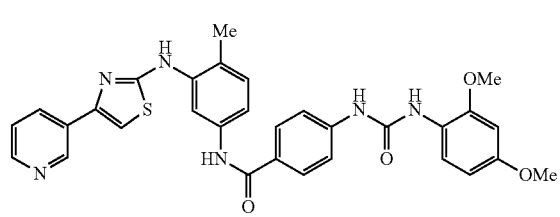 [SMILES: COc1ccc(NC(=O)Nc2ccc(C(=O)Nc3ccc(C)c(Nc4nc(-c5cccnc5)cs4)c3)cc2)c(OC)c1]

101: 4-[3-(2-Iodo-phenyl)-ureido]-N-[4-methyl-3-(4-pyridin-3-yl-thiazol-2-ylamino)-phenyl]-benzamide

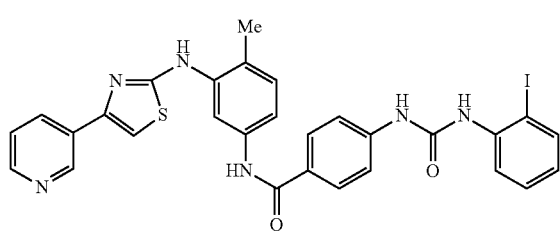 [SMILES: Cc1ccc(NC(=O)c2ccc(NC(=O)Nc3ccccc3I)cc2)cc1Nc1nc(-c2cccnc2)cs1]

102: 4-[3-(4-Fluoro-phenyl)-ureido]-N-[4-methyl-3-(4-pyridin-3-yl-thiazol-2-ylamino)-phenyl]-benzamide

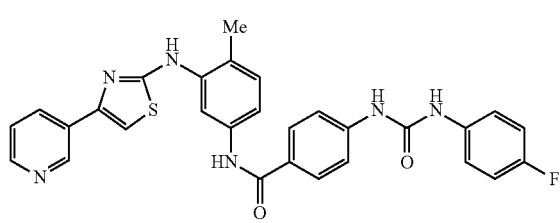 [SMILES: Cc1ccc(NC(=O)c2ccc(NC(=O)Nc3ccc(F)cc3)cc2)cc1Nc1nc(-c2cccnc2)cs1]

105: 3-Bromo-4-methyl-N-[4-methyl-3-(4-pyridin-3-yl-thiazol-2-ylamino)-phenyl]-benzamide 106: 4-Fluoro-N-[4-methyl-3-(4-pyridin-3-yl-thiazol-2-ylamino)-phenyl]-benzamide

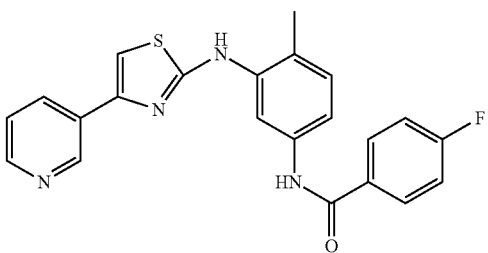 [SMILES: Cc1ccc(NC(=O)c2ccc(F)cc2)cc1Nc1nc(-c2cccnc2)cs1]

103: 4-Cyano-N-[4-methyl-3-(4-pyridin-3-yl-thiazol-2-ylamino)-phenyl]-benzamide

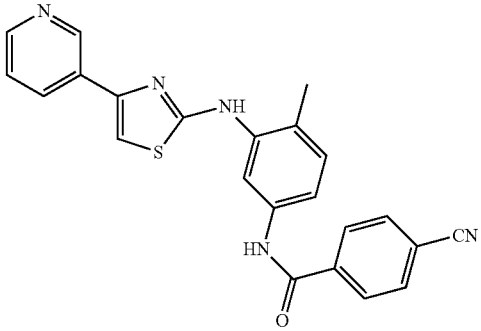 [SMILES: Cc1ccc(NC(=O)c2ccc(C#N)cc2)cc1Nc1nc(-c2cccnc2)cs1]

104: 4-Fluoro-N-[4-methyl-3-(4-pyridin-3-yl-thiazol-2-ylamino)-phenyl]-benzamide

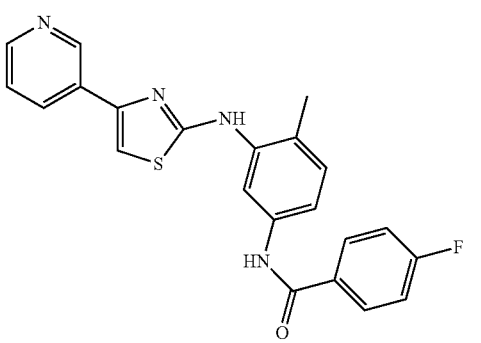 [SMILES: Cc1ccc(NC(=O)c2ccc(F)cc2)cc1Nc1nc(-c2cccnc2)cs1]

Among compounds of formula II, the invention is particularly embodied by the compounds wherein X is a -substituted-aryl group, corresponding to the 4-(4-substituted-1-yl-methyl)-N-[3-(thiazol-2-ylamino)-phenyl]-benzamide family and the following formula II-4:

FORMULA II-4

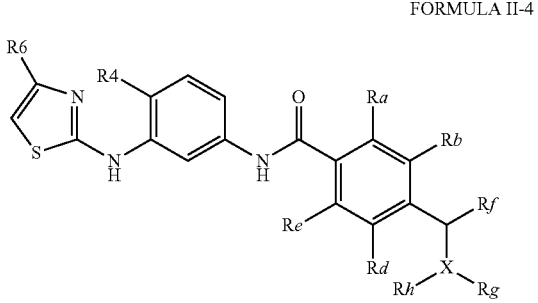

wherein X is a heteroatom, such as O or N
wherein Ra, Rb, Rd, Re, Rf, Rg, Rh are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- or a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- or an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;
- or a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- or a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;
- or a COOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- or a CONRaRb, where Ra and Rb are a hydrogen or a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- or an NHCOOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;
- an OSO$_2$R, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NRaOSO₂Rb, where Ra and Rb are a linear or branched alkyl group containing from 1 to 10 carbon atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Ra, Rb, Rd, Re can also be halogen such as Cl, F, Br, I or trifluoromethyl;

$R^4$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

Examples

066: 4-(4-methyl-piperazin-1-ylmethyl)-N-[4-methyl-3-(4-pyridin-3-yl-thiazol-2-ylamino)-phenyl]-benzamide

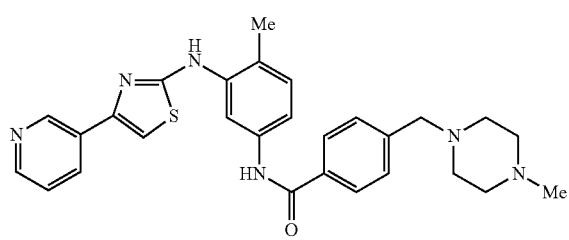 [SMILES: Cc1ccc(NC(=O)c2ccc(CN3CCN(C)CC3)cc2)cc1Nc1nc(-c2cccnc2)cs1]

067: 3,5-Dibromo-4-(4-methyl-piperazin-1-ylmethyl)-N-[4-methyl-3-(4-pyridin-3-yl-thiazol-2-ylamino)-phenyl]-benzamide

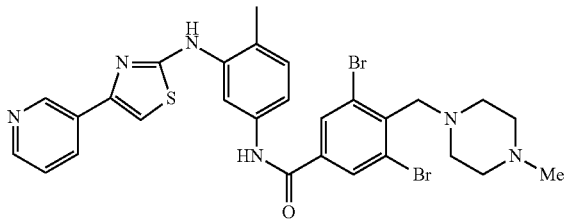 [SMILES: Cc1ccc(NC(=O)c2cc(Br)c(CN3CCN(C)CC3)c(Br)c2)cc1Nc1nc(-c2cccnc2)cs1]

068: 4-Diethylaminomethyl-N-[4-methyl-3-(4-pyridin-3-yl-thiazol-2-ylamino)-phenyl]-benzamide

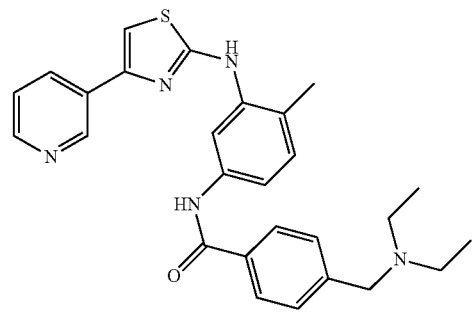 [SMILES: CCN(CC)Cc1ccc(C(=O)Nc2ccc(C)c(Nc3nc(-c4cccnc4)cs3)c2)cc1]

069: N-[4-Methyl-3-(4-pyridin-3-yl-thiazol-2-ylamino)-phenyl]-4-morpholin-4-ylmethyl-benzamide

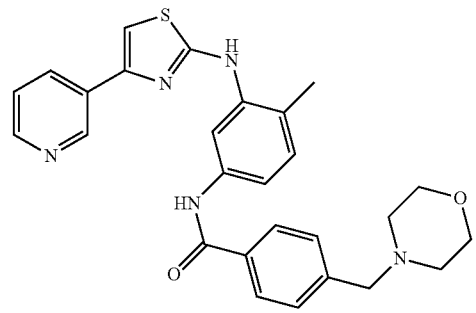 [SMILES: Cc1ccc(NC(=O)c2ccc(CN3CCOCC3)cc2)cc1Nc1nc(-c2cccnc2)cs1]

070: 4-Dipropylaminomethyl-N-[4-methyl-3-(4-pyridin-3-yl-thiazol-2-ylamino)-phenyl]-benzamide

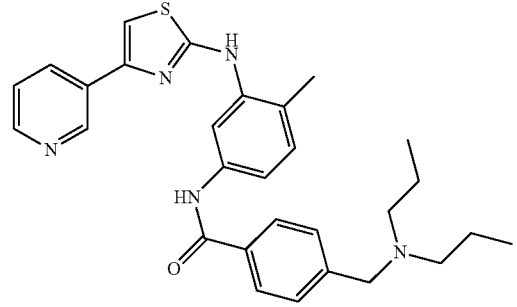 [SMILES: CCCN(CCC)Cc1ccc(C(=O)Nc2ccc(C)c(Nc3nc(-c4cccnc4)cs3)c2)cc1]

071: N-[4-Methyl-3-(4-pyridin-3-yl-thiazol-2-ylamino)-phenyl]-4-piperidin-1-ylmethyl-benzamide

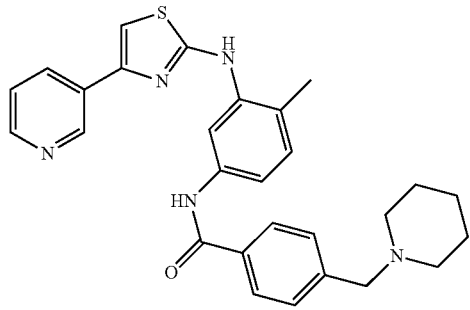 [SMILES: Cc1ccc(NC(=O)c2ccc(CN3CCCCC3)cc2)cc1Nc1nc(-c2cccnc2)cs1]

072: 4-[(Diisopropylamino)-methyl]-N-[4-methyl-3-(4-pyridin-3-yl-thiazol-2-ylamino)-phenyl]-benzamide

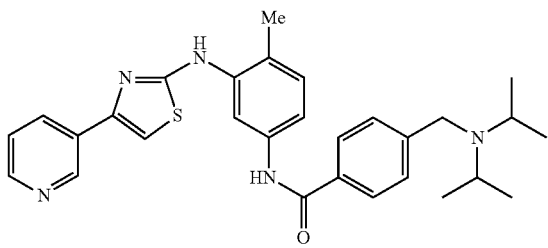 [SMILES: Cc1ccc(NC(=O)c2ccc(CN(C(C)C)C(C)C)cc2)cc1Nc1nc(-c2cccnc2)cs1]

073: {4-[4-Methyl-3-(4-pyridin-3-yl-thiazol-2-ylamino)-phenylcarbamoyl]-benzyl}-carbamic acid tert-butyl ester

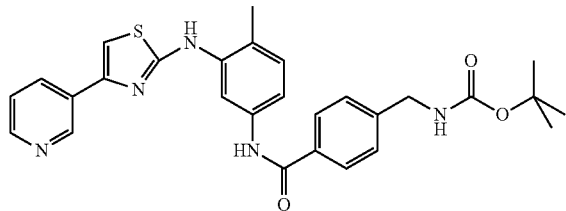 [SMILES: Cc1ccc(NC(=O)c2ccc(CNC(=O)OC(C)(C)C)cc2)cc1Nc1nc(-c2cccnc2)cs1]

074: 3-Fluoro-4-(4-methyl-piperazin-1-ylmethyl)-N-[4-methyl-3-(4-pyridin-3-yl-thiazol-2-ylamino)-phenyl]-benzamide

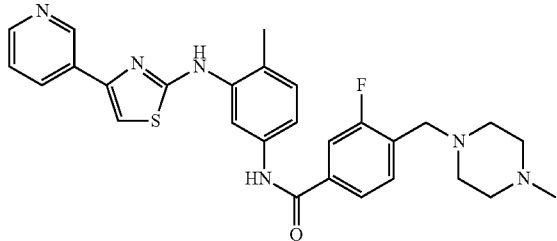 [SMILES: Cc1ccc(NC(=O)c2ccc(CN3CCN(C)CC3)c(F)c2)cc1Nc1nc(-c2cccnc2)cs1]

075: 4-(4-Methyl-piperazin-1-ylmethyl)-N-[4-methyl-3-(4-pyridin-3-yl-thiazol-2-ylmethyl)-phenyl]-3-trifluoromethyl-benzamide

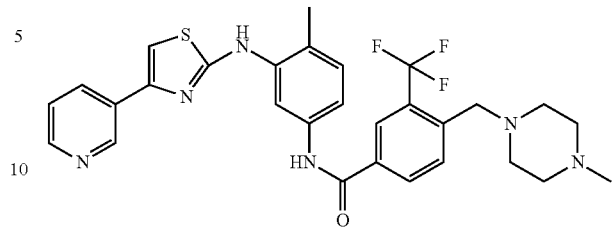

yellow crystals mp: 118-120° C.
$^1$H NMR (DMSO-d$^6$) δ=2.22 (s, 3H); 2.33 (s, 3H); 2.34-2.50 (m, 8H); 3.74 (s, 2H); 7.26 (d, J=8.3 Hz, 1H); 7.41-7.49 (m, 2H); 7.53 (s, 1H); 7.99 (d, J=8.0 Hz, 1H); 8.28-8.31 (m, 2H); 8.38 (d, J=7.9 Hz, 1H); 8.53 (dd, J=1.3 Hz, J=4.7 Hz, 1H); 8.68 (d, J=1.9 Hz, 1H); 9.21 (d, J=2.0 Hz, 1H); 9.53 (s, 1H); 10.49 (s, 1H)

076: 2,3,5,6-Tetrafluoro-4-(4-methyl-piperazin-1-ylmethyl)-N-[4-methyl-3-(4-pyridin-3-yl-thiazol-2-ylamino)-phenyl]-benzamide

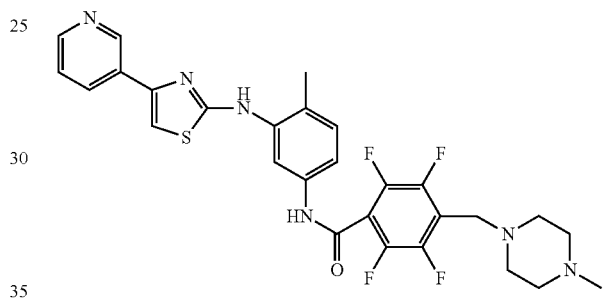

077: N-{3-[4-(4-Fluoro-phenyl)-thiazol-2-ylamino]-4-methyl-phenyl}-4-(4-methyl-piperazin-1-ylmethyl)-benzamide

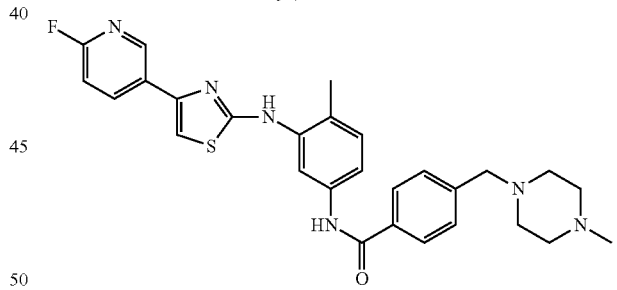

078: 3-Bromo-4-(4-methyl-piperazin-1-ylmethyl)-N-[4-methyl-3-(4-pyridin-3-yl-thiazol-2-ylamino)-phenyl]-benzamide

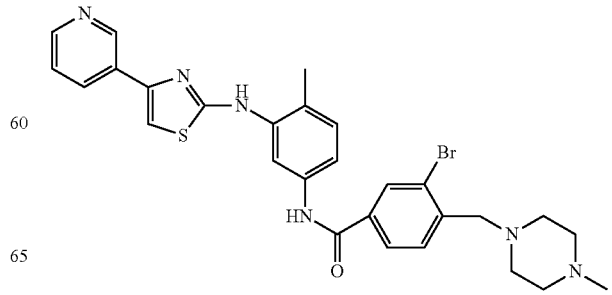

079: 3-Chloro-4-(4-methyl-piperazin-1-ylmethyl)-N-[4-methyl-3-(4-pyridin-3-yl-thiazol-2-ylamino)-phenyl]-benzamide

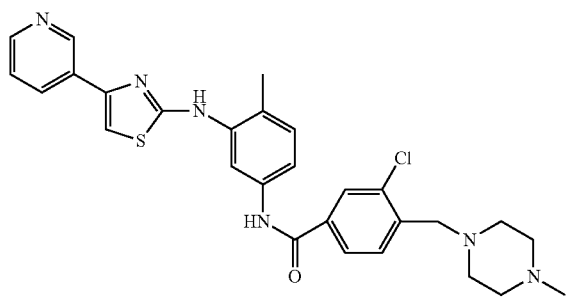 [SMILES: Cc1ccc(NC(=O)c2ccc(CN3CCN(C)CC3)c(Cl)c2)cc1Nc1nc(-c2cccnc2)cs1]

080: 4-(4-Methyl-piperazin-1-ylmethyl)-N-[4-methyl-3-(4-pyridin-4-yl-thiazol-2-ylamino)-phenyl]-benzamide

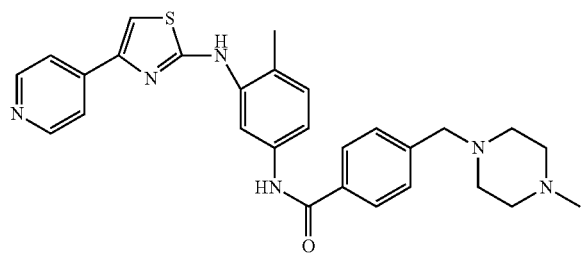 [SMILES: Cc1ccc(NC(=O)c2ccc(CN3CCN(C)CC3)cc2)cc1Nc1nc(-c2ccncc2)cs1]

081: N-{3-[4-(4-Cyano-phenyl)-thiazol-2-ylamino]-4-methyl-phenyl}-4-(4-methyl-piperazin-1-ylmethyl)-benzamide

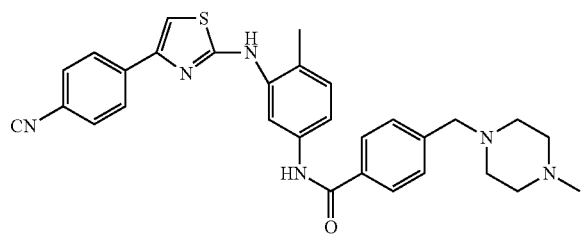

082: 4-[1-(4-Methyl-piperazin-1-yl)-ethyl]-N-[4-methyl-3-(4-pyridin-3-yl-thiazol-2-ylmethyl)-phenyl]-benzamide

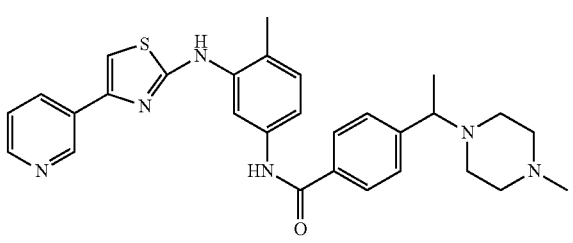 [SMILES: Cc1ccc(NC(=O)c2ccc(C(C)N3CCN(C)CC3)cc2)cc1Nc1nc(-c2cccnc2)cs1]

beige powder mp: 153-155° C.
$^1$H NMR (DMSO-d$^6$) δ=1.29 (d, J=6.6 Hz, 3H); 2.15 (s, 3H); 2.26 (s, 3H); 3.15-3.25 (m, 9H); 7.18 (d, J=8.4 Hz, 1H); 7.35-7.47 (m, 5H); 7.91 (d, J=8.2 Hz, 2H); 8.31 (d, J=8.0 Hz, 1H); 8.47 (dd, J=1.6 Hz, J=4.7 Hz, 1H); 8.60 (d, J=2.0 Hz, 1H); 9.15 (d, J=0.6, 1H); 9.45 (s, 1H); 10.18 (s, 1H)

083: 4-(1-Methoxy-ethyl)-N-[4-methyl-3-(4-pyridin-3-yl-thiazol-2-ylmethyl)-phenyl]-benzamide

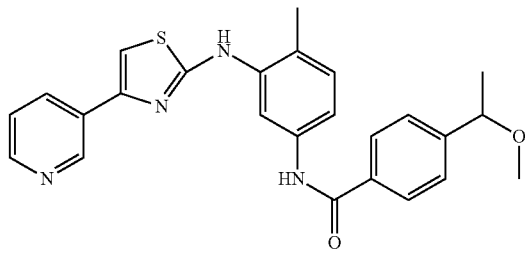 [SMILES: COC(C)c1ccc(C(=O)Nc2ccc(C)c(Nc3nc(-c4cccnc4)cs3)c2)cc1]

084: N-{4-Methyl-3-[4-(5-methyl-pyridin-3-yl)-thiazol-2-ylamino]-phenyl}-4-(4-methyl-piperazin-1-ylmethyl)-benzamide

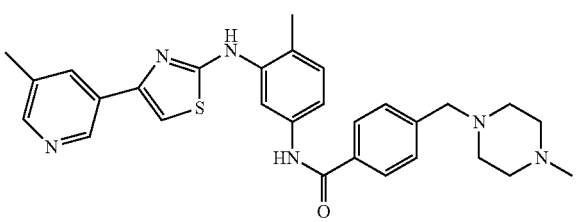

085: 3-Iodo-4-(4-methyl-piperazin-1-ylmethyl)-N-[4-methyl-3-(4-pyridin-3-yl-thiazol-2-ylmethyl)-phenyl]-benzamide

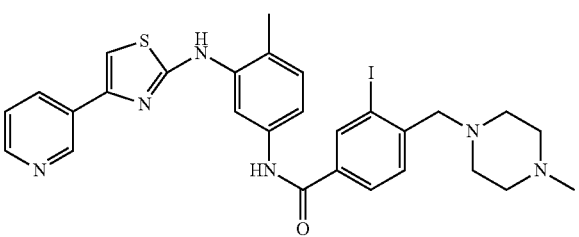 [SMILES: Cc1ccc(NC(=O)c2ccc(CN3CCN(C)CC3)c(I)c2)cc1Nc1nc(-c2cccnc2)cs1]

086: N-[4-Methyl-3-(4-pyridin-3-yl-thiazol-2-ylamino)-phenyl]-4-[3-(4-trifluoromethyl-phenyl)-ureidomethyl]-benzamide

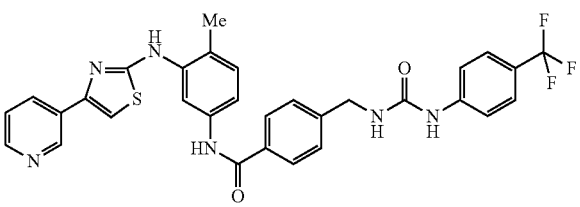 [SMILES: Cc1ccc(NC(=O)c2ccc(CNC(=O)Nc3ccc(C(F)(F)F)cc3)cc2)cc1Nc1nc(-c2cccnc2)cs1]

087: 3,5-Dibromo-N-[4-methyl-3-(4-pyridin-3-yl-thiazol-2-ylamino)-phenyl]-4-[(3-morpholin-4-yl-propylamino)-methyl]-benzamide

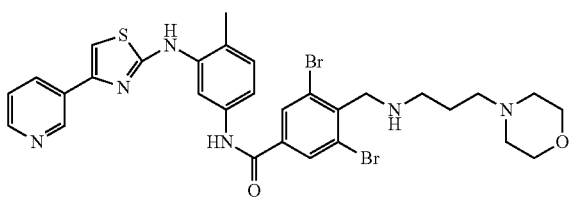 [SMILES: Cc1ccc(NC(=O)c2cc(Br)c(CNCCCN3CCOCC3)c(Br)c2)cc1Nc1nc(-c2cccnc2)cs1]

107: 3,5-Dibromo-N-[4-methyl-3-(4-pyridin-3-yl-thiazol-2-ylamino)-phenyl]-4-piperidin-1-ylmethyl-benzamide

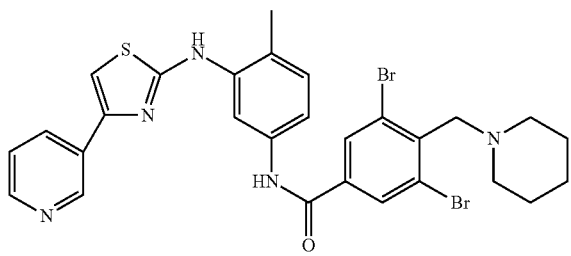 [SMILES: Cc1ccc(NC(=O)c2cc(Br)c(CN3CCCCC3)c(Br)c2)cc1Nc1nc(-c2cccnc2)cs1]

122: 4-(4-Methyl-piperazin-1-ylmethyl)-N-[4-methyl-3-(4-pyridin-2-yl-thiazol-2-ylamino)-phenyl]-benzamide

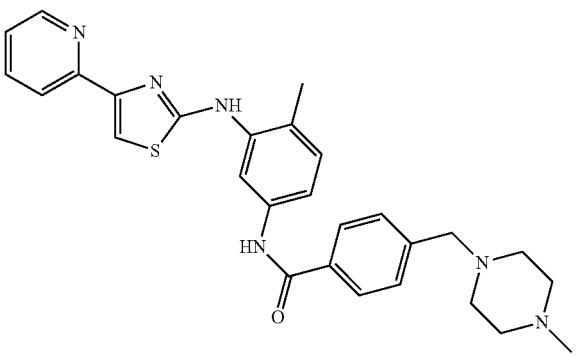 [SMILES: Cc1ccc(NC(=O)c2ccc(CN3CCN(C)CC3)cc2)cc1Nc1nc(-c2ccccn2)cs1]

111: N-{3-[4-(3-Fluoro-phenyl)-thiazol-2-ylamino]-4-methyl-phenyl}-4-(4-methyl-piperazin-1-ylmethyl)-benzamide

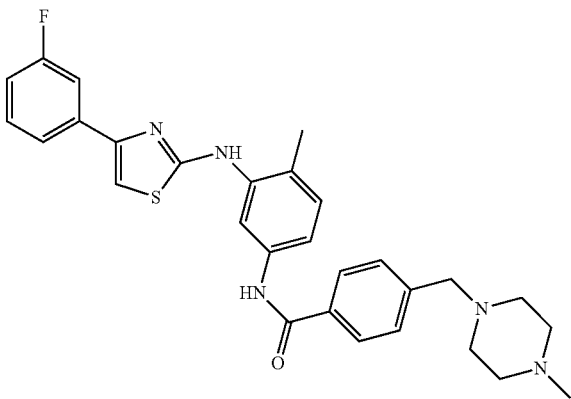 [SMILES: Cc1ccc(NC(=O)c2ccc(CN3CCN(C)CC3)cc2)cc1Nc1nc(-c2cccc(F)c2)cs1]

118: N-{3-[4-(2-Fluoro-phenyl)-thiazol-2-ylamino]-4-methyl-phenyl}-4-(4-methyl-piperazin-1-ylmethyl)-benzamides

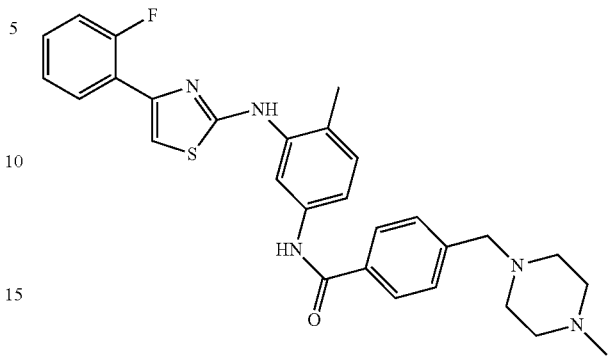

Among compounds of formula II, the invention is particularly embodied by the compounds wherein X is a -aryl-substituted group, corresponding to the 3-Disubstituted-amino-N-[3-(thiazol-2-ylamino)-phenyl]-benzamide family and the following formula II-5:

FORMULA II-5

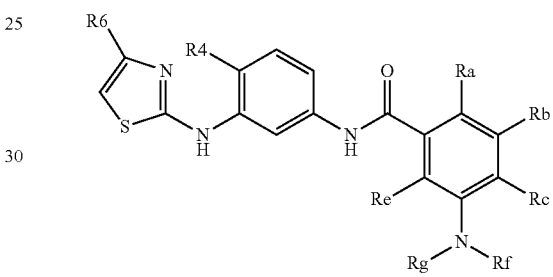

wherein Ra, Rb, Rc, Re, Rf, Rg are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality;

or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

or a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a COOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a CONRaRb, where Ra and Rb are a hydrogen or a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NHCOOR, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an $NRaOSO_2Rb$, where Ra and Rb are a linear or branched alkyl group containing from 1 to 10 carbon atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Ra, Rb, Rc, Re can also be halogen such as Cl, F, Br, I or trifluoromethyl;

$R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

Examples

088: 3-Dimethylamino-N-[4-methyl-3-(4-pyridin-3-yl-thiazol-2-ylamino)-phenyl]-benzamide

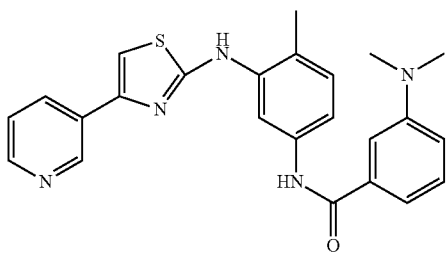 [SMILES: Cc1ccc(NC(=O)c2cccc(N(C)C)c2)cc1Nc1nc(-c2cccnc2)cs1]

beige powder mp: 197-198° C.
$^1$H NMR (DMSO-d$^6$): δ=2.32 (s, 3H); 3.03 (s, 6H); 6.97 (d, J=6.4 Hz, 1H); 7.23-7.56 (m, 7H); 8.37 (d, J=7.3 Hz, 1H); 8.53 (d, J=4.7 Hz, 1H); 8.63 (s, 1H); 9.20 (s, 1H); 9.48 (s, 1H); 10.15 (s, 1H)

089: 3-(4-Methyl-piperazin-1-yl)-N-[4-methyl-3-(4-pyridin-3-yl-thiazol-2-ylamino)-phenyl]-benzamide

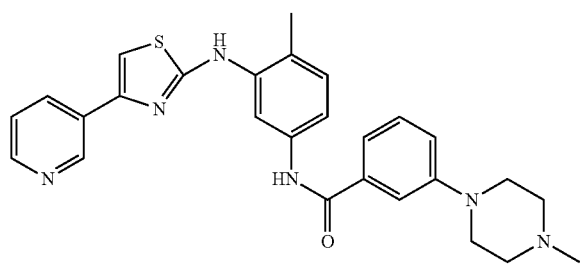 [SMILES: Cc1ccc(NC(=O)c2cccc(N3CCN(C)CC3)c2)cc1Nc1nc(-c2cccnc2)cs1]

beige powder mp: 274-246° C.
$^1$H NMR (DMSO-d$^6$) δ=2.23 (s, 3H); 2.24-2.30 (m, 4H); 3.22-3.27 (m, 4H); 7.07-7.20 (m, 2H); 7.36-7.53 (m, 6H); 8.31 (d, J=7.5 Hz, 1H); 8.47 (d, J=3.7 Hz, 1H); 8.58 (s, 1H); 9.12 (d, J=7.8 Hz, 1H); 9.44 (s, 1H); 10.12 (s, 1H)

090: N-[4-Methyl-3-(4-pyridin-3-yl-thiazol-2-ylamino)-phenyl]-3-morpholin-4-yl-benzamide

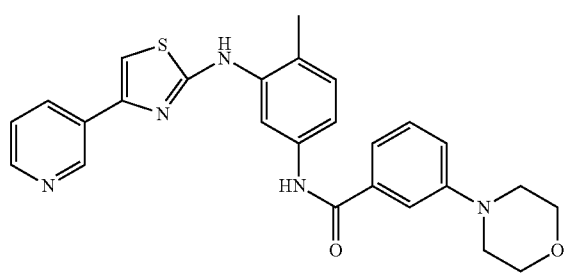 [SMILES: Cc1ccc(NC(=O)c2cccc(N3CCOCC3)c2)cc1Nc1nc(-c2cccnc2)cs1]

beige powder mp: 247-248° C.
$^1$H NMR (CDCl$_3$) δ=1.50 (s, 3H); 3.15-3.18 (m, 4H); 3.79-3.82 (m, 3H); 6.85 (s, 1H); 7.00-7.30 (m, 7H); 7.41 (s, 1H); 7.75 (s, 1H); 8.08 (d, J=7.9 Hz, 1H); 8.22 (d, J=1.7 Hz, 1H); 8.46 (dd, J=1.3 Hz, J=4.7 Hz, 1H); 9.01 (d, J=1.6 Hz, 1H)

Among the compounds of formula II, the invention is particularly embodied by the compounds wherein X is a —OR group, corresponding to the family [3-(Thiazol-2-ylamino)-phenyl]-carbamate and the following formula II-6

FORMULA II-6

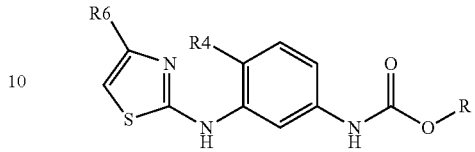

wherein R is independently chosen from an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with an heteroatom, notably a halogen selected from I, Cl, Br and F and/or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F and/or bearing a pendant basic nitrogen functionality;
R$^4$ is hydrogen, halogen or a linear or branched alkyl group containing from 1 to 10 carbon atoms, trifluoromethyl or alkoxy;
R$^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;
iv) H, a halogen selected from I, F, Cl or Br; NH2, NO2 or SO2-R, wherein R is a linear or branched alkyl group containing one or more group such as 1 to 10 carbon atoms, and optionally substituted with at least one heteroatom, notably a halogen selected from I, Cl, Br and F, and/or bearing a pendant basic nitrogen functionality.

Examples

097: [4-Methyl-3-(4-pyridin-3-yl-thiazol-2-ylamino)-phenyl]-carbamic acid isobutyl ester

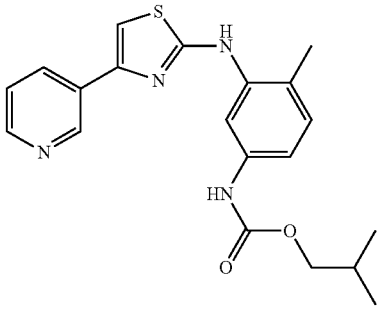 [SMILES: Cc1ccc(NC(=O)OCC(C)C)cc1Nc1nc(-c2cccnc2)cs1]

098: 2-(2-methyl-5-tert-butoxycarbonylamino)phenyl-4-(3-pyridyl)-thiazole

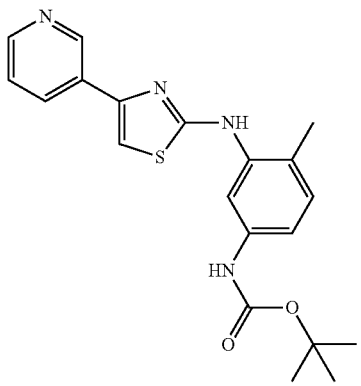 [SMILES: Cc1ccc(NC(=O)OC(C)(C)C)cc1Nc1nc(-c2cccnc2)cs1]

In a second embodiment, the invention is directed to a process for manufacturing a compound of formula I depicted above. This entails the condensation of a substrate of general formula 10 with a thiourea of the type 11.

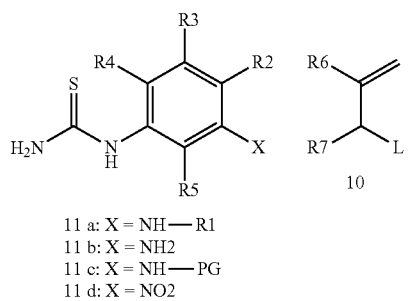

11 a: X = NH—R1
11 b: X = NH2
11 c: X = NH—PG
11 d: X = NO2

Substituent "L" in formula 10 is a nucleofugal leaving group in nucleophilic substitution reactions (for example, L can be selected from chloro, bromo, iodo, toluenesulfonyloxy, methanesulfonyloxy, trifluoromethanesulfonyloxy, etc., with L being preferentially a bromo group).

Group R1 in formula 11a corresponds to group R1 as described in formula I.

Group "PG" in formula 11c is a suitable protecting group of a type commonly utilized by the person skilled in the art.

The reaction of 10 with 1 a-d leads to a thiozole-type product of formula 12a-d.

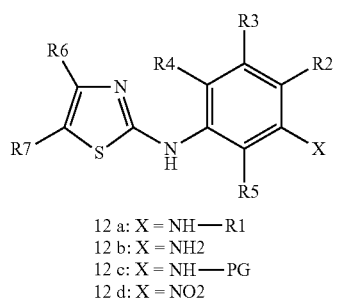

12 a: X = NH—R1
12 b: X = NH2
12 c: X = NH—PG
12 d: X = NO2

Formula 12a is the same as formula I. Therefore, R1 in 12a corresponds to R1 in formula I.

Formula 12b describes a precursor to compounds of formula I which lack substituent R1. Therefore, in a second phase of the synthesis, substituent R1 is connected to the free amine group in 12b, leading to the complete structure embodied by formula I:

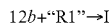

12b+"R1"→I

The introduction of R1, the nature of which is as described on page 3 for the general formula I, is achieved by the use of standard reactions that are well known to the person skilled in the art, such as alkylation, acylation, sulfonylation, formation of ureas, etc.

Formula 12c describes an N-protected variant of compound 12b. Group "PG" in formula 12c represents a protecting group of the type commonly utilized by the person skilled in the art. Therefore, in a second phase of the synthesis, group PG is cleaved to transform compound 12c into compound 12b. Compound 12b is subsequently advanced to structures of formula I as detailed above.

Formula 12d describes a nitro analogue of compound 12b. In a second phase of the synthesis, the nitro group of compound 12d is reduced by any of the several methods utilized by the person skilled in the art to produce the corresponding amino group, namely compound 12b. Compound 12b thus obtained is subsequently advanced to structures of formula I as detailed above.

Examples of Compound Synthesis

General: All chemicals used were commercial reagent grade products. Dimethylformamide (DMF), methanol (MeOH) were of anhydrous commercial grade and were used without further purification. Dichloromethane and tetrahydrofuran (THF) were freshly distilled under a stream of argon before use. The progress of the reactions was monitored by thin layer chromatography using precoated silica gel 60F 254, Fluka TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were realized on a 300 MHz Bruker spectrometer.

3-Bromoacetyl-pyridine, HBr Salt

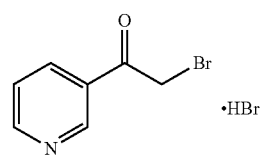

Dibromine (17.2 g, 108 mmol) was added dropwise to a cold (0° C.) solution of 3-acetyl-pyridine (12 g, 99 mmol) in acetic acid containing 33% of HBr (165 mL) under vigorous stirring. The vigorously stirred mixture was warmed to 40° C. for 2 h and then to 75° C. After 2 h at 75° C., the mixture was cooled and diluted with ether (400 mL) to precipitate the product, which was recovered by filtration and washed with ether and acetone to give white crystals (100%). This material may be recrystallised from methanol and ether.

IR (neat): 3108, 2047, 2982, 2559, 1709, 1603, 1221, 1035, 798 cm$^{-1}$—$^1$H NMR (DMSO-d$^6$) δ=5.09 (s, 2H, CH$_2$Br);

7.88 (m, 1H, pyridyl-H); 8.63 (m, 1H, pyridyl-H); 8.96 (m, 1H, pyridyl-H); 9.29 (m, 1H, pyridyl-H).

Methyl-[4-(1-N-methyl-piperazino)-methyl]-benzoate

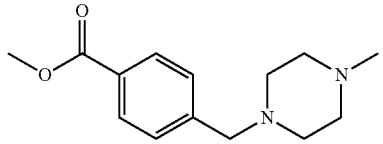

To methyl-4-formyl benzoate (4.92 g, 30 mmol) and N-methyl-piperazine (3.6 mL, 32 mmol) in acetonitrile (100 mL) was added dropwise 2.5 mL of trifluoroacetic acid. The reaction mixture was stirred at room temperature for 1 h. After slow addition of sodium cyanoborohydride (2 g, 32 mmol), the solution was left stirring overnight at room temperature. Water (10 mL) was then added to the mixture, which was further acidified with 1N HCl to pH=6-7. The acetonitrile was removed under reduced pressure and the residual aqueous solution was extracted with diethyl ether (4×30 mL). These extracts were discarded. The aqueous phase was then basified (pH>12) by addition of 2.5N aqueous sodium hydroxyde solution. The crude product was extracted with ethyl acetate (4×30 mL). The combined organic layers were dried over MgSO$_4$ and concentrated under reduced pressure to afford a slightly yellow oil which became colorless after purification by Kugelrohr distillation (190° C.) in 68% yield.

IR (neat): 3322, 2944, 2802, 1721, 1612, 1457, 1281, 1122, 1012—$^1$H NMR (CDCl$_3$) δ=2.27 (s, 3H, NCH$_3$); 2.44 (m, 8H, 2×NCH$_2$CH$_2$N); 3.53 (s, 2H, ArCH$_2$N); 3.88 (s, 3H, OCH$_3$); 7.40 (d, 2H, J=8.3 Hz, 2×ArH); 7.91 (d, 2H, J=8.3 Hz, 2×ArH)—$^{13}$C NMR (CDCl$_3$) δ=45.8 (NCH$_3$); 51.8 (OCH$_3$); 52.9 (2×CH$_2$N); 54.9 (2×CH$_2$N); 62.4 (ArCH$_2$N); 128.7 (2×ArC); 129.3 (2×ArC); 143.7 (ArC); 166.7 (ArCO$_2$CH$_3$)—MS CI (m/z) (%): 249 (M+1, 100%).

2-Methyl-5-tert-butoxycarbonylamino-aniline

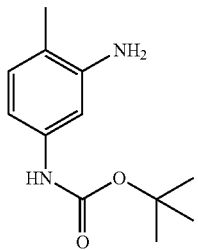 [SMILES: Cc1ccc(NC(=O)OC(C)(C)C)cc1N]

A solution of di-tert-butyldicarbonate (70 g, 320 mmol) in methanol (200 mL) was added over 2 h to a cold (−10° C.) solution of 2,4-diaminotoluene (30 g, 245 mmol) and triethylamine (30 mL) in methanol (15 mL). The reaction was followed by thin layer chromatography (hexane/ethyl acetate, 3:1) and stopped after 4 h by adding 50 mL of water. The mixture was concentrated in vacuo and the residue was dissolved in 500 mL of ethyl acetate. This organic phase was washed with water (1×150 mL) and brine (2×150 mL), dried over MgSO$_4$, and concentrated under reduced pressure. The resulting light brown solid was washed with small amounts of diethyl ether to give off-white crystals of 2-methyl-5-tert-butoxycarbonylamino-aniline in 67% yield.

IR (neat): 3359; 3246; 2970; 1719; 1609; 1557; 1173; 1050 cm$^{-1}$—$^1$H NMR (CDCl$_3$): δ=1.50 (s, 9H, tBu); 2.10 (s, 3H, ArCH$_3$); 3.61 (br s, 2H, NH$_2$); 6.36 (br s, 1H, NH); 6.51 (dd, 1H, J=7.9 Hz, 2.3 Hz, ArH); 6.92 (d, 1H, J=7.9 Hz, ArH); 6.95 (s, 1H, ArH)—$^{13}$C NMR (CDCl$_3$) δ=16.6 (ArCH$_3$); 28.3 (C(CH$_3$)$_3$); 80.0 (C(CH$_3$)$_3$); 105.2 (ArC); 108.6 (ArC); 116.9 (ArC); 130.4 (ArC—CH$_3$); 137.2 (ArC-NH); 145.0 (ArC—NH$_2$); 152.8 (COOtBu)

MS ESI (m/z) (%): 223 (M+1), 167 (55, 100%).

N-(2-methyl-5-tert-butoxycarbonylamino)phenyl-thiourea

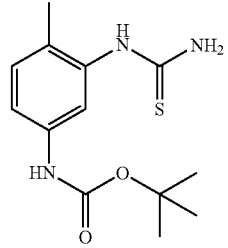 [SMILES: Cc1ccc(NC(=O)OC(C)(C)C)cc1NC(N)=S]

Benzoyl chloride (5.64 g, 80 mmol) was added dropwise to a well-stirred solution of ammonium thiocyanate (3.54 g, 88 mmol) in acetone (50 mL). The mixture was refluxed for 15 min, then, the hydrobromide salt of 2-methyl-5-tert-butoxycarbonylamino-aniline (8.4 g, 80 mmol) was added slowly portionswise. After 1 h, the reaction mixture was poured into ice-water (350 mL) and the bright yellow precipitate was isolated by filtration. This crude solid was then refluxed for 45 min in 70 mL of 2.5 N sodium hydroxide solution. The mixture was cooled down and basified with ammonium hydroxide. The precipitate of crude thiourea was recovered by filtration and dissolved in 150 mL of ethyl acetate. The organic phase was washed with brine, dried over Na$_2$SO$_4$, and concentrated under reduced pressure. The residue was purified by column chromatography (hexane/ethyl acetate, 1:1) to afford 63% of N-(2-methyl-5-tert-butoxycarbonylamino) phenyl-thiourea as a white solid.

IR (neat): 3437, 3292, 3175, 2983, 1724, 1616, 1522, 1161, 1053 cm$^{-1}$—$^1$H NMR (DMSO-d$^6$) δ=1.46 (s, 9H, tBu); 2.10 (s, 3H, ArCH$_3$); 3.60 (br s, 2H, NH$_2$); 7.10 (d, 1H, J=8.29 Hz, ArH); 7.25 (d, 1H, J=2.23 Hz, ArH); 7.28 (d, 1H, J=2.63 Hz, ArH); 9.20 (s, 1H, ArNH); 9.31 (s, 1H, ArNH)—$^{13}$C NMR (DMSO-d$^6$) δ=25.1 (ArCH$_3$); 28.1 (C(CH$_3$)$_3$); 78.9 (C(CH$_3$)$_3$); 116.6 (ArC); 117.5 (ArC); 128.0 (ArC); 130.4 (ArC-CH$_3$); 136.5 (ArC-NH); 137.9 (ArC-NH); 152.7 (COOtBu); 181.4 (C=S)—MS CI (m/z): 282 (M+1, 100%); 248 (33); 226 (55); 182 (99); 148 (133); 93 (188).

2-(2-methyl-5-tert-butoxycarbonylamino)phenyl-4-(3-pyridyl)-thiazole

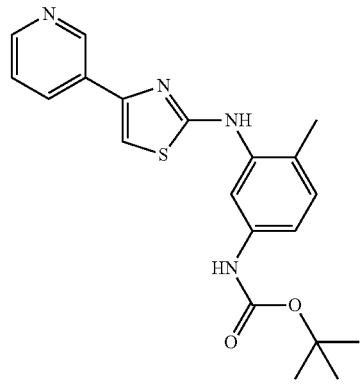 [SMILES: Cc1ccc(NC(=O)OC(C)(C)C)cc1Nc1nc(-c2cccnc2)cs1]

A mixture of 3-bromoacetyl-pyridine, HBr salt (0.81 g, 2.85 mmol), N-(2-methyl-5-tert-butoxycarbonylamino)phenyl-thiourea (0.8 g, 2.85 mmol) and $KHCO_3$ (~0.4 g) in ethanol (40 mL) was heated at 75° C. for 20 h. The mixture was cooled, filtered (removal of $KHCO_3$) and evaporated under reduced pressure. The residue was dissolved in $CHCl_3$ (40 mL) and washed with saturated aqueous sodium hydrogen carbonate solution and with water. The organic layer was dried over $Na_2SO_4$ and concentrated. Column chromatographic purification of the residue (hexane/ethyl acetate, 1:1) gave the desired thiazole in 70% yield as an orange solid IR (neat): 3380, 2985, 2942, 1748, 1447, 1374, 1239, 1047, 938—$^1$H NMR ($CDCl_3$) δ=1.53 (s, 9H, tBu); 2.28 (s, 3H, $ArCH_3$); 6.65 (s, 1H, thiazole-H); 6.89 (s, 1H); 6.99 (dd, 1H, J=8.3 Hz, 2.3 Hz); 7.12 (d, 2H, J=8.3 Hz); 7.35 (dd, 1H, J=2.6 Hz, 4.9 Hz); 8.03 (s, 1H); 8.19 (dt, 1H, J=1.9 Hz, 7.9 Hz); 8.54 (br s, 1H, NH); 9.09 (s, 1H, NH)—$^{13}$C NMR ($CDCl_3$) δ=18.02 ($ArCH_3$); 29.2 ($C(CH_3)_3$); 81.3 ($C(CH_3)_3$); 104.2 (thiazole-C); 111.6; 115.2; 123.9; 124.3; 131.4; 132.1; 134.4; 139.5; 148.2; 149.1; 149.3; 153.6; 167.3 (C=O)—MS CI (m/z) (%): 383 (M+1, 100%); 339 (43); 327 (55); 309 (73); 283 (99); 71 (311).

2-(2-methyl-5-amino)phenyl-4-(3-pyridyl)-thiazole

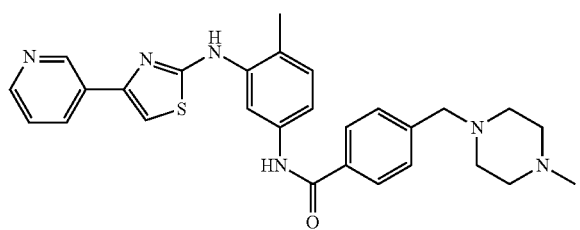 [SMILES: Cc1ccc(NC(=O)c2ccc(CN3CCN(C)CC3)cc2)cc1Nc1nc(-c2cccnc2)cs1]

2-(2-methyl-5-tert-butoxycarbonylamino)phenyl-4-(3-pyridyl)-thiazole (0.40 g, 1.2 mmol) was dissolved in 10 mL of 20% $TFA/CH_2Cl_2$. The solution was stirred at room temperature for 2 h, then it was evaporated under reduced pressure. The residue was dissolved in ethyl acetate. The organic layer was washed with aqueous 1N sodium hydroxide solution, dried over $MgSO_4$, and concentrated to afford 2-(2-methyl-5-amino)phenyl-4-(3-pyridyl)-thiazole as a yellow-orange solid in 95% yield. This crude product was used directly in the next step.

A 2M solution of trimethyl aluminium in toluene (2.75 mL) was added dropwise to a cold (0° C.) solution of 2-(2-methyl-5-amino)phenyl-4-(3-pyridyl)-thiazole (0.42 g, 1.5 mmol) in anhydrous dichloromethane (10 mL) under argon atmosphere. The mixture was warmed to room temperature and stirred at room temperature for 30 min. A solution of methyl-4-(1-N-methyl-piperazino)-methyl benzoate (0.45 g, 1.8 mmol) in anhydrous dichloromethane (1 mL) and added slowly, and the resulting mixture was heated at reflux for 5 h. The mixture was cooled to 0° C. and quenched by dropwise addition of a 4N aqueous sodium hydroxide solution (3 mL). The mixture was extracted with dichloromethane (3×20 mL) The combined organic layers were washed with brine (3×20 mL) and dried over anhydrous $MgSO_4$. (2-(2-methyl-5-amino)phenyl-4-(3-pyridyl)-thiazole) is obtained in 72% after purification by column chromatography (dichloromethane/methanol, 3:1)

IR (neat): 3318, 2926, 1647, 1610, 1535, 1492, 1282, 1207, 1160, 1011, 843—$^1$H NMR ($CDCl_3$) δ=2.31 (br s, 6H, $ArCH_3+NCH_3$); 2.50 (br s, 8H, $2×NCH_2CH_2N$); 3.56 (s, 2H, $ArCH_2N$); 6.89 (s, 1H, thiazoleH); 7.21-7.38 (m, 4H); 7.45 (m, 2H); 7.85 (d, 2H, J=8.3 Hz); 8.03 (s, 1H); 8.13 (s, 1H); 8.27 (s, 1H); 8.52 (br s, 1H); 9.09 (s, 1H, NH)—$^{13}$C NMR ($CDCl_3$) δ=17.8 ($ArCH_3$); 46.2 ($NCH_3$); 53.3 ($NCH_2$); 55.3 ($NCH_2$); 62.8 ($ArCH_2N$); 99.9 (thiazole-C); 112.5; 123.9; 125.2; 127.5; 129.6; 131.6; 133.7; 134.0; 137.6; 139.3; 142.9; 148.8; 149.1; 166.2 (C=O); 166.7 (thiazoleC-NH)—MS CI (m/z) (%): 499 (M+H, 100%); 455 (43); 430 (68); 401 (97); 374 (124); 309 (189); 283 (215); 235 (263); 121 (377); 99 (399).

In a third embodiment, the invention relates to a pharmaceutical composition comprising a compound as depicted above.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V. 60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biology of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
liquid gas systems (a liquefied gas is used as propellent gas (e.g. low-boiling FCHC or propane, butane) in a pressure container,
suspension aerosol (the active substance particles are suspended in solid form in the liquid propellent phase),
pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to unregulated c-kit transduction comprising administering an effective amount of a compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount of a compound depicted above to a mammal in need of such treatment.

The above described compounds are useful for manufacturing a medicament for the treatment of diseases related to unregulated c-kit transduction, including, but not limited to:
- neoplastic diseases such as mastocytosis, canine mastocytoma, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.
- tumor angiogenesis.
- metabolic diseases such as diabetes mellitus and its chronic complications; obesity; diabetes type II; hyperlipidemias and dyslipidemias; atherosclerosis; hypertension; and cardiovascular disease.
- allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.
- interstitial cystitis.
- bone loss (osteoporosis).
- inflammatory diseases such as rheumatoid arthritis, conjunctivitis, rheumatoid spondylitis, osteoarthritis, gouty arthritis and other arthritic conditions.
- autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.
- graft-versus-host disease or graft rejection in any organ transplantation including kidney, pancreas, liver, heart, lung, and bone marrow.
- Other autoimmune diseases embraced by the invention active chronic hepatitis and chronic fatigue syndrome.
- subepidermal blistering disorders such as pemphigus.
- Vasculitis.
- melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.
- CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia,
- neurodegenerative diseases including Alzheimer's disease, Parkinson's disease, Huntington's disease, the prion diseases, Motor Neurone Disease (MND), and Amyotrophic Lateral Sclerosis (ALS).
- substance use disorders as referred herein include but are not limited to drug addiction, drug abuse, drug habituation, drug dependence, withdrawal syndrome and overdose.
- Cerebral ischemia
- Fibrosis
- Duchenne muscular dystrophy Regarding mastocytosis, the invention contemplates the use of the compounds as defined above for treating the different categories which can be classified as follows:

The category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

The category II includes mastocytosis with an associated hematological disorder, such as a myeloproliferative or myelodysplastic syndrome, or acute leukemia. These malignant mastocytosis does not usually involve the skin The progression of the disease depends generally on the type of associated hematological disorder that conditions the prognosis.

The category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, the category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobactor freudii* and *Salmonella typhimurium*.

In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, deimatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

Example 1

In Vitro TK Inhibition Assays

Procedure

Experiments were performed using purified intracellular domain of c-kit expressed in baculovirus. Estimation of the kinase activity was assessed by the phosphorylation of tyrosine containing target peptide estimated by established ELISA assay.

Experimental Results on Tested Compounds

Result in Table 1 shows the potent inhibitory action of the catalytic activity of c-kit with an IC50<10 µM. Further experiments (not shown) indicates that at least one compound acts as perfect competitive inhibitors of ATP.

TABLE 1

| Compounds | In vitro Inhibition assay results c-kit IC50 (µM) |
|---|---|
| 066; 074; 078; 084; 012; 016; 073; 021; 088; 023; 025; 047; 048; 055; 049; 026; 087; 075; 089; 051; 082; 090; 060; 085; 052; 053; 096 | <10 µM |

Example 2

Ex Vivo TK Inhibition Assays

Procedures
C-Kit WT and Mutated C-Kit (JM) Assay
Proliferation Assays

Cells were washed two times in PBS before plating at $5 \times 10^4$ cells per well of 96-well plates in triplicate and stimulated either with hematopoietic growth factors (HGF) or without. After 2 days of culture, 37 Bq (1.78 Tbq/mmol) of [$_3$H] thymidine (Amersham Life Science, UK) was added for 6 hours. Cells were harvested and filtered through glass fiber filters and [$_3$H] thymidine incorporation was measured in a scintillation counter. For proliferation assay, all drugs were prepared as 20 mM stock solutions in DMSO and conserved at −80° C. Fresh dilutions in PBS were made before each experiment. DMSO dissolved drugs were added at the beginning of the culture. Control cultures were done with corresponding DMSO dilutions. Results are represented in percentage by taking the proliferation without inhibitor as 100%.

Cells

Ba/F3 murine kit and human kit, Ba/F3 mkitΔ27 (juxtamembrane deletion) are derived from the murine IL-3 dependent Ba/F3 proB lymphoid cells. The FMA3 and P815 cell lines are mastocytoma cells expressing endogenous mutated forms of Kit, i.e., frame deletion in the murine juxtamembrane coding region of the receptor-codons 573 to 579. The human leukaemic MC line HMC-1 expresses mutations JM-V560G;

Immunoprecipitation Assays and Western Blotting Analysis

For each assay, $5 \cdot 10_6$ Ba/F3 cells and Ba/F3-derived cells with various c-kit mutations were lysed and immunoprecipitated as described (Beslu et al., 1996), excepted that cells were stimulated with 250 ng/ml of rmKL. Cell lysates were immunoprecipitated with a rabbit immunserum anti murine KIT, directed against the KIT cytoplasmic domain (Rottapel et al., 1991). Western blot was hybridized either with the 4G10 anti-phosphotyrosine antibody (UBI) or with the rabbit immunserum anti-murine KIT or with different antibodies (described in antibodies paragraph). The membrane was then incubated either with HRP-conjugated goat anti mouse IgG antibody or with HRP-conjugated goat anti rabbit IgG antibody (Immunotech), Proteins of interest were then visualized by incubation with ECL reagent (Amersham).

Experimental Results

The experimental results for various compounds according to the invention using above-described protocols are set forth at Table 2:

TABLE 2

| Target | IC50 (μM) | Compounds |
|---|---|---|
| c-Kit WT | IC50 <10 μM | 002; 005; 006; 007; 008; 009; 010; 012; 017; 019; 020; 021; 023; 024; 025; 026; 028; 029; 030; 032; 042; 043; 045; 047; 048; 049; 050; 051; 052; 053; 054; 055; 056; 057; 059; 060; 061; 062; 063; 064; 065; 066; 067; 072; 073; 074; 075; 077; 078; 079; 080; 081; 082; 083; 084; 085; 086; 087; 088; 089; 090; 092; 093; 094; 095; 096; 097; 106; 105; 104; 103; 128; 129; 130; 131; 117; 110; 116; 124; 108; 122; 111; 113; 118; 107; |
| c-Kit JM Δ27 | IC50 <1 μM | 028; 074; 029; 009; 012; 073; 020; 042; 061; 065; 088; 025; 048; 049; 050; 089; 051; 082; 090; 083; 059; 052; 053; 066; 103; 067; 104; 078; 079; 105; 081; 084; 030; 010; 021; 043; 054; 062; 106; 023; 024; 064; 047; 055; 026; 087; 075; 085; 005; 077; 092; 060; 032; 017; 063; 093; 094; 095; 086; 093; 096; 108; 117; 122; 008; 080; 111; 118; 113; 007; 072; 019; 056; 057; 107; 097; |

Example 3

In Vivo Activity

Procedures
GIST
cells: Ba/F3 cells were transfected by c-kit gene having 427 mutation (GIST model). Ba/F3 expressing the mutated c-kit gene readily proliferate in the absence of IL3 or SCF and are tumorigenic in nude mice.

Protocol:
Mice were irradiated at J-1 (5Gy)
Tumor cells ($10^6$) were subcutaneously grafted at Jo
Tumor size were daily measured from J14
Number of survival mice were daily estimated
In this experimental model, the tumor size at J14 is about 20 mm$^3$ Treated mice received per os twice a day a dose of 100 mg/kg of one compound of formula II-3 during 5 days (from J26 to J30).

Rheumatoid Arthritis

The mice were pretreated with the compound of formula II-3 (2×, 12.5 mg/kg) for two days (day −2, day −1) before induction of arthritis. Arthritis was induced by ip injection of 150-ul serums at days 0 and 2. The treatment with the compound (2×, 12.5 mg/kg) was continued for 14 days. The control mice were injected with, 1% PBS before the induction of arthritis and during the course of the disease. Ankle thickness and arthritis score was evaluated for 15 days. Arthritis Score: Sum of scores of each limb (0 no disease; 1 mild swelling of paw or of just a few digits; 2 clear joint inflammation; 3 severe joint inflammation) maximum score=12. Table 3A and Table 3B show the number of mice used in this study. Two sets of experiments were done with different number of mice, one with 4 mices the other with 8 mices.

TABLE 3 A

| Treated Mice | C57Bl/6 |
|---|---|
| 2x, 12.5 mg/Kg | 6 |

TABLE 3 B

| Controls | C57Bl/6 |
|---|---|
| 2X, 1% PBS | 6 |

Histology

At the end of the experiment the hind limbs were collected. The skin of the limb was removed and the limbs were subsequently fixed in 2% Para formaldehyde.

Experimental Results
GIST

Treated mice (with one compound of formula II-3) displays significant decrease of tumor size at J30 and J33 compared to control.

When administered per os, one tested compound of the formula II-3 displays a significant antitumor activity against tumors cells expressing c-kit Δ27.

RA

A compound of the formula II-3 has demonstrated significant activity in the in vivo mouse model of arthritis. Results are shown on FIGS. 1, 2, 3, 4.

FIGURE LEGENDS

FIG. 1: Effect of the compound in serum transfer experiments, Protocol, ip daily treatment with the compound (2×12.5 mg/kg) and on days −2 and −1, set of experiment with 4 mices (T: treated, C: control)

Figure 2:
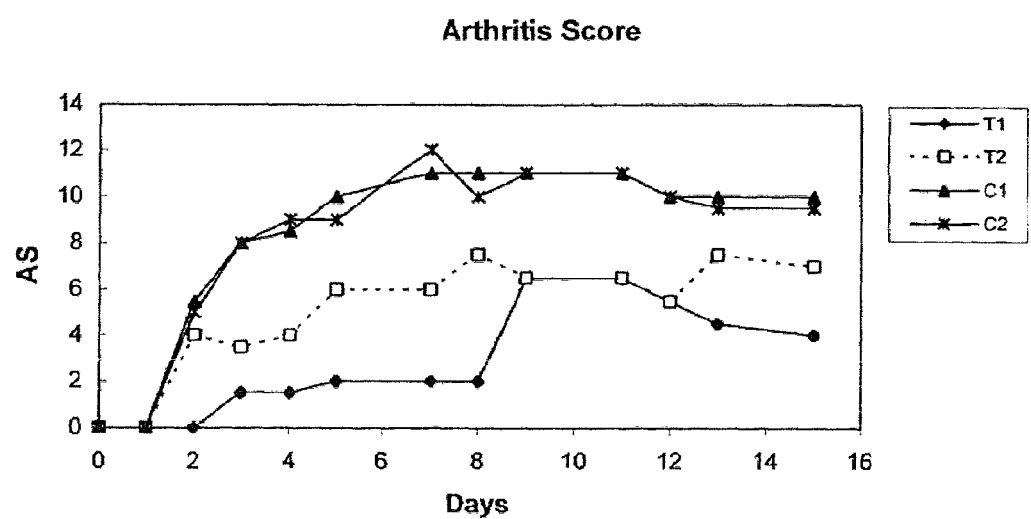

FIG. 2: Effect of the compound in serum transfer experiments, Protocol, ip daily treatment with the compound (2×12.5 mg/kg) and on days −2 and −1, set of experiment with 4 mices (T: treated, C: control)

Figure 3:
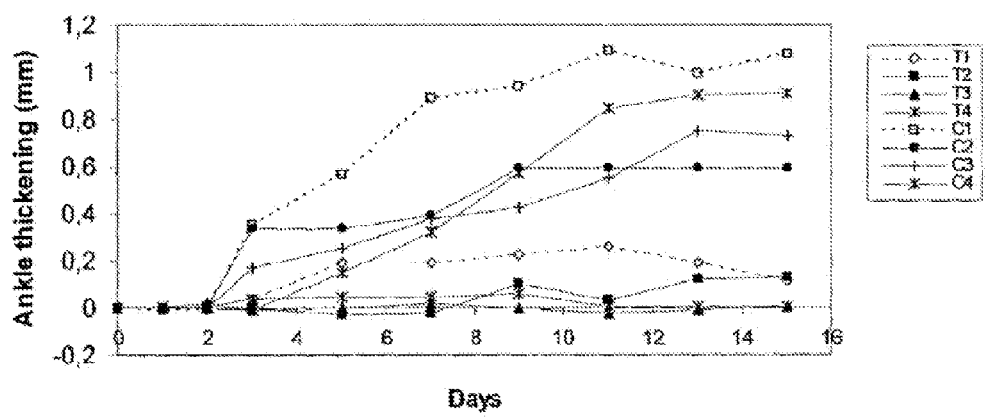

FIG. 3: Effect of the compound in serum transfer experiments, Protocol, ip daily treatment with the compound (2×12.5 mg/kg) and on days −2 and −1, set of experiment with 8 mices (T: treated, C: control)

Figure 4:
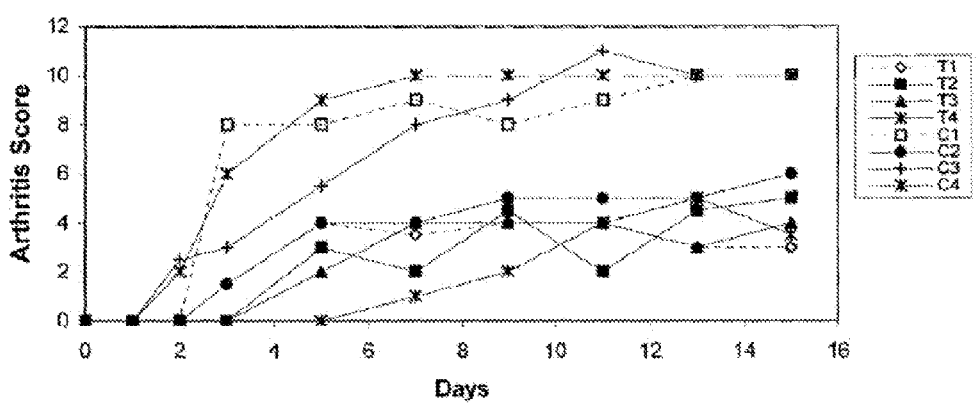

FIG. 4: Effect of the compound in serum transfer experiments, Protocol, ip daily treatment with the compound (2×12.5 mg/kg) and on days −2 and −1, set of experiment with 8 mices (T: treated, C: control)

Treatment of GIST with Masitinib

In view of the above results, the invention further relates to a method for the treatment of GIST.

The method of the invention comprises the administration of a tyrosine kinase inhibitor of formula I above including any embodiment and variant thereof. The method of the invention relates in particular to the administration of masitinib, or pharmaceutically acceptable salt thereof.

DEFINITION AND TERMINOLOGY

Gastrointestinal stromal tumours (GIST) are usually defined as specific, generally Kit positive and Kit and PDG-FRA mutation-driven mesenchymal tumours of the gastrointestinal (GI) tract with a set of characteristic histological features including spindle cell, epithelioid and rarely pleomorphic morphology.

Description of GIST

GIST are rare sarcoma tumours affecting the digestive tract and nearby structures within the abdomen. They arise from interstitial cells of Cajal or their precursors. GISTs are usually attached to the outside of the involved organ, growing outward.

Primary GIST may occur anywhere along the gastrointestinal tract from the oesophagus to the anus. The most frequent site is the stomach (~55%) followed by the duodenum and small intestine (~30%), oesophagus (~5%), rectum (~5%), colon (~2%) and rare other locations.

Occasionally, primary GIST may develop in the supporting membranes of the abdominal organs (peritoneum, mesentery, omentum), the liver, the pancreas, the ovaries, the uterus and the prostate. Because these primary GISTs do not arise directly from the GI tract, they are sometimes called extra-gastrointestinal stromal tumour. GISTs not encased in the peritoneal membranes are called retroperitoneal.

The most common sites for metastasis are the liver and the abdominal membranes (peritoneum, mesentery, omentum). GISTs rarely spread to lymph nodes, but they may occasionally affect local abdominal lymph nodes. Unusual sites of metastasis include lung and bones as well as pelvic sites such as the ovaries. Extremely rare sites include breast and muscle tissue.

Incidence of GIST

Of all adult cancers, sarcomas represent about 1%; GIST is one of the most common of about 50 types of sarcomas. Age-adjusted incidence could be estimated about 6 to 15 per million.

Risk Factors for GIST

No environmental or behavioural risk factors contributing to GIST have been identified. They appear to be no relationship between diet and lifestyle and the incidence of GIST.

Affected Population for GIST

GISTs most commonly affect older people, usually over 50. They have a broad distribution with no gender or racial predilection.

Symptoms of GIST

The most common presentation of GIST is gastrointestinal bleeding that may be acute or chronic insidious bleeding leading to anaemia.

Many patients with smaller tumours don't have symptoms. Larger tumours may cause symptoms that are generally related to the increased mass being accommodated in the abdominal cavity (digestive discomfort, sensation of abdominal fullness or abdominal pain); such symptoms would not necessarily be different from those of other types of tumours.

Sometimes larger tumours may be detectable by palpation. Some patients may experience vomiting or diarrhoea; bowel obstruction may occur. In case GIST perforate the stomach or gut lining and bleed into the GI tract, resulting in black or tarry stools and occasionally of vomiting of blood. Anaemia may result from chronic bleeding, leading to fatigue.

Though such symptoms are possible, most of them are rather indistinct and merely related to the additional mass. Therefore, many GISTS are found incidentally.

Diagnosis of GIST

A final diagnosis can only be made immunohistochemically. GIST became a clear diagnosis only in 1998, when it was found that nearly all GIST cells express Kit and that many GIST show mutations in the Kit gene [1, 2]. About 70% of GIST are composed of spindle cells, while about 20% are composed of epithelioid cells and the other 10% show mixed cells of both spindle and epithelioid types. GIST can also contain activating mutations of the PDGFRA gene [3].

Kit-negative GIST are uncommon but about 5% do not stain for Kit. Several markers have been identified to help diagnose Kit-negative GIST (PKC beta and/or DOG1).

The pathologist can estimate proliferation; the higher the proliferation, the faster the tumour is growing and the more aggressively it can be expected to grow (if not resected) or to recur or metastasize (if removed).

Major negative factors include large size (>5 cm), high mitotic index and grossly positive resection margins. Other factors with poor prognosis include tumour rupture, high cellularity, tumour necrosis, presence of metastases or invasion and certain types of Kit mutations.

Factors that are correlated with an improved prognosis include gastric location, diameter less than 2 cm, low mitotic index and absence of tumour spillage with complete gross resection.

Kit and PDGFRA Mutations in GIST

Mutations in the Kit gene that are relevant for GIST are found in exon 9, 11, 13 and 17, with mutation in exon 11 being the most frequent. Mutation in Kit can be found in about 80% of GIST.

About 8% of GISTs have a Kit WT but show mutations in PDGFRA. The PDGFRA gene is very similar to the Kit gene, and PDGFRA mutations have been found in exons corresponding to those of Kit.

Mutations of Kit and of PDGFRA are mutually exclusive in primary, untreated GIST.

Secondary Mutations in Drug Resistance in GIST Treatment

Newly acquired secondary mutations have been shown to confer drug resistance to imatinib. They often appear in new metastases of tumours being treated with imatinib and in sections of otherwise responding tumours that start to grow.

Long-term success is limited by the development of imatinib resistance via secondary mutation or clonal selection.

Management/Treatments of GIST

Excision of the tumour, when feasible is the treatment of choice. Patients whose tumours are unresectable or who have metastatic disease are treated with Kit/PDGFRA tyrosine kinase inhibitors such as imatinib. This oral treatment is generally well tolerated and the majority of patients achieve complete or partial remission.

Recent data suggest that the response of GIST patients to tyrosine kinase inhibitor varies by the specific mutation displayed by their tumours.

There is a stronger and longer-duration response to imatinib for patients with mutation in exon 11 than for those with mutations in exon 9 or for patients with GIST negative for Kit expression.

Response to sunitinib in patients who had grown resistant to imatinib was better for patients with exon 9 mutation.

Remaining Problems in GIST Treatments

Imatinib represented a revolution for the treatment of patients with GIST, by improving the outcome of patients with advanced GIST from pre-imatinib 2-year survival rate of 25% to about 70% after its introduction. However, patients eventually progress and the majority of patients will die from their disease, despite an increase of imatinib daily dose from 400 mg to 800 mg or a switch to second-line therapy (e.g. sunitinib). These progressions are considered as late progression, to be distinguished from early progression (occurring within 3 to 6 months of treatment, in patients who never have a response to treatment).

Late progression is defined as progressions occurring in patients who had a response or a progression-free survival (PFS) over 3 to 6 months after initiation of imatinib treatment. In this case, progression results from resistance mechanisms developing under imatinib pressure, mostly the occurrence of secondary Kit mutation (in 50-70% of patients showing late progression), predominantly in the region encoding the part of the receptor in the vicinity of the ATP-binding site or the kinase activating loop [4]. These mutations change Kit conformation, and the ability of imatinib to bind to and inhibit Kit is reduced. These secondary mutations appear with a higher frequency in Kit with exon 11 mutation than in Kit with exon 9 mutation.

Results from a phase 3 study (345 patients receiving the initial dose of 400 mg/day) show median PFS of 18 months (95% CI [16-21]) and a 2-year PFS rate of 46% (95% CI [36-47]). Median overall survival (OS) was 55 months (95% CI [47-62]) with 2-year survival of 72% (95% CI [67-77]) and 3-year survival of ~61% [5].

A study exploring the relationship between imatinib plasma levels and long-term clinical outcomes has shown that imatinib trough plasma levels seem to be correlated with clinical benefits, including longer Time-to-Progression (TTP) for patients with higher trough plasma levels (>1,110 ng/mL) than for those with lower trough levels, and objective response [6]. In addition, sex was not a significant covariate but the average imatinib trough level in women seemed about 25% higher than in men [6]. This was consistent with the body weight difference between men and women, suggesting that the dosage of imatinib in mg/day provides lower plasma levels and therefore potentially lowered efficacy to patients with higher body weight. These lower doses of imatinib could favour the rapid emergence of imatinib-resistant clones, thus progression.

The invention also aims to solve the technical problem of providing a new treatment for GIST, and particularly a treatment overcoming the remaining problems in GIST treatments of the prior art.

The invention further aims to solve the technical problem of providing a method for the treatment of a subject with a proliferative disease wherein a tyrosine kinase is affected, in particular where said subject has cells showing a mutant kit and/or mutant PDGFRA gene(s).

In particular, the invention aims to solve the technical problem of providing a method for the treatment of a subject with GIST.

The invention further aims to solve the technical problem of providing a method for the long-term treatment of a subject with GIST.

The invention further aims to solve the technical problem of providing a method for the treatment of a subject with non-pre-treated, inoperable, locally advanced or metastatic GIST.

The invention further aims to solve the technical problem of providing a method for the treatment of a subject having cells resistant to a treatment of a proliferative disease wherein tyrosine kinase is affected. In particular the invention aims to provide a treatment for a subject having cells resistant to a tyrosine kinase inhibitor, and in particular to imatinib.

The invention further aims to solve the technical problem of providing a new pharmaceutical use or method involving masitinib or a pharmaceutically acceptable salt thereof.

The invention aims to achieve all the above mentioned goals while meeting industrial, in particular pharmaceutical, needs notably in term of drug efficacy, safety and regulatory requirements.

The present invention solves the above mentioned technical problems.

In particular, the invention relates to a method for the treatment of a subject with GIST, wherein said method comprises the administration of an effective amount of masitinib or a pharmaceutically acceptable salt thereof, in particular of masitinib mesylate, to said subject.

According to one embodiment, said treatment is for treating or preventing cancer cell metastasis.

Advantageously, said treatment comprises the oral administration of masitinib or a pharmaceutically acceptable salt thereof, in particular of masitinib mesylate, to a subject in need thereof.

A preferred effective amount of masitinib or a pharmaceutically acceptable salt thereof, in particular of masitinib mesylate, is a daily dose below 18 mg/kg of subject weight. A preferred effective amount of masitinib or a pharmaceutically acceptable salt thereof, in particular of masitinib mesylate, is a daily dose comprised between 1 mg/kg and 15 mg/kg of subject weight.

Advantageously, said treatment comprises the administration of masitinib or a pharmaceutically acceptable salt thereof, in particular of masitinib mesylate, to a subject in need thereof, at a dose from 3 mg/kg/day to 15 mg/kg/day, from 6 mg/kg/day to 12 mg/kg/day, in particular 7.5 mg/kg/day, 9 mg/kg/day or 10.5 mg/kg/day. Masitinib is given in mg/kg/day with respect to the subject (particularly patient) weight. Unexpectedly, these low doses of the compound of the invention provide good results with respect to the treatment of GIST in human patients.

It is meant by the compound of the invention: masitinib or a pharmaceutically acceptable salt thereof, in particular of masitinib mesylate.

The effective dose is preferably administered to a subject depending on their weight. This enables a more effective treatment.

Accordingly, the present invention relates to a method for the treatment of a subject with GIST, wherein said effective amount of masitinib or a pharmaceutically acceptable salt thereof, in particular of masitinib mesylate, is a daily dose depending on the patient weight.

Advantageously in the method of the invention the dose is administered in two intakes a day ("bis in die", i.e. bid). Dosing in two intakes reduces gastrointestinal adverse reactions without affecting efficacy.

The invention further relates to a method for the treatment of a subject with GIST wherein said subject having cells showing a native kit and/or PDGFRA gene(s), comprising the administration of masitinib or a pharmaceutically acceptable salt thereof, in particular of masitinib mesylate.

The invention further relates to a method for the treatment of a subject with a proliferative disease wherein a tyrosine kinase is affected, said subject having cells showing a mutant kit and/or mutant PDGFRA gene(s), comprising the administration of masitinib or a pharmaceutically acceptable salt thereof, in particular of masitinib mesylate.

According to one embodiment, said mutation is a mutation conferring resistance to a tyrosine kinase, and in particular to imatinib drug treatment. Where reference is made to imatinib, it refers in especially to Imatinib mesylate, or Gleevec, or STI-571; as produced by Novartis, Basel, Switzerland.

The invention further relates to a method for the long-term treatment of a subject with GIST, wherein said method comprises the administration on a long-term of an effective amount of masitinib or a pharmaceutically acceptable salt thereof, in particular of masitinib mesylate, to said subject.

A long-term treatment is preferably a treatment over more than 12 months, and preferably more than 2 years. The treatment of the present invention extends the PFS (Progression-Free Survival).

The invention further relates to a method for the treatment of a subject with non-pre-treated, inoperable, locally advanced or metastatic GIST, wherein said method comprises the administration of an effective amount of masitinib or a pharmaceutically acceptable salt thereof, in particular of masitinib mesylate, to said subject. The invention relates in particular to a first-line therapy method wherein masitinib or a pharmaceutically acceptable salt thereof, in particular masitinib mesylate, is administered to a patient in need thereof, and in particular to a patient, whose tumour is not treatable by surgery.

A preferred effective amount of masitinib or a pharmaceutically acceptable salt thereof, in particular of masitinib mesylate, is a daily dose from 6 mg/kg to 9 mg/kg of subject weight, preferably from 7 to 8 mg/kg of subject weight, and more preferably a dose of 7.5 mg/kg of subject weight. This dose is particularly preferred for a first-line therapy.

It has been discovered by the inventors that masitinib or a pharmaceutically acceptable salt thereof, in particular masitinib mesylate, inhibits the growth of cells resistant to another c-kit inhibitor, and in particular to imatinib-resistant cells.

Accordingly, the invention relates to a method wherein masitinib or a pharmaceutically acceptable salt thereof, in particular masitinib mesylate, is administered in combination with another tyrosine kinase inhibitor, and in particular in combination with imatinib.

The invention also relates to a second-line therapy method, wherein masitinib or a pharmaceutically acceptable salt thereof, in particular masitinib mesylate, is administered to a patient in need thereof, and in particular to a patient, whose tumour is resistant to another tyrosine kinase inhibitor, and in particular to imatinib.

A second-line therapy is a treatment that is given when initial treatment (first-line therapy) doesn't work, or stops working.

A preferred effective amount of masitinib or a pharmaceutically acceptable salt thereof, and in particular of masitinib mesylate, is a daily dose from 10.5 to 15 mg/kg of subject weight, preferably from 11.5 to 13.5 mg/kg of subject weight, and more preferably is a daily dose of 12.5 mg/kg of subject weight. This dose is particularly preferred for a second-line therapy.

Accordingly, the invention relates to a method of treatment of a patient in need thereof, wherein said method comprises a first-line treatment comprising the administration to said patient of a tyrosine kinase inhibitor, and in particular imatinib, and as a second line treatment the administration of masitinib or a pharmaceutically acceptable salt thereof, in particular masitinib mesylate.

The invention further relates to a method for the treatment of a subject having cells resistant to a treatment of a proliferative disease wherein tyrosine kinase is affected, said treatment comprises the administration of a tyrosine kinase inhibitor other than masitinib, said method comprising the steps of:
 a. identifying in a subject a cell resistance to a treatment by a tyrosine kinase inhibitor other than masitinib of a proliferative disease wherein tyrosine kinase is affected;
 b. Administering masitinib or a pharmaceutically acceptable salt thereof, in particular masitinib mesylate, to said subject.

The invention relates in particular to the treatment of a human being. Thus a subject to the treatment is in particular a human patient.

The invention further relates to masitinib or a pharmaceutically acceptable salt thereof, in particular masitinib mesylate as a medicament in a method as described above or below, without particular limitation, and including the examples and drawings.

The invention further relates to a pharmaceutical composition comprising masitinib or a pharmaceutically acceptable salt thereof, in particular masitinib mesylate, for a method as described above or below, without particular limitation, and including the examples and drawings.

According to a particular embodiment, the composition of the invention is an oral composition.

Advantageously, said composition is in the form of a plurality of unit doses for administering an effective daily dose of masitinib or a pharmaceutically acceptable salt thereof, in particular of masitinib mesylate to a human patient in need thereof, wherein said dose is administered in pharmaceutical composition comprising below 3000 mg, more particularly between 1 mg and 2500 mg, and more particularly the dose is from 25 mg to 2000 mg. A preferred dose is from 50 mg to 150 mg, more preferably from 80 to 120 mg, and even more preferably 100 mg, for a first-line treatment. A preferred dose is from 150 mg to 400 mg, more preferably from 180 to 300 mg, and even more preferably 200 mg, for a second-line treatment.

The doses described in the invention provide advantageously plasma levels high enough to inhibit Kit WT, Kit mutant forms involved in GIST and PDGFRA. In particular, weight-adjusted doses potentially provide all patients with the same masitinib plasma levels.

The invention further relates to masitinib or a pharmaceutically acceptable salt thereof, in particular masitinib mesylate, as an inhibitor of Kit and PDGFRA mutants for the treatment of a disease with kit and/or PDGFRA mutants. In particular masitinib or a pharmaceutically acceptable salt thereof, in particular masitinib mesylate, is an inhibitor of kit mutants with mutation in exon 9, and/or 11, and/or 13, and/or 17. In particular masitinib or a pharmaceutically acceptable salt thereof, in particular masitinib mesylate, is an inhibitor of PDGFRA mutants with mutation in exon 12, and/or 14, and/or 18.

As is known to the person skilled in the art, various forms of excipients can be used adapted to the mode of administration and some of them can promote the effectiveness of the active molecule, e.g. by promoting a release profile rendering this active molecule overall more effective for the treatment desired.

The pharmaceutical compositions of the invention are thus able to be administered in various forms, more specially for example in an injectable, pulverizable or ingestible form, for example via the intramuscular, intravenous, subcutaneous, intradermal, oral, topical, rectal, vaginal, ophthalmic, nasal, transdermal or parenteral route. A preferred route is oral administration. The present invention notably covers the use of a compound according to the present invention for the manufacture of pharmaceutical composition.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V. 60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biology of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et al., U.S. Pat. No. 4,615,699 and Campbell et al., U.S. Pat. Nos. 4,460,372 and 4,379,454), dimethyl sulfoxide (U.S. Pat. No. 3,740,420 and U.S. Pat. No. 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:

liquid gas systems (a liquefied gas is used as propellent gas (e.g. low-boiling FCHC or propane, butane) in a pressure container, suspension aerosol (the active substance particles are suspended in solid form in the liquid propellent phase), pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

The invention is explained below with more details:
Masitinib has the following formula:

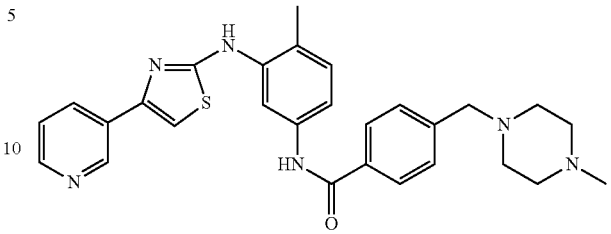

This compound is also known under reference AB1010.

The drug product is a tyrosine kinase inhibitor developed by AB Science that does not yet have a designated trade name, but referred to as AB1010. In this document we refer to the drug product by the name of its active pharmaceutical ingredient, masitinib. For human clinical trials all doses are expressed in terms of masitinib (molecular formula: $C_{28}H_{30}N_6OS$; relative molecular mass of 498.7), which is also known as the free base of masitinib. The investigational medicinal product contains the mesylate salt of masitinib, which is also known as masitinib mesylate (molecular formula: $C_{29}H_{34}N_6O_4S_2$; relative molecular mass of 549.8). The use of a salt form provides a good solubility and drug bioavailability. According to the invention the mesylate salt of masitinib is preferred.

Masitinib has a Higher Affinity for the Targets Specific to GIST (Kit WT or Mutated and PDGFRA)

Pre-clinical studies have shown that masitinib is a potent inhibitor of the targets specific to GIST, with better affinity than imatinib [7] which is incorporated herein by reference in its entirety. A summary of the results is presented in Table 1 below:

TABLE 1

| In vitro inhibitory properties of masitinib and imatinib on cell proliferation | | |
|---|---|---|
| Cell proliferation assay ($IC_{50}$) | masitinib | imatinib |
| Human Kit WT | 150 nM | 100-200 nM |
| Human Kit exon 9 | 100 nM | ~200 nM |
| Human Kit exon 11 | 3 nM | 27 nM |
| Human Kit exon 13 | 40 nM (GIST 882 cells) | 120 nM (GIST 882 cells) |
| PDGFRA | 250 nM | 1 µM |

Masitinib is Efficient Against Cell Lines that are Rendered Resistant to Imatinib HMC-1 α155 cells (a human mast cell line expressing Kit with the mutation V560G) were rendered resistant to imatinib by exposing them to 1 µM imatinib until exponential growth was observed, indicating that the cells had become resistant. HMC-1 is a human mast cell line derived from a patient with mast cell leukaemia. The cell line used in this study, HMC-1 α155, is a clone derived from the original population expressing endogenous Kit bearing the mutation Val 560 to Gly. Cells were placed in a medium containing 0.2 and 1 µM of AB1010 or imatinib. The medium used in this case was a RPMI medium containing L-glutamine (Cambrex cat #12-702F) supplemented with 100 U/mL penicillin and 100 µg/mL streptomycin (Cambrex 100X penicilline/streptomycine mixture cat #17-602E), and with 10% v/v foetal calf serum (AbCys Lot S02823S1800) which has been previously heatinactivated 30 minutes at 56° C. (RPMI 10). The medium containing the drugs was replaced with fresh one every 3-4 days. The cells were maintained in these conditions for several weeks and until exponential growth was observed, indicating that the cells had become drug resistant. Resistant cells lines were then tested for their sensitivity to masitinib and imatinib using apoptosis assay [8]. The principle behind the method for apoptosis assay by Propidium Iodide Staining (PI staining) is as follows: during apoptosis, DNA breakup causes small fragments of DNA to be free in the nucleus. Following appropriate elution with citrate buffer, these fragments are lost from the nucleus. As these cells now have a lower DNA content, subsequent staining with a DNA binding dye will reveal these cells in the sub-G1 region.

Figure 6:
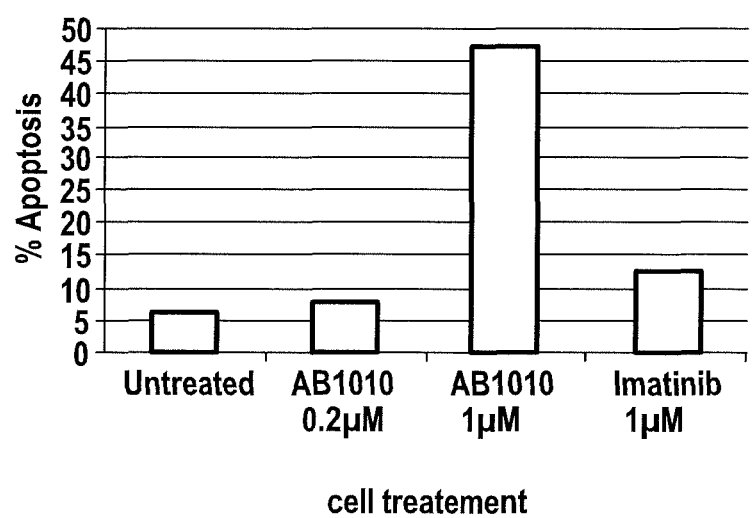

More than 45% of imatinib-resistant HMC-1 α155 cells were in apoptosis when exposed to 1 μM masitinib (FIG. 6). Thus imatinib-resistant cells significantly retain sensitivity to masitinib.

The % apoptosis represents the percentage of cells in apoptose with respect to overall cells.

Masitinib has Anti-Metastatic Properties Possibly Due to its Interaction with the FAK Pathway Data from pre-clinical and clinical studies both in dogs and humans suggests that masitinib reduces the number of patients developing metastases while under treatment. Since masitinib has been shown to reduce FAK activity, and since FAK has been involved in cell proliferation and migration, it is thought that this reduced risk to develop metastases under masitinib could be due to its action on FAK pathway.

In vitro, masitinib mesilate potently inhibits the GIST related c-Kit gain-of-function mutant V559D (exon 11), (Dubreuil et al., 2009—[7]). However, the extent of long-term survival observed in patients treated with masitinib, especially in comparison to other tyrosine kinase inhibitors (e.g. imatinib), far exceeds expectations. That is to say, this gain in efficacy cannot be explained solely by masitinib's superior inhibition of c-Kit, or inhibition of other individual kinase targets. Surprisingly, it would seem, without wishing to be bound by the theory, that concomitant processes contribute to masitinib's efficacy in GIST including, but not restricted to: masitinib's anti-mastocyte activity through targeting wild-type c-Kit, and indirectly therefore inhibition of the array of mediators they release; inhibition of mast cell degranulation through Lyn and Fyn inhibition, key components of the transduction pathway leading to mast cell IgE induced degranulation; inhibition of the FAK pathway; down-regulation of the Wnt/β-catenin signalling pathway. Thus, masitinib appears to exert an anticancer (GIST) action that extends beyond its inherent tyrosine kinase inhibition profile.

Figure 5:
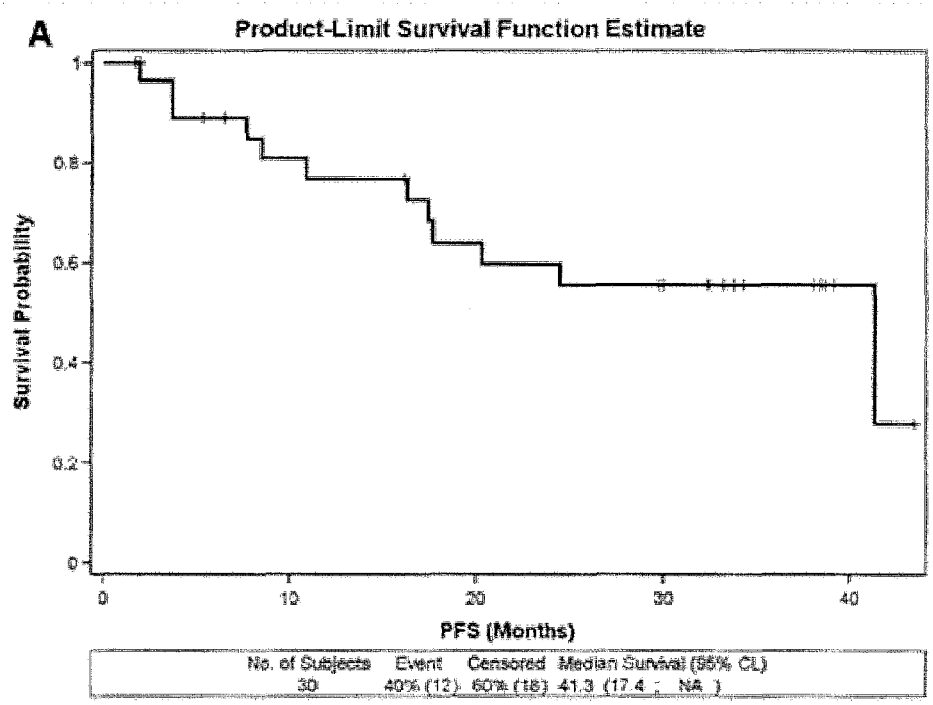
Figure 5:
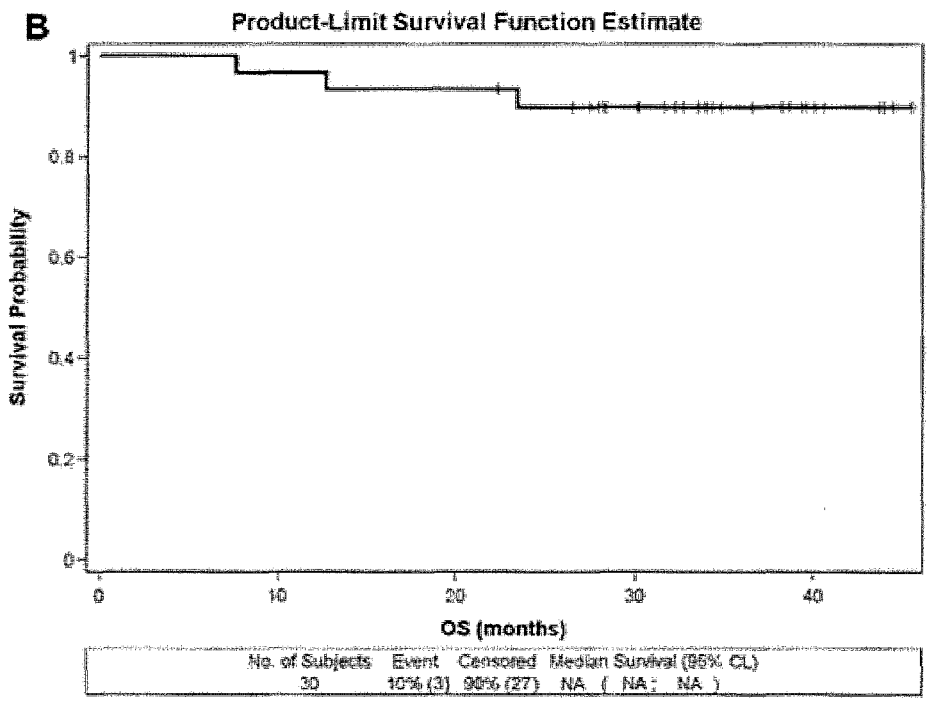

In the drawings:

FIG. 5: Kaplan-Meier analyses of progression-free survival (A) and overall survival (B).

FIG. 6: Diagram showing results of the % apoptosis by different KIT inhibitors (AB1010 and imatinib) versus control (untreated) on cells resistant to imatinib.

Examples

The following example illustrates the invention, but is not, however, intended to limit the scope of the invention in any way. Other test models known as such to the person skilled in the pertinent art can also determine the beneficial effects of the use of masitinib mesylate, or salts thereof.

An open-label, multicenter, non-randomised, phase 2 clinical trial was conducted to evaluate the efficacy and safety of masitinib mesylate in patients with advanced GIST.

Methods; Patients: Patients enrolled in this study were aged over 18 years with inoperable, non-pretreated, histologically proven locally advanced or metastatic, c-Kit positive GIST. Each patient had measurable tumour lesions according to response evaluation criteria in solid tumours (RECIST) [9] and an Eastern Cooperative Oncology Group (ECOG) performance status of ≦2. Exclusion criteria included: inadequate organ function defined via blood tests, severe liver or cardiac failure, and severe neurological or psychiatric disorders. Patients receiving a concomitant treatment within 4 weeks before inclusion, and pregnant or lactating women were also excluded.

Methods; Treatment: oral masitinib, supplied as 100 and 200 mg tablets, was administered daily at 7.5 mg/kg/day, in two intakes during meals. The 30 patients included received a mean dose of 7.1±0.8 mg/kg/day of masitinib; the median dose was 7.2 mg/kg/day; the range was 3.5 to 8.7 mg/kg/day; Q1 and Q3 were 6.9 and 7.6 mg/kg/day, respectively. This does not deviate significantly from the dose of 7.5 mg/kg/day planned by the protocol.

The chemical name is 4-(4-methylpiperazin-1-ylmethyl)-N-[4-methyl-3-(4-pyridin-3ylthiazol-2-ylamino) phenyl] benzamide-mesylate methane sulfonic acid salt, and the chemical formula is $C_{28}H_{30}N_6OS \cdot CH_4O_3S$. Masitinib used in these studies was synthesised by either Archemis (Decines Charpieu, (France) or Syngene-Biocon (Bangalore, India). For detailed procedure refer to patent WO/2008/098949. AB1010 is also manufactured by AB Science, S.A. (France), or by Prestwick Chemical, Inc. (France). The chemical structure was confirmed by nuclear magnetic resonance, mass spectrometry, ultraviolet and infrared spectrometry, and elemental analysis. Masitinib is practically insoluble in 0.1 M NaOH and n-hexane, slightly soluble in ethanol and propylene glycol, soluble in water, and freely soluble in 0.1 M HCl and dimethylsulfoxide. The compound, a white powder, was prepared according to the art to provide tablets. Tablet containing masitinib was used for each experiment.

Methods; Efficacy and Safety assessment: safety was assessed for all patients receiving at least one dose of masitinib with toxicity graded according to the NCI CTCAE v3.0 classification. All adverse events (AEs), including abnormal serology or haematology, were recorded regardless of causality.

The primary efficacy endpoint was response rate (RR) after 2 months of masitinib treatment according to RECIST, using Computed Tomography (CT). Secondary efficacy endpoints were the evaluation of metabolic response [10] using [$^{18}$F]-fluorodeoxyglucose-Positron Emission Tomography (FDG-PET) and assessment of disease control rate, PFS and OS. For each patient, all efficacy parameters were recorded on the first day of treatment (baseline) prior to administration of masitinib, then on weeks 2, 4, 8, and 16, and every 12 weeks thereafter (extension phase).

Time-to-event analyses were calculated from the date of first masitinib intake to the date of event (documented progression or death). Patients who had not progressed at the date of last tumor assessment were censored at that date for PFS. Patients alive at the time of the analysis were censored at the date of last contact for OS.

Methods; Statistical analyses: Simon minimax two-stage design was used for this prospective, multicenter, single-group, phase II trial. Fourteen patients were initially enrolled, with recruitment of an additional ten patients being dependent on the occurrence of at least one objective RECIST response. This population was further extended to a total of 30 patients to ensure a sufficient evaluable population for all end-points; the type I(α) error was 5% (two-sided) for all analyses. Quantitative variables were described by the number of filled and missing data, mean, standard deviation, median, minimum and maximum Qualitative variables were described by the number of missing data and, for each modality, frequency and percentage (referring to filled data). Time-to-event data were described using Kaplan-Meier (KM) estimates. The median was provided with its 95% confidence interval (95% CI). PFS rates were given every 6 months with KM estimates. All data analyses and reporting procedures used SAS v9.1 in a Windows XP operating system environment.

Results; Patient characteristics: between June 2005 and April 2007, 30 patients were enrolled from five centres across France. Patient characteristics at inclusion are summarized in Table 2. At the cut-off date of April 2009, the median follow-up duration was 33.7 months (range 7.7-45.4 months). All analyses are reported for the intent-to-treat population (ITT), defined as all enrolled patients (N=30). Two protocol deviations were revealed following pathology review, with two patients having been misdiagnosed as having GIST; one had a low grade endometrial stromal tumour and the other had an aggressive fibromatosis.

Four patients terminated prematurely before the fourth month: one patient for progressive disease (PD), one on the investigator's decision and two patients for AEs (non treatment-related grade 3 paresis; and treatment-related, grade 3 cheilitis and skin toxicity). During the extension period, 13 patients terminated the study: one patient for protocol violation (endometrial stromal tumour), eight patients for disease progression, two patients for AEs (one died from non treatment-related post-surgical complication and the other had treatment-related, grade 3 psoriasis), and two patients for other reasons (one patient developed a metastatic prostate cancer necessitating systemic chemotherapy and one discontinued therapy after radiofrequency ablation of liver metastasis).

TABLE 2

Demographics and clinical characteristics of patients

| Parameter | | ITT Population (N = 30) |
|---|---|---|
| Age (years) | Mean ± SD | 57 ± 14 |
| | Median | 58 |
| | Range | 34-82 |
| Sex, N (%) | Female | 12 (40%) |
| | Male | 18 (60%) |
| Weight (kg) | Mean ± SD | 75 ± 15 |
| | Median | 75 |
| | Range | 51-115 |
| ECOG performance status, N (%) | 0 | 23 (77%) |
| | 1 | 7 (23%) |
| Previous treatments/ medication for GIST | Surgery | 21 (70%) |
| | Biopsy | 4 (13%) |
| | Other | 2 (7%) |
| c-Kit status | Positive | 29 (96.7%) |
| | Negative | 1 (3.3%) |
| Time since diagnosis (months) | Mean ± SD | 22 ± 28 |
| | Median | 13 |
| | Range | 0-131 |

Results; Safety assessment: Safety analyses were performed on the ITT population (Table 3). All patients reported at least one treatment-related AE; 14/30 patients (47%) experienced at least one grade 3 treatment-related AE, of which rash was the most frequent at 3/30 patients (10%); and 1/30 patient (3.3%) reported one grade 4 AE (skin exfoliation). A total of 14 serious adverse events (SAE) were experienced by 8/30 patients (27%), three of which were treatment-related (worsening of a concomitant psoriasis and anaemia). The most frequent treatment-related toxicities per patient were: asthenia (83%), diarrhoea (57%), eye oedema (47%), nausea (47%), muscle spasms (40%), cutaneous rash (40%), abdominal pain (33%), pruritus (33%), vomiting (23%), upper abdominal pain (23%) and peripheral oedema (20%). Treatment-related oedemas (all types) were experienced by 21/30 patients (70%).

Six patients (20%) had their dose reduced by 100 or 200 mg/day (three patients each), following grade 3-4 AEs, and 16/30 patients (53.3%) had treatment interruption for more than 8 days. Reasons for treatment interruptions were non-haematological AEs for 13/30 patients (43%) (treatment-related for twelve of them), treatment-related haematological toxicity for 1/30 patient (3%), and surgery for 2/30 patients (6.7%). The most frequent treatment-related, non-haematological AEs leading to interruptions were skin toxicity, oedema and asthenia. Thirteen out of thirty patients (43%) were still undergoing treatment with masitinib at the cut-off date (12 at the same initial dose), with treatment duration from 26.5 to 45.4 months.

TABLE 3

Frequent adverse events (>10%) in patients receiving masitinib, and their suspected relationship to masitinib

| Number (%) of patients (N = 30) | Suspected* | | All causalities | |
|---|---|---|---|---|
| | All grades | G3 + G4 | All grades | G3 + G4 |
| Haematological events | | | | |
| Anaemia | 4 (13.3%) | 1 (3.3%) | 6 (20.0%) | 1 (3.3%) |
| Neutropenia | 5 (16.7%) | 2 (6.7%) | 5 (16.7%) | 2 (6.7%) |
| Non-haematological events | | | | |
| Asthenia | 25 (83.3%) | 1 (3.3%) | 27 (90.0%) | 1 (3.3%) |
| Diarrhoea | 17 (56.7%) | 1 (3.3%) | 18 (60.0%) | 1 (3.3%) |
| Abdominal Pain | 10 (33.3%) | 1 (3.3%) | 16 (53.3%) | 2 (6.7%) |
| Nausea | 14 (46.7%) | | 15 (50.0%) | |
| Eye Oedema | 14 (46.7%) | 1 (3.3%) | 14 (46.7%) | 1 (3.3%) |
| Muscle Spasms | 12 (40.0%) | | 12 (40.0%) | |
| Rash | 12 (40.0%) | 3 (10.0%) | 12 (40.0%) | 3 (10.0%) |
| Pruritus | 10 (33.3%) | 1 (3.3%) | 11 (36.7%) | 1 (3.3%) |

TABLE 3-continued

Frequent adverse events (>10%) in patients receiving masitinib, and their suspected relationship to masitinib

| Number (%) of patients (N = 30) | Suspected* All grades | Suspected* G3 + G4 | All causalities All grades | All causalities G3 + G4 |
|---|---|---|---|---|
| Vomiting | 7 (23.3%) | | 10 (33.3%) | |
| Abdominal Pain Upper | 7 (23.3%) | | 9 (30.0%) | |
| Oedema Peripheral | 6 (20.0%) | | 8 (26.7%) | |
| Eyelid Oedema | 7 (23.3%) | | 7 (23.3%) | |
| Erythema | 5 (16.7%) | | 6 (20.0%) | |
| Mucosal Inflammation | 5 (16.7%) | 1 (3.3%) | 5 (16.7%) | 1 (3.3%) |
| Dry Skin | 4 (13.3%) | | 4 (13.3%) | |
| Lacrimation Increased | 4 (13.3%) | | 4 (13.3%) | |
| Myalgia | 4 (13.3%) | | 4 (13.3%) | |

*Suspected: treatment related or not assessable; G3: grade 3 AE; G4: grade 4 AE.

Results; Response to treatment: during the Simon first stage, 4/14 patients had a confirmed PR after 2 months of treatment, instigating the study's Simon second stage. Efficacy results are presented in Table 4. Among the ITT population there were: 6/30 PR (20%), 23/30 SD (76.7%) and 1/30 PD (3.3%) after 2 months of masitinib treatment. Best response (RECIST) was analyzed until the cut-off date: complete response (CR), PR, SD and PD were recorded for 1/30 (3.3%), 15/30 (50%), 13/30 (43.3%), and 1/30 (3.3%) patients, respectively. The overall response rate (CR+PR) was 16/30 (53.3%) patients (95% CI [34.3; 71.7]) with a disease control rate (CR+PR+SD) of 29/30 (96.7%) patients (95% CI [82.8; 99.9]). Median time to first objective response was 5.6 months (range: 0.8-23.8 months).

Metabolic response was assessed for 17/30 patients (56.7%), of which 3/30 patients (10%) had a negative FDG-PET at baseline. Of the 13/30 (43.3%) and 14/30 patients (47.7%) who were evaluable after 1 and 2 months of treatment, respectively: 9/13 (69.2%) had a partial metabolic response (PMR) and 4/13 (30.8%) had a stable metabolic disease (SMD) after 1 month; whilst 3/14 (21.4%) had a complete metabolic response (CMR), 9/14 (64.3%) had a PMR, and 2/14 (14.3%) had a SMD, after 2 months. The metabolic response rate (CMR+PMR) after 2 months of treatment was 12/14 (85.7%) patients (95% CI [57.2; 98.2]).

TABLE 4

Response rates

| Response (RECIST); n (%) | 2 months (N = 30) | Best Response (N = 30) |
|---|---|---|
| CR | 0 (0.0%) | 1 (3.3%) |
| PR | 6 (20.0%) | 15 (50.0%) |
| CR + PR | 6 (20.0%) | 16 (53.3%) |
| [95% CI] | [7.7; 38.6] | [34.3; 71.7] |
| SD | 23 (76.7%) | 13 (43.3%) |
| CR + PR + SD | 29 (96.7%) | 29 (96.7%) |
| [95% CI] | [82.8; 99.9] | [82.8; 99.9] |
| PD | 1 (3.3%) | 1 (3.3%) |

| Metabolic response | At 1 month (N = 13) | At 2 months (N = 14) |
|---|---|---|
| CMR | 0 (0.0%) | 3 (21.4%) |
| PMR | 9 (69.2%) | 9 (64.2%) |
| CMR + PMR | 9 (69.2%) | 12 (85.7%) |
| [95% CI] | [38.6-90.9] | [57.2-98.2] |
| SMD | 4 (30.8%) | 2 (14.3%) |

CR: complete response, PR: partial response; CR + PR: overall response rate; SD: stable disease; CR + PR + SD: disease control rate; PD: progressive disease; CMR: complete metabolic response, PMR: partial metabolic response; CMR + PMR: metabolic response rate; SMD: stable metabolic disease.

Results; Time-to-event analysis: the analysis revealed 12 events (11 progressions and one death) with 18/30 patients (60%) censored for PFS: six patients withdrew from the study without progression and 12 progression-free patients were still receiving masitinib at the cut-off date. The estimated 6-month, 1-year, 2-year and 3-year PFS rates were 88.9% (95% CI [69.4; 96.3]), 76.8% [55.3; 88.9], 59.7% [37.9; 76.0] and 55.4% [33.9; 72.5], respectively (Table 5). Median PFS was 41.3 months [17.4 months; not reached] according to KM analysis (FIG. 5A). Median OS was not reached (FIG. 5B and Table 5), with 1-year survival rate of 96.7% [78.6; 99.5], and 2- and 3-year survival rates each at 89.9% [71.8; 96.6].

TABLE 5

PFS, PFS rates, OS and OS rates

| PFS | |
|---|---|
| Median | 41.3 months |
| [95% CI] | [17.4-NR] |
| PFS rate (%) [95% CI] | |
| 6 months | 88.9 [69.4; 96.3] |
| 12 months | 76.8 [55.3; 88.9] |
| 18 months | 64.0 [42.0; 79.5] |
| 24 months | 59.7 [37.9; 76.0] |
| 30 months | 55.4 [33.9; 72.5] |
| 36 months | 55.4 [33.9; 72.5] |
| 42 months | 27.7 [2.0; 65.7] |
| OS | |
| Median | NR |
| [95% CI] | [NR; NR] |
| OS rates (%) [95% CI] | |
| 12 months | 96.7 [78.6; 99.5] |
| 24 months | 89.9 [71.8; 96.6] |
| 36 months | 89.9 [71.8; 96.6] |

PFS: progression-free survival; OS: overall survival; NR: not reached.

Results; Mutational analysis: biopsy material was collected from 29/30 patients (96.7%) to assess their c-Kit status. Sufficient biopsy material was available to perform mutational analysis for 15/30 patients (50%): 10/30 patients (33.3%) had a GIST harbouring a c-Kit exon 11 mutation, 1/30 patient (3.3%) had double c-Kit exon 11 and 13 mutations, 3/30 patients (10%) had a WT c-Kit, and 1/30 patient (3.3%) had a GIST harbouring the PDGFRα (or PDGFRA) mutation (D842V).

Discussion; Imatinib has dramatically improved the outcome of patients with advanced GIST, becoming the model for targeted therapy in solid tumours [11-13]. However, despite near optimal compliance in the majority of patients and extended administration of imatinib [14], the risk of secondary progression due to acquired resistance to imatinib persists over time [15, 16]. This highlights the need for new strategies in non-pre-treated advanced GIST to increase the rate of complete remission and the duration of progression arrest rate.

It has been shown that some patients benefit from a higher than the standard imatinib dose, suggesting that individualized treatment could be a critical option in the initial management of advanced GIST patients. This is evidenced by imatinib at 800 mg/day producing improved PFS, as compared to the standard dose of 400 mg/day [17], in patients whose GIST harbours an exon 9 mutation [18, 19]; the relationship between imatinib plasma levels and progression [6]; and the fact that one third of patients progressing under imatinib at 400 mg/day clearly benefited from the higher dose regimen [13, 20]. In contrast to imatinib's fixed dosing strategy, masitinib has been developed with patient weight-adjusted dosing in mind [21]. Given its higher selectivity for c-Kit [7], a patient-optimized dose of masitinib could possibly provide a significant therapeutic benefit; although dose increments smaller than the 100 mg used in for this study are likely to be required to achieve such optimization.

As expected with the selectivity profile of masitinib [7], no cardiac side-effects have been observed to date. Occurrences of the most common masitinib-related haematological AEs (neutropenia and anaemia) were substantially lower compared to imatinib at standard dose [12]. The most frequently reported masitinib-related, non-haematological AEs were similar to those reported with imatinib in front-line treatment, with the exception of rash and abdominal pain that occurred at a higher frequency for masitinib [12]. In general, AEs occurred early during the course of treatment, which is consistent with the known safety profile of tyrosine kinase inhibitors [22, 23]; the majority of AEs showing a clear decrease in frequency for the 24/30 patients (80%) treated beyond 6 months (data not shown). The implication here is that treatment tolerance is likely to improve after the initial 6 months, thereby, making masitinib more appropriate for any long-term treatment regimen. At the cut-off date, 12/30 patients (40%) were still receiving masitinib at the same initial daily dose.

Early resistance to imatinib has been defined as progression occurring within the first 6 months of treatment in patients who showed no response. It is observed in 10-15% of patients and appears to result from intrinsic factors present before treatment start [16]. In this study only 1/30 patient (3.3%) never benefited from masitinib, suggesting that masitinib may be less susceptible to early resistance; although further investigation is required to confirm this hypothesis.

The objective response (RECIST) and metabolic response rate at 2 months are in the range of those observed with imatinib [12, 24]. Combinations of morphologic (Computed Tomography) and functional imaging techniques such as FDG-PET or Dynamic Contrast Enhanced-Ultrasonography (DCE-US) [25] highlight again the discrepancy between the biological (cellular level) and clinical (radiological level) activities of TKIs in GIST [11, 26, 27]. As observed with imatinib, masitinib induces changes in the tumour structure, such as decreased tumour vascularity, haemorrhage or necrosis, cystic or myxoid degeneration, that are consistent with a therapeutic activity with or without a change in tumour volume. When these three different radiological tumour assessments were applied to the same patients, masitinib was found to induce tumour response in only 20% of evaluable patients according to changes in tumour size (RECIST) but in 86% of patients according to metabolic response using FDG-PET and in 75% of patients assessed with DCE-US [28], after 2 months of masitinib. Interestingly, one patient with an FDG-PET CMR observed after 2 months of masitinib had a decrease but not a disappearance of contrast uptake with DCE-US performed concomitantly, suggesting that this less expensive tool assessing both tumour size and structure may be a more reliable measure of the residual activity of GIST tumour cells than FDG-PET. As for imatinib [25] and other TKIs [28], a decrease of contrast uptake assessed with DCE-US, 7 and 14 days after the beginning of masitinib, correlates with a good response on CT scan at 2 months [28].

As already reported, RECIST is not optimal for an early response assessment of c-Kit inhibitors in GIST patients [29] since the pattern of radiological response has no prognostic value for further outcome, except for PD [30]. However, RECIST assessment can be used for practical decision making since absence of progression according to RECIST turned out to be an excellent predictive marker of benefit with masitinib in terms of PFS. Consequently, masitinib needs to be continued as long as there is no progression according to RECIST; an absence of tumour progression under masitinib being equivalent to tumour response.

Twelve of the 16 patients who withdrew from the study (eight for PD, three for AEs, and one on the investigator's decision) were switched to imatinib-treatment. Of the eight patients progressing under masitinib, six received imatinib at 800 mg/day and two received imatinib at 400 mg/kg/day, with a median exposure of 5.4 months. Six of these patients discontinued imatinib for AEs or progression, the remainder (one at each dose level) showed some relevant disease stabilization. This suggests that the use of a less selective c-Kit inhibitor (i.e. imatinib) in second line therapy precludes any relevant activity in terms of tumour volume reduction and that therefore, patients progressing under masitinib are candidates for alternative second-line targeted therapies [31]. Of those patients intolerant to masitinib; one died, one had PD and switched to an alternate second line therapy, and the other showed a PR.

This study was designed to assess the objective response rate according to RECIST at 2 months under masitinib, although the time to secondary resistance to masitinib (i.e. PFS) would have been a more relevant activity screening end-point (as with imatinib or sunitinib). Despite this study's small number of patients (with a majority of GIST harbouring a c-Kit exon 11 mutation), a median follow-up of 33.7 months and the limited validity of comparison with phase III trials; the median PFS (41.3 months), as well as the 2- and 3-year PFS rates (60% and 55%, respectively) observed with masitinib, compare favourably with those of imatinib at 400 mg/day [5, 12].

In summary, the activity of masitinib in GIST could in part be due to: (1) its potent inhibition of WT and JM c-Kit that limits tumour proliferation and emergence of resistant cell clones; (2) its partial inhibition of the FAK pathway that may limit the development of metastases, thus, slowing down progression [32]; and (3) individual adaptation of the daily dose that may offer an optimal dose over time. Indications that masitinib provides sustainable benefits, as evidenced by the 2 and 3 year OS data, are promising, but its impact on OS has to be further determined with a follow-up of those responding patients (43%) still receiving treatment, as well as progressing patients who went on to receive alternative treatments [5].

Conclusion; Results from this study help to further establish the therapeutic role of TKIs that selectively inhibit c-Kit [5, 11-13]. Moreover, within the limitations of an uncontrolled phase 2 trial, this study shows that masitinib may offer an effective and relatively well-tolerated treatment for nonpre-treated, inoperable, locally advanced or metastatic GIST patients. Confirmatory phase III trials comparing masitinib to imatinib in first-line treatment will confirm the validity of these findings and help to further investigate the long-term efficacy and safety of masitinib.

BIBLIOGRAPHY INCORPORATED HEREIN BY REFERENCE

1. Hirota, S., et al., *Gain-of-function mutations of c-kit in human gastrointestinal stromal tumors.* Science, 1998. 279 (5350): p. 577-80.
2. Kindblom, L. G., et al., *Gastrointestinal pacemaker cell tumor (GIPACT): gastrointestinal stromal tumors show phenotypic characteristics of the interstitial cells of Cajal.* Am J Pathol, 1998. 152(5): p. 1259-69.
3. Heinrich, M. C., et al., *PDGFRA activating mutations in gastrointestinal stromal tumors.* Science, 2003. 299(5607): p. 708-10.
4. Sleijfer, S., et al., *Improved insight into resistance mechanisms to imatinib in gastrointestinal stromal tumors: a basis for novel approaches and individualization of treatment.* Oncologist, 2007. 12(6): p. 719-26.
5. Blanke, C. D., et al., *Long-term results from a randomized phase II trial of standard-versus higher-dose imatinib mesylate for patients with unresectable or metastatic gastrointestinal stromal tumors expressing KIT.* J Clin Oncol, 2008. 26(4): p. 620-5.
6. Demetri, G. D., et al., *Imatinib plasma levels are correlated with clinical benefit in patients with unresectable/metastatic gastrointestinal stromal tumors.* J Clin Oncol, 2009. 27(19): p. 3141-7.
7. Dubreuil, P., et al., *Masitinib (AB1010), a potent and selective tyrosine kinase inhibitor targeting KIT.* PLoS ONE, 2009. 4(9): p. e7258.
8. Darzynkiewicz, Z., et al., *Features of apoptotic cells measured by flow cytometry.* Cytometry, 1992. 13(8): p. 795-808.
9. Therasse, P., et al., *New guidelines to evaluate the response to treatment in solid tumors. European Organization for Research and Treatment of Cancer, National Cancer Institute of the United States, National Cancer Institute of Canada.* J Natl Cancer Inst, 2000. 92(3): p. 205-16.
10. Jager, P. L., J. A. Gietema, and W. T. van der Graaf, *Imatinib mesylate for the treatment of gastrointestinal stromal tumours: best monitored with FDG PET.* Nucl Med Commun, 2004. 25(5): p. 433-8.
11. Demetri, G. D., et al., *Efficacy and safety of imatinib mesylate in advanced gastrointestinal stromal tumors.* N Engl J Med, 2002. 347(7): p. 472-80.
12. Verweij, J., et al., *Progression free survival in gastrointestinal stromal tumours with high-dose imatinib: randomised trial.* Lancet, 2004. 364(9440): p. 1127-34.
13. Blanke, C. D., et al., *Phase III randomized, intergroup trial assessing imatinib mesylate at two dose levels in patients with unresectable or metastatic gastrointestinal stromal tumors expressing the kit receptor tyrosine kinase: S0033.* J Clin Oncol, 2008. 26(4): p. 626-32.
14. Blay, J. Y., et al., *Prospective multicentric randomized phase III study of imatinib in patients with advanced gastrointestinal stromal tumors comparing interruption versus continuation of treatment beyond 1 year: the French Sarcoma Group.* J Clin Oncol, 2007. 25(9): p. 1107-13.
15. Heinrich, M. C., et al., *Molecular correlates of imatinib resistance in gastrointestinal stromal tumors.* J Clin Oncol, 2006. 24(29): p. 4764-74.
16. Van Glabbeke, M., et al., *initial and late resistance to imatinib in advanced gastrointestinal stromal tumors are predicted by different prognostic factors: a european organisation for research and treatment of cancer-Italian sarcoma group-Austraasian gastrointestinal trials groups study.* J Clin Oncol, 2005. 23(24): p. 5795-5803.
17. Blay, J. Y., et al., *Consensus meeting for the management of gastrointestinal stromal tumors. Report of the GIST Consensus Conference of 20-21 Mar. 2004, under the auspices of ESMO.* Ann Oncol, 2005. 16(4): p. 566-78.
18. Debiec-Rychter, M., et al., *KIT mutations and dose selection for imatinib in patients with advanced gastrointestinal stromal tumours.* Eur J Cancer, 2006. 42(8): p. 1093-103.
19. Van Glabbeke, M., et al., *Comparison of two doses of imatinib for the treatment of unresectable or metastatic gastrointestinal stromal tumors (GIST): A meta-analyis based on 1,640 patients (pts),* in *J Clin Oncol ASCO annual Meeting Proceedings.* 2007. p. 10004.
20. Zalcberg, J. R., et al., *Outcome of patients with advanced gastro-intestinal stromal tumours crossing over to a daily imatinib dose of 800 mg after progression on 400 mg.* Eur J Cancer, 2005. 41(12): p. 1751-7.
21. Soria, J. C., et al., *Phase 1 dose-escalation study of oral tyrosine kinase inhibitor masitinib in advanced and/or metastatic solid cancers.* Eur J Cancer, 2009. 45(13): p. 2333-41.
22. Tebib, J., et al., *Masitinib in the treatment of active rheumatoid arthritis: results of a multicentre, open-label, dose-ranging, phase 2a study.* Arthritis Res Ther, 2009. 11(3): p. R95.
23. Van Glabbeke, M., et al., *Predicting toxicities for patients with advanced gastrointestinal stromal tumours treated with imatinib: a study of the European Organisation for Research and Treatment of Cancer, the Italian Sarcoma Group, and the Australasian Gastro-Intestinal Trials Group (EORTC-ISG-AGITG).* Eur J Cancer, 2006. 42(14): p. 2277-85.
24. Choi, H., et al., *Correlation of computed tomography and positron emission tomography in patients with metastatic gastrointestinal stromal tumor treated at a single institution with imatinib mesylate: proposal of new computed tomography response criteria.* J Clin Oncol, 2007. 25(13): p. 1753-9.
25. Lassau, N., et al., *Gastrointestinal stromal tumors treated with imatinib: monitoring response with contrast-enhanced sonography.* AJR Am J Roentgenol, 2006. 187(5): p. 1267-73.
26. Prior, J. O., et al., *Early prediction of response to sunitinib after imatinib failure by 18F-fluorodeoxyglucose positron emission tomography in patients with gastrointestinal stromal tumor.* J Clin Oncol, 2009. 27(3): p. 439-45.
27. Van den Abbeele, A. D. and R. D. Badawi, *Use of positron emission tomography in oncology and its potential role to assess response to imatinib mesylate therapy in gastrointestinal stromal tumors (GISTs).* Eur J Cancer, 2002. 38 Suppl 5: p. S60-5.
28. Chami, L., et al. *Quantitative functional imaging by dynamic contrast enhanced ultrasonography (DCE-US) in patients with GIST treated by tyrosine kinase inhibitor (TKI).* in *J Clin Oncol ASCO annual Meeting Proceedings.* 2008.
29. Benjamin, R. S., et al., *We should desist using RECIST, at least in GIST.* J Clin Oncol, 2007. 25(13): p. 1760-4.
30. Le Cesne, A., et al., *Absence of progression as assessed by RECIST predicts survival in advanced gastro-intestinal* tumors (*GIST*) *treated with imatinib mesylate: analysis of the intergroup EORTC-ISG-AGITG phase III trial*. J Clin Oncol, in press.
31. Demetri, G. D., et al., *Efficacy and safety of sunitinib in patients with advanced gastrointestinal stromal tumour after failure of imatinib: a randomised controlled trial*. Lancet, 2006. 368(9544): p. 1329-38.
32. Siesser, P. M. and S. K. Hanks, *The signaling and biological implications of FAK overexpression in cancer*. Clin Cancer Res, 2006. 12(11 Pt 1): p. 3233-7.

What is claimed is:

1. A method for treating Gastrointestinal Stromal Tumours (GIST) in a subject, wherein said method comprises the administration of an effective amount of masitinib or a pharmaceutically acceptable salt thereof to said subject.

2. The method of claim 1, wherein said treatment is for the treatment of secondary Gastrointestinal Stromal Tumours (GIST).

3. The method of claim 1, wherein said treatment comprises the oral administration of masitinib or a pharmaceutically acceptable salt thereof to a subject in need thereof.

4. The method of claim 1, wherein said effective amount of masitinib or a pharmaceutically acceptable salt thereof is a daily dose depending on the patient weight.

5. The method of claim 1, wherein said effective amount of masitinib or a pharmaceutically acceptable salt thereof is administered in two intakes a day.

6. The method of claim 1, wherein said subject is a human patient.

7. The method of claim 1, wherein said masitinib or a pharmaceutically acceptable salt thereof is administered in a composition comprising a dose of 100 mg of masitinib or a pharmaceutically acceptable salt thereof.

* * * * *